(12) United States Patent
Gravestock

(10) Patent No.: US 6,638,955 B2
(45) Date of Patent: Oct. 28, 2003

(54) ANTIBIOTIC OXAZOLIDINONE DERIVATIVES

(75) Inventor: Michael Barry Gravestock, Macclesfield (GB)

(73) Assignee: Syngenta Limited, London (GB)

(*) Notice: Subject to any disclaimer, the term of this patent is extended or adjusted under 35 U.S.C. 154(b) by 0 days.

(21) Appl. No.: 10/032,584

(22) Filed: Dec. 21, 2001

(65) Prior Publication Data

US 2002/0133022 A1 Sep. 19, 2002

Related U.S. Application Data

(62) Division of application No. 09/836,095, filed on Apr. 17, 2001, now Pat. No. 6,365,751, which is a division of application No. 09/364,389, filed on Jul. 30, 1999, now Pat. No. 6,271,383, which is a division of application No. 08/945,160, filed as application No. PCT/GB97/00462 on Apr. 17, 1997, now Pat. No. 5,981,528.

(30) Foreign Application Priority Data

Feb. 24, 1996 (GB) ............................................... 9603939
Sep. 4, 1996 (GB) ............................................... 9618404

(51) Int. Cl.$^7$ .................... C07D 413/10; A61K 31/422
(52) U.S. Cl. ...................... 514/340; 546/209; 546/215; 548/229; 514/374
(58) Field of Search .................... 548/229; 546/209, 546/215; 514/374, 340

(56) References Cited

U.S. PATENT DOCUMENTS

| | | | |
|---|---|---|---|
| 4,287,351 A | 9/1981 | Bourgery et al. |
| 4,346,102 A | 8/1982 | Langlois et al. |
| 4,476,136 A | 10/1984 | Dostert et al. |
| 4,705,799 A | 11/1987 | Gregory |
| 4,977,173 A | 12/1990 | Brittelli et al. |
| 5,043,443 A | 8/1991 | Carlson et al. |
| 5,164,510 A | 11/1992 | Brickner |
| 5,182,403 A | 1/1993 | Brickner |
| 5,231,188 A | 7/1993 | Brickner |
| 5,523,403 A | 6/1996 | Barbachyn |
| 5,529,998 A | 6/1996 | Habich et al. |
| 5,547,950 A | 8/1996 | Hutchinson et al. |
| 5,565,571 A | 10/1996 | Barbachyn et al. |
| 5,574,055 A | 11/1996 | Borgulya et al. |
| 5,652,238 A | 7/1997 | Brickner et al. |
| 5,719,154 A | 2/1998 | Tucker et al. |

FOREIGN PATENT DOCUMENTS

| | | |
|---|---|---|
| AU | 24985/95 | 2/1996 |
| AU | 50735/96 | 10/1996 |
| CA | 2154024 | 1/1996 |
| EP | 0127902 | 12/1984 |
| EP | 0184170 | 6/1986 |
| EP | 0312000 | 4/1989 |
| EP | 0316594 | 5/1989 |
| EP | 0352781 | 1/1990 |
| EP | 0657440 | 6/1995 |
| EP | 0693491 | 1/1996 |
| EP | 0694543 | 1/1996 |
| EP | 0694544 | 1/1996 |
| EP | 0738726 | 10/1996 |
| FR | 2458547 | 1/1981 |
| FR | 2500450 | 8/1982 |
| GB | 2028306 | 3/1980 |
| GB | 2053196 | 2/1981 |
| GB | 2094299 | 9/1982 |
| WO | WO 93/09103 | 5/1993 |
| WO | WO 93/23384 | 11/1993 |
| WO | WO 94/01110 | 1/1994 |
| WO | WO 94/13649 | 6/1994 |
| WO | WO 95/07271 | 3/1995 |
| WO | WO 95/14684 | 6/1995 |
| WO | WO 95/25106 | 9/1995 |
| WO | WO 96/13502 | 5/1996 |
| WO | WO 96/15130 | 5/1996 |
| WO | WO 96/23788 | 8/1996 |
| WO | WO 96/35691 | 11/1996 |
| WO | WO 97/09328 | 3/1997 |
| WO | WO 97/10223 | 3/1997 |
| WO | WO 97/10235 | 3/1997 |
| WO | WO 97/14690 | 4/1997 |
| WO | WO 97/19089 | 5/1997 |
| WO | WO 97/21708 | 6/1997 |
| WO | WO 97/27188 | 7/1997 |
| WO | WO 97/30981 | 8/1997 |
| WO | WO 97/37980 | 10/1997 |

OTHER PUBLICATIONS

Abstracts: The 1996 ICAAC (Interscience Congress of Antimerbial Agents and Chemotheraphy), New Orleans, 41, 52, 140 (Sep. 1996).

Ashtekar, D. et al. Oxazolidinones, a New Class of Synthetic Antituberculosis Agent: In vitro and vivo Activities of Dup–721 Against Mycobacterium tuberculosis. *Diagn. Microbiol. Infect. Dis.* 14, 465–471 (1991).

Barbachyn, M. et al. Identification of a Novel Oxazolidinone (U–100480) with Potent Antimycobacterial Activity. *J. Med. Chem.* 39, 680–685 (1996).

(List continued on next page.)

Primary Examiner—Joseph K. McKane
Assistant Examiner—Kamal Saeed
(74) Attorney, Agent, or Firm—Ropes & Gray

(57) ABSTRACT

The present application discloses a class of antibiotic compounds containing an oxazolidinone ring. These compounds have useful activity against Gram-positive pathogens including MRSA and MRCNS and, in particular, against various strains exhibiting resistance to vancomycin and against *E. faecium* strains resistant to both aminoglycosides and clinically used β-lactams. The compounds also possess a favorable toxicological profile. This invention further relates to processes for their preparation, to intermediates useful in their preparation, to their use as therapeutic agents and to pharmaceutical compositions containing them.

6 Claims, No Drawings

OTHER PUBLICATIONS

Barbachyn, M. et al. Synthesis and Antibacterial of New Tropone–Substituted Phenyloxazolidinone Antibacterial Agents. *Bioorganic and Medicinal Chem. Letters* 6, 1003–1014 (1996).

Barry, A. et al. In Vitro Evaluation of Dup 105 and Dup 721, Two New Oxazolidinone Antimicrobial Agents. *Antimicrobial Agents and Chemotherapy* 32, 150–152 (1988).

Borthwick, A. et al. 5–(Acetamidomethyl)–3–Aryldihydrofuran–2–ones, and 5–(Acetamidomethyl)–3–Aryltetrahydrofuran–2–ones, Two New Classes of Antibacterial Agents. *Med. Chem. Res.* 6, 22–27 (1996).

Brickner, S. et al. Oxazolidinone Antibacterial Agents. *Current Pharmaceutical Design* 2, 175–194 (1996).

Brickner, S. et al. Synthesis and Antibacterial Activity of U–100592 and U–100766, Two Oxazolidinone Antibacterial Agents for the Potential Treatment of Multidrug–Resistant Gram–Positive Bacterial Infections. *J. Med. Chem.* 39, 673–679 (1996).

Brumfitt, W. et al. Antibacterial Oxazolidinones: In Vitro Activity of a New Analogue, E33709. *Diagn. Microbiol. Infect. Dis.* 15, 621–625 (1992).

Brumfitt, W. et al. In–vitro Microbiological Activities of Dup 105 and Dup 721, Novel Synthetic Oxazolidinones. *J. Antimicrobial Chemotherapy* 21, 711–720 (1988).

Brumfitt, W. et al. Variation in Response of Gram–Positive cocci to the Combination Dup 721 and ciprofloxacin. *J. Antimicrob. Chemotherapy* 24, 465–466 (1989).

Daly, J. et al. Activity and Mechanism of Action of Dup 105 and Dup 721, New Oxazolidinone Compounds. *J. Antimicrobial Chemotherapy* 21, 721–730 (1988).

Denis, A. et al. 5–Aryl–beta, gamma Butenolide, A New Class of Antibacterial Derived from the N–Aryl Oxazolidinone Dup 721. *Bioorganic and Med. Chem. Letters* 4, 1925–1930 (1994).

Dostert, P. et al. Structural Modifications in Oxazolidinone Series Leading to Type A or B Selective Monoamine Oxidase Inhibitors. *Int. Congress Series, Excerpta Medica* 564, 197–208 (1982).

Eliopoulos, G. et al. In Vivo Activities of New Oxazolidinone Antimicrobial Agents against Enterococci. *Antimicrobial Agents and Chemotherapy* 3240, 1745–1747 (1996).

Eustice, D. et al. An Automated Pulse Labeling Method for Structure–Activity Relationship Studies with Antibacterial Oxazolidinones. *Drugs Exp. Clin. Res.* 16, 149–155 (1990).

Eustice, D. et al. Mechanism of Action of Dup 721: Inhibition of an Early Event during Initiation of Protein Synthesis *Antimicrobial Agents and Chemotherapy* 32, 1218–1222 (1988).

Eustice, D. et al. The Mechanism of Action of Dup 721, a New Antibacterial Agent: Effects on Macromolecular Synthesis. *Biochem. And Biophys. Res. Comm.* 150, 965–971 (1988).

Ford, C. et al. In Vivo Activities of U–100592 and U–100766, Novel Oxazolidinone Antimicrobial Agents, against Experimental Bacterial Infections. *Antimicrobial Agents and Chemotherapy* 40, 1508–1513 (1996).

Grega, K. et al. Regioselective Metalation of Fluoroanilines. An Application to the Synthesis of Fluorinated Oxazolidinone Antibacterial Agents. *J. Org. Chem.* 60, 5255–5261 (1995).

Gregory, W. et al. Antibacterials. Synthesis and Structure––Activity Studies of 3–Aryl–2–Oxazolidinones. 1. The "B" Group. *J. Med. Chem.* 32, 1673–1681 (1989).

Gregory, W. et al. Antibacterials. Synthesis and Structure––Activity Studies of 3–Aryl–2–oxooxazolidines. 2. The "A" Group. *J. Med. Chem.* 33, 2569–2578 (1990).

Hutchinson, D. et al. Piperazinyl Oxazolidinones: Structure Relationship of a New Class of Oxazolidinone Antibacterial Agents. *Interscience Congress of Antimicrobial Agents and Chemotherapy* Abstract 8–14 (Sep. 1995).

Jones, R. et al. In Virto Antimicrobial Activities and Spectra of U–100592 and U–100766, Two Novel Fluorinated Oxazolidinones. *Antimicrobial Agents and Chemotherapy* 40, 720–726 (1996).

Jorgensen, J. et al. In Vitro Activities of the Oxazolidinone Antibodies U–100592 and U–100766 against Staphylococcus aureus and Coagulase–Negative Staphylococcus Species. *Antimicrobial Agents and Chemotherapy* 41, 465–467 (Feb. 1997).

Kaatz, G. et al. In Vitro Activities of Oxazolidinone Compounds U100592 and U100766 against Staphylococcus aureus and Staphylococcus epidermis. *Antimicrobial Agents and Chemotherapy* 40, 799–801 (1996).

Lin, A. et al. The Oxazolidinone Eperezolid Binds to the 50S Ribosonal Subunit and Competes with Binding of Chloramphenical and Lincomycin. *Antimicrobial Agents and Chemotherapy* 41, 2127–2131 (1997).

Lizondo, J. et al. Linezolid U–100766. *Drugs of the Future* 21, 1116–1123 (1996).

Lund, J. et al. Hypersrgmented Megakaryocytes and Megakaryocytes with Multiple Separate Nuclei in Dogs Treated with PNU–100592, an Oxazolidinone Antibiotic. *Toxicologic Pathology* 25, 339–343 (1997).

Maple, P. et al. Comparative in–vitro activity of vancomycin, teicoplanin, ramoplanin (formerly A16686), paldimycin, Dup 721 and Dup 105 against methicillin and gentamicin resistant Staphylococcus aureus. *J. Antimicrobial chemitherapy* 23, 517–525 (1989).

Mason, E. et al. In Vitro Activities of Oxazolidinones U–100592 and U–100766 against Penicillin–Resistant and Cephalosporin–Resistant Strains of Streptococcus pneumoniae. *Antimicrobial Agents and Chemotherapy* 40, 1039–1040 (1996).

Mini, E. et al. Comparative in Vitro Activity of the New Oxazolidinones Dup 721 and Dup 105 against Staphylococci and Streptococci. *Eur. J. Clin. Microbiol. Infect. Dis.* 8, 256–260 (1989).

Mulazimoglu, L. et al. In Vitro Activities of Two Novel Oxazolidinones (U100592 and U100766), a New Fluoroquinolone (Trovafloxacin), and Dalfopristin–Quinupristin against Staphylococcus aureus and Staphylococcus epidermis. *Antimicrobial Agents and Chemotherapy* 40, 2428–2430 (1996).

Neu, H. et al. In Vitro Activities of Two Oxazolidinone Antimicrobial Agents, Dup 721 and Dup 105. *Antimicrobial Agents and Chemotherapy* 32, 580–583 (1988).

Park, C. et al. Antibacterials. Synthesis and Structure–Activity Studies of 3–Aryl–2–Oxazolidinones. 4. Multiply–Substituted Aryl Derivatives. *J. Med. Chem.* 35, 1156–1165 (1992).

Ranaldi, G. et al. Transport of the Antibacterial Agent Oxazolidin–2–One and Derivatives across Intestinal (Caco–2) and Renal (MDCK) Epithelial Cell Lines. *Antimicrobial Agents and Chemotherapy* 40, 652–658 (1996).

Schaadt, R. et al. Serum Inhibitory Titera and Serum Bacterial Titers for Human Subjects Receiving Multiple Doses of the Antibacterial Oxazolidinones Eperezolid and Linezolid. *Diagn. Microbiol. Infect. Dis.* 28, 201–204 (1997).

Schaus, S. et al. Dynamic Kinetic Resolution of Epichlorohydrin via Enantioselective Catalytic Ring Operation with TMSN3. Practical Synthesis of Aryl Oxazolidinone Antibacterial Agents. *Tetrahedron Letters* 37, 7937–7940 (1996).

Scholl, J. et al. Micellar Electrokinetic Chromatography as a Generalized Alternative to High–Performance Liquid Chromatography for Purity Determination of a Class of Investigational Antibacterial Drugs. *J. Chromatography* 695, 147–156. (1997).

Seneci, P. et al. Synthesis and Antimicrobial Activity of Oxazolidin–2–ones and Related Heterocycles. *J. Chem. Soc. Perkin Trans.* 1, 16, 2345–2351 (1994).

Shinabarger, D. et al. Mechanism of Action of Oxazolidinones: Effects of Linezolid and Eperezolid on Translation Reactions. *Antimicrobial Agents and Chemotherapy* 41, 2132–2136 (1997).

Silverman, R. et al. The Oxazolidinone Antibacterial Agent DuP 105 Does Not Act on Cell Wall Biosynthesis or on a Beta–Lactamase. *Biochemical and Biophys. Res. Comm.* 195, 1077–1080 (1993).

Slee, A. et al. Oxazolidinones, a New Class of Synthetic Antibacterial Agents: In Vitro and In Vivo Activities of DuP 105 and DuP 721. *Antimicrobial Agents and Chemotherapy* 31, 1791–1797 (1987).

Spangler, S. et al. Activities of RPR 106972 (a New Oral Streptogramin), Cefditoren (a New Oral Cephalosporin), Two New Oxazolidinones (U–100592 and U–100766), and Other Oral and Parenteral Agents against 203 Penicillin–Susceptible and—Resistant Pneumococci. *Antimicrobial Agents and Chemotherapy* 40, 481–484 (1996).

Takagi, H. et al. Safety Pharmacology Evaluation of the Oxazolidinone, U–100766. *Society of Toxicologists Annual Meeting*–Abstract 110, (1996).

Wang, C. et al. Chiral Synthesis fo DuP 721, a New Antibacterial Agent. *Tetrahedron* 45, 1323–1326 (1989).

Worth, S. et al. Quality Control Guidelines for Amoxicillin, Amoxicillin–Clavulanate, Azithromycin, Piperacillin–Tazobactam, Roxithromycin, Ticarcillin, Clavulanate, Trovafloxacin (CP 99,219), U–100592, and U–100766 for Various National Committee . . . *Diagn. Microbiol. Infect. Dis.* 24, 87–91 (1996).

Zurenko, G. et al. In Vitro Activities of U–100592 and U–100766, Novel Oxazolidinone Antibacterial Agents. *Antimicrobial Agents and Chemotherapy* 40, 839–845 (1996).

Zurenko, G. et al. Oxazolidinone antibacterial agents: Development of the Clinical Candidates Eperezolid and Linezolid. *Exp. Opin. Invest. Drugs* 6, 151–158 (1997).

ANTIBIOTIC OXAZOLIDINONE DERIVATIVES

This application is a divisional of U.S. patent application No. 09/836,095, filed Apr. 17, 2001, now U.S. Pat. No. 6,365,751, which is a divisional of U.S. patent application No. 09/364,389, filed Jul. 30, 1999, now U.S. Pat. No. 6,271,383, which is a divisional of U.S. patent application No. 08/945,160, filed Oct. 21, 1997, now U.S. Pat. No. 5,981,528, which is a national-stage filing under 35 U.S.C. 371 of International Application PCT/GB97/00462, filed Feb. 20, 1997, which claims priority from United Kingdom Application Nos. 9603939.1, filed Feb. 24, 1996, and 9618404.9, filed Sep. 4, 1996, the specifications of all of which are incorporated by reference herein in their entirety. International Application PCT/GB97/00462 was published under PCT Article 21(2) in English.

The present invention relates to antibiotic compounds and in particular to antibiotic compounds containing an oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant streptococcus pneumoniae and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a narrow range of compounds that is not suggested by the art and which has good activity against a broad range of Gram-positive pathogens including organisms known to be resistant to most commonly used antibiotics. In comparison with compounds described in the art (for example Walter A. Gregory et al in J.Med.Chem. 1990, 33, 2569–2578 and Chung-Ho Park et al in J.Med.Chem. 1992, 35, 1156–1165) the compounds also possess a favourable toxicological profile.

Accordingly the present invention provides a compound of the formula (1):

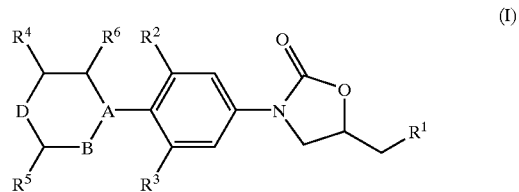

wherein:

$R^1$ is hydroxy, chloro, fluoro, (1–4C)alkanesulfonyloxy, amino, azido, (1–4C)alkoxy, (1–4C)alkylthio, (1–4C) alkylaminocarbonyloxy;

or of the formula —NHC(=O)$R^b$ wherein $R^b$ is hydrogen, (1–4C)alkoxy, amino, chloromethyl, dichloromethyl, cyanomethyl, methoxymethyl, acetylmethyl, methylamino, dimethylamino or (1–4C) alkyl;

or $R^1$ is of the formula —NHS(O)$_n$(1–4C)alkyl wherein n is 0, 1 or 2;

$R^2$ and $R^3$ are independently hydrogen or fluoro;

D is O, S, SO, SO$_2$ or NR$^7$;

when D is O, $R^4$ and $R^5$ are independently hydroxy, bromo, oxo (=O), (1–4C)alkyl, (1–4C)alkanoylamino-(1–4C)alkyl, hydroxy-(1–4C)alkyl, carboxy, (1–4C) alkoxycarbonyl, AR-oxymethyl, AR-thiomethyl (wherein AR is as defined hereinbelow) or independently as defined for $R^7$ hereinbelow;

when D is S, SO, SO$_2$ or NR$^7$, $R^4$ and $R^5$ are independently oxo (=O), (1–4C)alkyl,(1–4C)alkanoylamino-(1–4C)alkyl, hydroxy-(1–4C)alkyl, carboxy, (1–4C) alkoxycarbonyl, AR-oxymethyl, AR-thiomethyl (wherein AR is as defined hereinbelow) or independently as defined for $R^7$ hereinbelow;

$R^6$ is hydrogen, (1–4C)alkyl, hydroxy, (1–4C)alkoxy or (2–4C)alkanoyloxy; >A—B— is of the formula >C=C ($R^a$)—, >CHCHR$^a$— or >C(OH)CHR$^a$— (>represents two single bonds) wherein $R^a$ is hydrogen or (1–4C) alkyl;

$R^7$ is hydrogen, cyano, 2-((1–4C)alkoxycarbonylethenyl, 2-cyanoethenyl, 2-cyano-2-((1–4C)alkyl)ethenyl, 2-((1–4C)alkylaminocarbonyl)ethenyl, AR (as defined hereinbelow) or a tetrazole ring system (optionally mono-substituted in the 1- or 2-position of the tetrazole ring) wherein the tetrazole ring system is joined to the nitrogen in NR$^7$ by a ring carbon atom;

or $R^7$ is of the formula $R^{10}$CO—, $R^{10}$SO$_2$— or $R^{10}$CS— wherein $R^{10}$ is AR (as defined hereinbelow), cyclopentyl or cyclohexyl (wherein the last two-mentioned cycloalkyl rings are optionally mono- or disubstituted by substituents independently selected from (1–4C)alkyl (including geminal disubstitution), hydroxy, (1–4C)alkoxy, (1–4C)alkylthio, acetamido, (1–4C)alkanoyl, cyano and trifluoromethyl), (1–4C) alkoxycarbonyl, hydrogen, amino, trifluoromethyl, (1–4C)alkylamino, di((1–4C)alkyl)amino, 2,3-dihydro-5-oxothiazolo-[3,2-A]pyrimidin-6-yl, 2-(2-furyl)ethenyl, 2-(2-thieny)ethenyl, 2-phenylethenyl (wherein the phenyl substituent is optionally substituted by up to three substituents independently selected from (1–4C)alkoxy, halo and cyano), 3,4-dihydropyran-2-yl, coumal-5-yl, 5-methoxy-4-oxopyran-2-yl, N-acetylpyrrolidin-2-yl, 5-oxotetrahydrofuran-2-yl, benzopyranone or (1–10C) alkyl [wherein (1–10C)alkyl is optionally substituted by hydroxy, cyano, halo, (1–10C)alkoxy, trifluoromethyl, (1–4C)alkoxyl-(1–4C)alkoxy, (1–4C)alkoxy-(1–4C)alkoxy(1–4C)alkoxy, (1–4C) alkanoyl, (1–4C)alkoxycarbonyl, amino, (1–4C) alkylamino, di((1–4C)alkyl)amino, (1–6C) alkanoylamino, (1–4C)alkoxycarbonylamino, N-(1–4C)alkyl-N-(2–6C)alkanoylamino, (1–4C) alkylS(O)$_p$NH—, (1–4C)alkylS(O)$_p$((1–4C)alkyl)N—, fluoro(1–4C)alkylS(O)$_p$NH—, fluoro(1–4C) alkylS(O)$_p$((1–4C)alkyl)N—, phosphono, (1–4C) alkoxy(hydroxy)phosphoryl, di(1–4C) alkoxyphosphoryl, (1–4C)alkylS(O)$_q$—, phenylS(O)$_q$— (wherein the phenyl group is optionally substituted by up to three substituents independently selected from (1–4C)alkoxy, halo and cyano), or CY (as defined hereinbelow), wherein p is 1 or 2 and q is 0, 1 or 2];

or R$^{10}$ is of the formula R$^{11}$C(O)O(1–6C)alkyl wherein R$^{11}$ is an optionally substituted 5- or 6-membered heteroaryl, optionally substituted phenyl, (1–4C) alkylamino, benzyloxy-(1–4C)alkyl or optionally substituted (1–10C)alkyl;

or R$^{10}$ is of the formula R$^{12}$O— wherein R$^{12}$ is optionally substituted (1–6C)alkyl;

or R$^7$ is of the formula R$^d$OC(R$^e$)=CH(C=O), R$^f$C(=O)C(=O), R$^g$N=C(R$^h$)C(=O)— or R$^i$NHC(R$^j$)=CHC(=O)— wherein R$^d$ is (1–6C)alkyl, R$^e$ is hydrogen or (1–6C)alkyl, or R$^d$ and R$^e$ together form a (3–4C)alkylene chain, R$^f$ is hydrogen, (1–6C)alkyl, hydroxy(1–6C)alkyl, (1–6C) alkoxy(1–6C)alkyl, amino, (1–4C)alkylamino, di-(1–4C)alkylamino, (1–6C)alkoxy, (1–6C)alkoxy (1–6C)alkoxy, hydroxy(2–6C)alkoxy, (1–4C) alkylamino(2–6C)alkoxy, di-(1–4C)alkylamino(2–6C) alkoxy, R$^g$ is (1–6C)alkyl, hydroxy or (1–6C)alkoxy, R$^h$ is hydrogen or (1–6C)alkyl, R$^i$ is hydrogen, (1–6C)alkyl, optionally substituted phenyl or an optionally substituted 5- or 6-membered heteroaryl and R$^j$ is hydrogen or (1–6C)alkyl;

or R$^7$ is of the formula R$^{14}$CH(R$^{13}$)(CH$_2$)$_m$— wherein m is 0 or 1, R$^{13}$ is fluoro, cyano, (1–4C)alkoxy, (1–4) alkylsulfonyl, (1–4C)alkoxycarbonyl or hydroxy, (provided that when m is 0, R$^{13}$ is not fluoro or hydroxy) and R$^{14}$ is hydrogen or (1–4C)alkyl;

wherein AR is optionally substituted phenyl, optionally substituted phenyl(1–4C)alkyl, optionally substituted 5- or 6-membered heteroaryl, optionally substituted naphthyl or an optionally substituted 5/6 or 6/6 bicyclic heteroaryl ring system, in which the bicyclic heteroaryl ring systems may be linked via an atom in either of the rings comprising the bicyclic system, and wherein the mono- and bicyclic heteroaryl ring systems are linked via a ring carbon atom;

wherein CY is a 4-, 5- or 6-membered cycloalkyl ring, a 5- or 6-membered cycloalkenyl ring, naphthoxy, thiophen-2-yl, indol-1-yl, indol-3-yl, pyrimidin-2-ylthio, 1,4-benzodioxan-6-yl, sulfolan-3-yl, pyridin-2-yl; wherein any of the afore-mentioned ring systems in CY may be optionally substituted by up to three substituents independently selected from halo, (1–4C)alkyl (including geminal disubstitution when CY is a cycloalkyl or cycloalkcenyl ring), acyl, oxo and nitro-(1–4C)alkyl;

and pharmaceutically-acceptable salts thereof; except that

N-({5S})-3(4-(2-oxo-5,6-dihydropyran-4-yl)phenyl)-2-oxooxazolidin-5-ylmethyl)acetamide is excluded.

In this specification a '5- or 6-membered heteroaryl' and 'heteroaryl (monocyclic) ring' means a 5- or 6-membered aryl ring wherein 1, 2 or 3 of the ring atoms are selected from nitrogen, oxygen and sulfur. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

In this specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Particular examples of 5/6 and 6/6 bicyclic ring systems are indole, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

In this specification a '4-, 5- or 6-membered cycloalkyl ring' means a cyclobutyl, cyclopentyl or cyclohexyl ring; and a '5- or 6membered cycloalkenyl ring' a means cyclopentenyl or cyclohexenyl ring.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C) alkyl includes 1-bromoethyl and 2-bromoethyl.

Particular optional substituents for alkyl, phenyl (and phenyl containing moieties) and naphthyl groups and ring carbon atoms in heteroaryl (mono or bicyclic) rings in R$^{11}$, R$^{12}$, R$^i$ and AR include halo, (1–4C)alkyl, hydroxy, nitro, carbamoyl, (1–4C)alkylcarbamoyl, di-((1–4C)alkyl) carbamoyl, cyano, trifluoromethyl, trifluoromethoxy, amino, (1–4C)alkylamino, di((1–4C)alkyl)amino, (1–4C)alkyl S(O)$_q$—, (wherein q is 0, 1 or 2), carboxy, (1–4C) alkoxycarbonyl, (2–6C)alkenyl, (2–6C)alkynyl, (1–4C) alkanoyl, (1–4C)alkoxy, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1–4C)alkyl, cyano(1–4C)alkyl, (1–4C)alkanesulfonamido, aminosulfonyl, (1–4C)alkylaminosulfonyl and di-((1–4C) alkyl)aminosulfonyl. The phenyl and naphthyl groups and heteroaryl (mono- or bicyclic) rings in R$^{11}$, R$^i$ and AR may be mono- or disubstituted on ring carbon atoms with substituents independently selected from the above list of particular optional substituents.

Particular optional substituents for ring nitrogen atoms when R$^7$ is tetrazole, in heteroaryl groups in R$^{11}$, R$^{12}$, R$^i$ and AR, and in the nitrogen-containing rings in CY, which can be substituted without becoming quaternised include (1–4C) alkyl, (2–4C)alkenyl, (2–4C)alkynyl and (1–4C)alkanoyl.

Examples of halo groups include fluoro, chloro and bromo; examples of (1–4C)alkyl, include methyl, ethyl, and propyl and isopropyl; examples of (1–6C)alkyl include methyl, ethyl, propyl, isopropyl, pentyl and hexyl; examples of (1–10C)alkyl include methyl, ethyl, propyl, isopropyl, pentyl, hexyl, heptyl, octyl and nonyl; examples of (1–4C) alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of (1–4C) alkanesulfonyloxy include methylsulfonyloxy, ethylsulfonyloxy and propylsulfonyloxy; examples of (1–4C)alkylthio include methylthio and ethylthio; examples of (1–4C) alkylsulfonyl include methylsulfonyl and ethylsulfonyl; examples of (1–4C)alkylaminocarbonyloxy include methylaminocarbonyloxy and ethylaminocarbonyloxy; examples of (4C)alkanoylamino-(1–4C)alkyl include formanidomethyl, acetamidomethyl and acetamidoethyl; examples of (1–6C)alkoxy-(1–6C)alkyl include methoxymethyl, ethoxymethyl and 2-methoxyethyl; examples of (1–4C)alkoxycarbonyl include methoxycarbonyl, ethoxycarbonyl and propoxycarbonyl; examples of (2–4C)alkanoyloxy include acetyloxy and propionyloxy; examples of (1–4C)alkoxy include methoxy, ethoxy and propoxy; examples of(1–6C)alkoxy include methoxy, ethoxy, propoxy and pentoxy; examples of hydroxy-(2–6C)alkoxy include 2-hydroxyethoxy and 3-hydroxypropoxy; examples of (1–4C)alkylamino-(2–6C) alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of (1–4C)alkoxy-(1–4C) alkoxy and (1–6C)alkoxy-(1–6C)alkoxy include methoxymethoxy, 2-methoxyethoxy, 2-ethoxyethoxy and 3-methoxypropoxy; examples of (1–4C)alkoxy-(1–4C) alkoxy-(1–4C)alkoxy include 2-(methoxymethoxyethoxy, 2-(2-methoxyethoxy)ethoxy; 3-(2-methoxyethoxy)propoxy and 2-(2-ethoxyethoxy)ethoxy; examples of (1–4C) alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C) alkyl-N-(2-6C)alkanoylamino include N-methylacetamido, N-ethylacetamido and N-methylpropionamido; examples of (1–4C)alkylS(O)$_p$NH— wherein p is 1 or 2 include methylsulfinylamino, methylsulfonylamino, ethylsulfinylamino and ethylsulfonylamino; examples of (1–4C)alkylS (O)$_p$((1–4C)alkyl)NH— wherein p is 1 or 2 include methylsulfinylmethylamino, methylsulfonylmethylamino, 2-(ethylsulfinyl)ethylamino and 2-(ethylsulfonyl) ethylamino; examples of fluoro(1–4C)alkylS(O)$_p$NH— wherein p is 1 or 2 include trifluoromethylsulfinylamino and trifluoromethylsulfonylamino; examples of fluoro(1–4C) alkylS(O)$_p$((1–4C)alkyl)NH— wherein p is 1 or 2 include trifluoromethylsulfinylmethylamino and trifluoromethylsulfonylmethylamino examples of (1–4C)alkoxy(hydroxy) phosphoryl include methoxy(hydroxy)phosphoryl and ethoxy(hydroxy)phosphoryl; examples of di-(1–4C) alkoxyphosphoryl include di-methoxyphosphoryl, di-ethoxyphosphoryl and ethoxy(methoxy)phosphoryl: examples of 2(1–4C)alkoxycarbonyl)ethenyl include 2-methoxycarbonyl)ethenyl and 2-(ethoxycarbonyl)ethenyl; examples of 2-cyano-2-((1–4C)alkyl)ethenyl include 2-cyano-2-methylethenyl and 2-cyano-2-ethylethenyl; examples of 2-((1–4C)alkylaminocarbonyl)ethenyl include 2-(methylaminocarbonyl)ethenyl and 2-(ethylaminocarbonyl)ethenyl; examples of benzyloxy (1–4C)alkyl include benzyloxymethyl and benzyloxyethyl; examples of phenyl(1–4C)alkyl include benzyl and phenethyl; examples of phenylS(O)$_q$ wherein q is 0, 1 or 2 are phenylthio, phenylsulfinyl and phenylsulfonyl respectively; examples of (1–4C)alkylcarbamoyl include methylcarbamoyl and ethylcarbamoyl; examples of di((1–4C)alkyl) carbamoyl include di(methyl)carbamoyl and di(ethyl) carbamoyl; examples of a (3–4C)alkylene chain are trimethylene or tetramethylene; examples of (2–4C)alkenyl include allyl and vinyl; examples of (2–4C)alkynyl include ethynyl and 2-propynyl; examples of (1–4C)alkanoyl include formyl, acetyl and proplonyl; examples of hydroxyimino(1–4C)alkyl include hydroxyiminomethyl, 2-(hydroxyiminoethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of hydroxy(1–4C)alkyl and hydroxy(1–6C)alkyl include hydroxymethyl, 1-hydroxyethyl, 2-hydroxyethyl and 3-hydroxypropyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include amninomethyl, 1-aminoethyl, 2-amninomethyl and 3-aminopropyl; examples of cyano (1–4C)alkyl include cyanomethyl, 1-cyanoethyl, 2-cyanoethyl and 3-cyanopropyl; examples of (1–4C) alkanesulfonamido include methanesulfonamido and ethanesulfonamido; examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (1) may be administered in the form of a pro-drug which is broken down in the human or animal body to give a compound of the formula (I). Examples of prodrugs include in-vivo hydrolysable esters of a compound of the formula (I).

An in-vivo hydrolysable ester of a compound of the formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C) cycloalkoxycarbonyloxy(1–6C)alkyl esters for example 1-cyclohexylcarbonyloxyethyl, 1,3dioxolen-2-onylmethyl esters for example 5-methyl-1,3-dioxolen-2-onylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) containing a hydroxy group includes inorganic esters such as phosphate esters and α-acyloxyalkyl ethers and related compounds which as a result of the in-vivo hydrolysis of the ester breakdown to give the parent hydroxy group. Examples of α-acyloxyalkyl ethers include acetoxymethoxy and 2,2-dimethylpropionyloxymethoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention have a chiral centre at the C-5 position of the oxazolidinone ring. The pharmaceutically active enantiomer is of the formula:

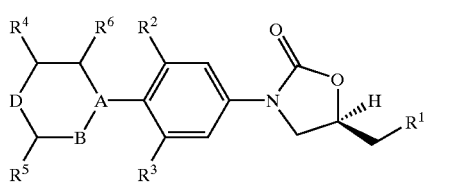

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above could be either 5R or 5S depending upon the value of $R^1$. For example, when $R^1$ is acetamido, the enantiomer depicted above is the 5S enantiomer and when $R^1$ is hydroxy, the enantiomer depicted above is the 5R enantiomer.

Furthermore, some compounds of the formula (I) may have other chiral centres, and some compounds of the formula (I) may exist as one or more regioisomers. It is to be understood that the invention encompasses all such optical, diastereo- and regio-isomers that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

In a preferred aspect of the invention there is provided a compound of the formula (I) as defined above, except that in the definition of $R^4$ and $R^5$, neither $R^4$ nor $R^5$ can be oxo (=O).

In another aspect the present invention provides a compound of the formula (I) wherein:

$R^1$ is hydroxy, chloro, fluoro, (1–4C)alkanesulfonyloxy, amino, azido, (1–4C)alkoxy, (1–4C)alkylthio, (1–4C)alkylaminocarbonyloxy, or of the formula —NHC(=O)$R^b$ wherein $R^b$ is hydrogen, (1–4C)alkoxy, amino, chloromethyl, dichloromethyl, cyanomethyl, methoxymethyl, acetylmethyl, methylamino, dimethylamino or (1–4C)alkyl;

or $R^1$ is of the formula —NHS(O)$_n$(1–4C)alkyl wherein n is 0, 1 or 2;

$R^2$ and $R^3$ are independently hydrogen or fluoro;

when D is O, $R^4$ and $R^5$ are independently hydrogen, hydroxy, bromo, oxo (=O), (1–4C)alkyl, carboxy, (1–4C)alkoxycarbonyl or independently as defined for $R^7$ hereinbelow;

when D is S, SO, SO$_2$ or NR$^7$, $R^4$ and $R^5$ are independently hydrogen, oxo (=O), (1–4C)alkyl, carboxy, (1–4C)alkoxycarbonyl or independently as defined for $R^7$ hereinbelow;

$R^6$ is hydrogen, (1–4C)alkyl, hydroxy, (1–4C)alkoxy or (2–4C)alkanoyloxy; >A—B— is of the formula >C=C(R$^a$), >CHCHR$^a$ or >C(OH)CHR$^a$— (>represents two single bonds) wherein R$^a$ is hydrogen or (1–4C)alkyl;

D is O, S, SO, SO$_2$ or NR$^7$;

wherein $R^7$ is hydrogen, cyano, 2-((1–4C)alkoxycarbonyl)ethenyl, 2-((1–4C)alkylaminocarbonyl)ethenyl, optionally substituted phenyl, optionally substituted phenyl(1–4C)alkyl, optionally substituted 5- or 6-membered heteroaryl, optionally substituted naphthyl or optionally substituted 5/6 or 6/6 bicyclic heteroaryl ring system wherein the heteroaryl ring systems are joined to the the nitrogen by a ring carbon atom;

or $R^7$ is of the formula $R^{10}$CO— or $R^{10}$SO$_2$— wherein $R^{10}$ is (1–4C)alkoxycarbonyl, amino, (1–4C)alkylamino, di((1–4C)alkyl)amino or (1–6C)alkyl [wherein (1–6C)alkyl is optionally substituted by hydroxy, cyano, amino, (1–4C)alkoxy, (1–4C)alkanoyl, (1–4C)alkylamino, di((1–4C)alkyl)amino, (2–6C)alkanoylamino, N-(1–4C)alkyl-N-(2–6C)alkanoylamino, (1–4C)alkylS(O)$_p$NH—, (1–4C)alkylS(O)$_p$((1–4C)alkyl)N—, phosphono, (1–4C)alkoxy(hydroxy)phoryl, di-(1–4C)alkoxyphosphoryl or (1–4C)alkylS(O)$_q$ wherein p is 1 or 2 and q is 0, 1 or 2];

or $R^{10}$ is of the formula $R^{11}$C(O)O(1–6C)alkyl wherein $R^{11}$ is optionally substituted 5- or 6-membered heteroaryl, optionally substututed phenyl or optionally substituted (1–6C)alkyl;

or $R^{10}$ is of the formula $R^{12}$O— wherein $R^{12}$ is optionally substituted (1–6C)alkyl;

or $R^7$ is of the formula R$^d$OC(R$^e$)=CH(C=O)—, R$^f$C(=O)C(=O)—, R$^g$N=C(R$^h$)C(=O)— or R$^i$NHC(R$^j$)=CHC(=O)— wherein R$^d$ is (1–6C)alkyl, R$^e$ is hydrogen or (1–6C)alkyl or R$^d$ and R$^e$ together form a (3–4C)alkylene chain, R$^f$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy, di(1–4C)alkylamino(2–6C)alkoxy, R$^g$ is (1–6C)alkyl, hydroxy or (1–6C)alkyl, R$^h$ is hydrogen or (1–6C)alkyl, R$^i$ is (1–6C)alkyl, phenyl or a 5- or 6-membered heteroaryl and R$^j$ is hydrogen or (1–6C)alkyl;

or $R^7$ is of the formula $R^{14}$CH(R$^{13}$)(CH$_2$)$_m$— wherein m is 0 or 1, $R^{13}$ is fluoro, cyano, (1–4C)alkoxy, (1–4C)alkylsulfonyl, (1–4C)alkoxycarbonyl or hydroxy; (provided that when m is 0, $R^{13}$ is not fluoro or hydroxy) and $R^{14}$ is hydrogen or (1–4C)alkyl;

and pharmaceutically-acceptable salts thereof; except that

N-((5S)-3-4-(2-oxo-5,6-dihydropyran-4-yl)phenyl)-2-oxooxazolidin-5-ylmethyl)acetamide;

N-((5S)-3-3-ethyl-4-(2-oxo-5,6-dihydrothiapyran-4-yl)phenyl)-2-oxooxazolidin-5-ylmethyl)acetamide and N-((5S)-3-(3-hydroxy-4-(2-oxo-1,2,5,6-tetrahydropyrid-4-yl)phenyl)-2-oxooxazolidin-5-ylmethyl)acetamide are excluded.

In a preferred aspect of the invention there is provided a compound of the formula (I) as defined above in the section relating to another aspect of the present invention, except that $R^a$ is hydrogen (rather than hydrogen or (1–4C)alkyl).

In another preferred aspect of the invention there is provided a compound of the formula (I) as defined above in the section relating to another aspect of the present invention, except that in the definition of $R^4$ and $R^5$, neither $R^4$ nor $R^5$ can be oxo (=O).

In a further aspect the present invention provides a compound of the formula (I) wherein:

$R^1$ is of the formula —NHC(=O)(1–4C)alkyl or —NHS(O)$_n$(1–4C)alkyl wherein n is 0, 1 or 2;

$R^2$ and $R^3$ are independently hydrogen or fluoro;

$R^4$ and $R^5$ are independently hydrogen, or methyl;

>A—B— is of the formula >C=CH, >CHCH$_2$ or >C(OH)CH$_2$— (>represents two single bonds)

wherein $R^a$ is hydrogen or (1–4C)alkyl;

D is O, S, SO, SO$_2$ or NR$^7$;

wherein $R^7$ is hydrogen, optionally substituted phenyl, optionally substituted phenyl(1–4C)alkyl, optionally substituted 5- or 6-membered heteroaryl, optionally substituted naphthyl or optionally substituted 5/6 or 6/6 bicyclic heteroaryl ring system wherein the heteroaryl ring systems are joined to the the nitrogen in NR$^7$ by a ring carbon atom;

or $R^7$ is of the formula R$^{10}$CO— or R$^{10}$SO$_2$— wherein $R^{10}$ is amino, (1–4C)alkylamino, di((1–4C)alkyl)amino or (1–6C)alkyl [wherein (1–6C)alkyl is optionally substituted by hydroxy, cyano, amino, or (1–C)alkylS(O)$_q$ wherein q is 1 or 2];

or $R^{10}$ is of the formula R$^{11}$C(O)O(1–6C)alkyl wherein $R^{11}$ is optionally substituted 5- or 6-membered heteroaryl, optionally substututed phenyl or optionally substituted (1–6C)alkyl;

or $R^{10}$ is of the formula R$^{12}$O— wherein $R^{12}$ is optionally substituted (1–6C)alkyl;

or $R^7$ is of the formula R$^{14}$CH(R$^{13}$)(CH$_2$)$_m$— wherein m is 0 or 1, R$^{13}$ is fluoro, cyano, (1–4C)alkoxy, (1–4C)alkylsulfonyl, (1–4C)alkoxycarbonyl or hydroxy; (provided that when m is 0, R$^{13}$ is not fluoro or hydroxy) and R$^{14}$ is hydrogen or (1–4C)alkyl;

and pharmaceutically-acceptable salts thereof.

In the sections above relating to another aspect of the present invention, and to a further aspect of the present invention, '5- or 6-membered heteroaryl' means a 5- or 6-membered aryl ring wherein 1, 2 or 3 of the ring atoms are selected from nitrogen, oxygen and sulfur. Particular examples of such 5- or 6-membered heteroaryl ring systems are imidazole, triazole, pyrimidine, pyridazine, pyridine, isoxazole, oxazole, isothiazole, thiazole and thiophene.

Also, in the sections above relating to another aspect of the present invention, and to a further aspect of the present invention, a '5/6 or 6/6 bicyclic heteroaryl ring system' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Particular examples of 5/6 and 6/6 bicyclic ring systems are benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

Particularly preferred compounds of the invention comprise a compound of the formula (I), or pharmaceutically-acceptable salts thereof, wherein the substituents A, B, D, R$_1$ to R$^{14}$ and other optional substituents mentioned above have the values disclosed hereinbefore, or any of the following values.

(a) Preferably $R^1$ is hydroxy, chloro, fluoro, methanesulfonyloxy, amino, azido, methoxy, methylthio, methylaminocarbonyloxy, or of the formula —NHC(=O)R$^a$ wherein R$^a$ is hydrogen, methoxy, amino, chloromethyl, dichloromethyl, cyanomethyl, methoxymethyl, acetylmethyl, methylamino, dimethylamino or (1–4C)alkyl or $R^1$ is of the formula —NHS(O)$_n$(1–4C)alkyl wherein n is 0, 1 or 2.

(b) More preferably $R^1$ is hydroxy, chloro, fluoro, methanesulfonyloxy, or of the formula —NHC(=O)R$^a$ wherein R$^a$ is hydrogen, methoxy, amino, chloromethyl, dichloromethyl, cyanomethyl, methoxymethyl, acetylmethyl or (1–4C)alkyl or $R^1$ is of the formula —NHS(O)$_n$(1–4C)alkyl wherein n is 0, 1 or 2.

(c) Yet more preferably $R^1$ is hydroxy, or of the formula —NHC(=O)R$^a$ wherein R$^a$ is (1–4C)alkyl or $R^1$ is of the formula —NHS(O)$_n$(1–4C)alkyl wherein n is 0, 1 or 2.

(d) Yet more preferably $R^1$ is of the formula —NHC(=O)(1–4C)alkyl or —NHS(O)$_n$(1–4C)alkyl.

(e) Yet more preferably $R^1$ is of the formula —NHC(=O)(1–4C)alkyl.

(f) Most preferably $R^1$ is acetamido.

(g) In another aspect $R^1$ is hydroxy.

(h) Preferably, at least one of $R^2$ and $R^3$ is hydrogen.

(i) Preferably $R^6$ is hydrogen or (1–4C)alkyl.

(j) Most preferably one of $R^2$ and $R^3$ is hydrogen and the other is fluoro.

(k) Preferably >A—B— is of the formula >C=CH— or >CHCH$_2$—.

(l) Most preferably >A—B— is of the formula >C=CH—.

(m) Preferably $R^4$ and $R^5$ are independently hydrogen, (1–4C)alkyl, carboxy, (1–4C)alkoxycarbonyl, hydroxymethyl, (1–4C)alkoxymethyl or carbamoyl.

(n) More preferably, $R^4$ and $R^5$ are independently hydrogen, AR-oxymethyl or AR-thiomethyl. Especially preferred is AR when it is optionally substituted phenyl, phenyl (1–4C)alkyl, naphthyl, furan, pyrrole, pyrazole, imidazole, triazole, pyrimidine, pyridazine, pyridine, isoxazole, oxazole, isothiazole, thiazole or thiophene.

(o) Most preferably $R^4$ or $R^5$ is hydrogen.

(p) Preferably $R^6$ is hydrogen or (1–4C)alkyl.

(q) More preferably $R^6$ is hydrogen or methyl.

(r) Most preferably $R^6$ is hydrogen.

(s) Preferably D is O, S or of the formula NR$^7$.

(t) Preferably D is O.

(u) Preferred substituents for phenyl and carbon atoms in heteroaryl (mono- and bicyclic) ring systems in R$^7$ and R$^{11}$ include halo, (1–4C)alkyl, hydroxy, nitro, amino, cyano, (1–4C)alkylS(O)$_p$— and (1–4C)alkoxy.

(v) Preferred optional substituents for (1–6C)alkyl in R$^{11}$ are hydroxy, cyano, amino, (1–4C)alkylamino, di((1–4C)alkyl)amino, (1–4C)alkylS(O)$_p$ (wherein p is 1 or 2), carboxy, (1–4C)alkoxycarbonyl, (1–4C)alkoxy, piperazino or morpholino.

(w) Preferred optional substituents for (1–6C)alkyl in R$^{12}$ are hydroxy, (1–4C)alkoxy, cyano, amino, (1–4C)alkylamino, di(C$_{1-2}$alkyl)amino, (1–4C)alkylS(O)$_p^-$ (wherein p is 1 or 2).

(x) Preferably the ring systems in AR are unsubstituted.

(y) Preferably the 5/6 or 6/6 bicyclic ring system in R$^4$, R$^5$, R$^7$ or R$^{10}$ is unsubstituted.

(z) Preferably 5- or 6-membered heteroaryl rings in $R^4$, $R^5$, $R^7$, $R^{10}$ or $R^{11}$ are unsubstituted.

(a1) Preferably 5- or 6-membered heteroaryl in $R^{11}$ is pyridyl or imidazol-1-yl.

(b1) Preferably $R^{12}$ is (1–6C)alkyl. Most preferably $R^{12}$ is tert-butyl or methyl.

(c1) Preferably $R^{13}$ is cyano or fluoro.

(d1) Preferably $R^{14}$ is hydrogen.

(e1) Preferably $R^{10}$ is (1–4C)alkoxycarbonyl, hydroxy(1–4C)alkyl, (1–4C)alkyl, (1–4C)alkylamino, dimethylamino(1–4C)alkyl, (1–4C)alkoxymethyl, (1–4C)alkanoylmethyl, (1–4C)alkanoyloxy(1–4C)alkyl, (1–5C)alkoxy or 2-cyanoethyl.

(f1) More preferably $R^{10}$ is methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl.

(g1) Preferably $R^7$ is hydrogen, cyano, benzyl, pyrimidyl, imidazolyl, triazolyl or of the formula $R^{10}CO-$ or $R^{10}SO_2-$.

(h1) Preferably $R^7$ is hydrogen, cyano, benzyl, methoxycarbonyl, tert-butoxycarbonyl, hydoxyacetyl, dimethylaminoacetyl, acetyloxymethylcarbonyl, methoxyacetyl, methoxalyl, methylcarbamoyl or methanesulfonyl.

(i1) Preferably when $R^{10}$ is benzopyranone it is 4-oxo-benzopyran-2-yl.

(j1) Preferably CY is naphthoxy, especially naphth-1-oxy or naphth-2-oxy.

Therefore, especially preferred compounds of the present invention are of the formula (IB):

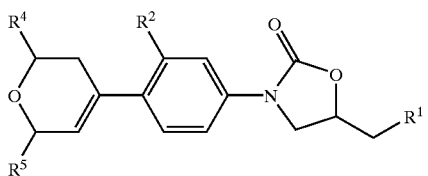

(IB)

wherein $R^1$ is hydroxy or acetamido; $R^2$ is hydrogen or fluoro and $R^4$ and $R^5$ are independently hydrogen, hydroxy, bromo, (1–4C)alkyl, carboxy, (1–4C)alkoxycarbonyl, hydroxymethyl, (1–4C)alkoxymethyl or carbamoyl; and pharmaceutically-acceptable salts thereof.

Of the above especially preferred compounds of the formula (IB), particularly preferred compounds are those wherein $R^1$ is acetamido; $R^2$ is hydrogen or fluoro and $R^4$ and $R^5$ are independently hydrogen, hydroxy, bromo, (1–4C)alkyl, carboxy, (1–4C)alkoxycarbonyl, hydroxymethyl, (1–4C)alkoxymethyl or carbamoyl; and pharmaceutically-acceptable salts thereof.

Further especially preferred compounds of the invention are of the formula (IB) wherein $R^1$ is acetamido; $R^2$ is hydrogen or fluoro and $R^4$ and $R^5$ are independently hydrogen, AR-oxymethyl or AR-thiomethyl (wherein AR is phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene); and pharmaceutically-acceptable salts thereof.

Further, especially preferred compounds of the invention are of the formula (IC):

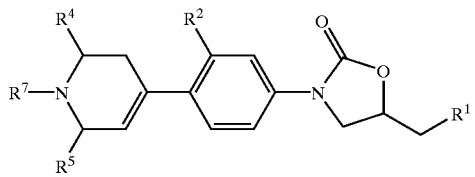

(IC)

wherein $R^1$ is hydroxy or acetamido; $R^2$ is hydrogen or fluoro; $R^4$ and $R^5$ are independently hydrogen, AR-oxymethyl or AR-thiomethyl (wherein AR is phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene), hydroxy, bromo, (1–4C)alkyl, carboxy, (1–4C)alkoxycarbonyl, hydroxymethyl, (1–4C)alkoxymethyl or carbamoyl and $R^7$ is cyano, pyrimidin-2-yl, tetrazol-5-yl, 2-cyanoethenyl, 2-cyano-2-((1–4C)alkyl)ethenyl or $R^7$ is of the formula $R^{10}CO-$ or $R^{10}SO_2-$ (wherein $R^{10}$ is hydrogen, (1–4C)alkyl [optionally substituted by hydroxy, (1–4C)alkoxy, (1–4C)alkylS(O)$_q$, (1–4C)alkylamino, (1–4C)alkanoyl, naphthoxy, (2–6C)alkanoylamino or (1–4C)alkylS(O)$_p$NH— wherein p is 1 or 2 and q is 0, 1 or 2], phenyl, naphthyl, imidazole, triazole, pyrimidine, pyridazine, pyridine, isoxazole, oxazole, isothiazole, thiazole, thiophene, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline or naphthyridine, or $R^{10}$ is of the formula $R^{11}C(O)O(1–6C)$ alkyl wherein $R^{11}$ is (1–6C)alkyl), or $R^7$ is of the formula $R^fC(=O)C(=O)-$ wherein $R^f$ is (1–6C)alkoxy; and pharmaceutically-acceptable salts thereof.

Of the above especially preferred compounds of the invention of the formula (IC), particularly preferred compounds are those wherein $R^1$ is acetamido; $R^2$ is hydrogen or fluoro; $R^4$ and $R^5$ are independently hydrogen, AR-oxymethyl or AR-thiomethyl [wherein AR is phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene], hydroxymethyl, (1–4C)alkoxymethyl or carbamoyl and $R^7$ is cyano, pyrimidin-2-yl, tetrazol-5-yl, 2-cyanoethenyl, 2-cyano-2-((1–4C)alkyl)ethenyl, or $R^7$ is of the formula $R^{10}CO-$ or $R^{10}SO_2-$ (wherein $R^{10}$ is hydrogen, (1–4C)alkyl [optionally substituted by hydroxy, (1–4C)alkylS(O)$_q$, (1–4C)alkanoyl or naphthoxy wherein q is 0, 1 or 2], phenyl, naphthyl, imidazole, triazole, pyrimidine, pyridazine, pyridine, isoxazole, oxazole, isothiazole, thiazole, thiophene, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline or naphthyridine, or $R^{10}$ is of the formula $R^{11}C(O)O(1–6C)$ alkyl wherein $R^{11}$ is (1–6C)alkyl), or $R^7$ is of the formula $R^fC(=O)C(=O)-$ wherein $R^f$ is (1–6C)alkoxy; and pharmaceutically-acceptable salts thereof.

Of the above particularly preferred compounds of the invention of the formula (IC), especially preferred compounds are those wherein $R^1$ is acetamido; $R^2$ is hydrogen or fluoro; $R^4$ and $R^5$ are hydrogen and $R^7$ is cyano, pyrimidin-2-yl, tetrazol-5-yl, 2-cyanoethenyl, 2-cyano-2-((1–4C)alkyl)ethenyl, or $R^7$ is of the formula $R^{10}CO-$ or $R^{10}SO_2-$ (wherein $R^{10}$ is hydrogen, (1–4C)alkyl [optionally substituted by hydroxy, (1–4C)alkylS(O)$_q$ or (1–4C)alkanoyl wherein q is 0, 1 or 2], phenyl, naphthyl, imidazole, triazole, pyrimidine, pyridazine, pyridine, isoxazole, oxazole, isothiazole, thiazole, thiophene, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline or naphthyridine, or $R^{10}$ is of the formula $R^{11}C(O)O(1-6C)$ alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Of the above particularly preferred compounds of the invention of the formula (IC), further especially preferred compounds are those wherein $R^1$ is acetamido; $R^2$ is hydrogen or fluoro; $R^4$ and $R^5$ are independently hydrogen, AR-oxymethyl or AR-thiomethyl (wherein AR is phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene), hydroxymethyl, (1–4C)alkoxymethyl or carbamoyl and $R^7$ is cyano, pyrimidin-2-yl, tetrazol-5-yl, 2-cyanoethenyl, 2-cyano-2-((1–4C)alkyl)ethenyl, or $R^7$ is of the formula $R^{10}CO$— (wherein $R^{10}$ is hydrogen, (1–4C)alkyl [optionally substituted by hydroxy, (1–4C)alkylS(O)$_q$ or (1–4C)alkanoyl wherein q is 0, 1 or 2], phenyl, naphthyl, imidazole, triazole, pyridine, pyridazine, pyridine, isoxazole, oxazole, isothiazole, thiazole, thiophene, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline or naphthyridine, or $R^{10}$ is of the formula $R^{11}C(O)O(1-6C)$alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Of the above particularly preferred compounds of the invention of the formula (IC), chiefly preferred compounds are those wherein $R^1$ is acetamido; $R^2$ is hydrogen or fluoro; $R^4$ and $R^5$ are independently hydrogen, AR-oxymethyl or AR-thiomethyl (wherein AR is phenyl, phenyl(1–4C)alkyl, naphthyl, furan, pyrrole, pyrazole, imidazole, triazole, pyrimidine, pyridazine, pyridine, isoxazole, oxazole, isothiazole, thiazole or thiophene), hydroxymethyl, (1–4C) alkoxymethyl or carbamoyl and $R^7$ is cyano, pyrimidin-2-yl, tetrazol-5-yl, 2-cyanoethenyl, 2-cyano-2-((1–4C)alkyl)ethenyl, or $R^7$ is of the formula $R^{10}SO_2$— (wherein $R^{10}$ is hydrogen, (1–4C)alkyl [optionally substituted by hydroxy, (1–4C)alkylS(O)$_q$ or (1–4C)alkanoyl wherein q is 0, 1 or 2], phenyl, naphthyl, imidazole, triazole, pyrimidine, pyridazine, pyridine, isoxazole, oxazole, isothiazole, thiazole, thiophene, benzofan, benzoimidazole, benzothiophene, benzisothiazole, benzoxazole, benzisoxazole, pyridoimidazole, pyrimidoimidazole, quinoline, quinoxaline, quinazoline, phthalazine, cinnoline or naphthyridine, or $R^{10}$ is of the formula $R^{11}C(O)O(1-6C)$alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Of the above further especially preferred compounds of the invention of the formula (IC), particular especially preferred compounds are those wherein $R^1$ is acetamido; $R^2$ is hydrogen or fluoro; $R^4$ and $R^5$ are hydrogen; and $R^7$ is pyrimidin-2-yl, 2-cyanoethenyl, 2-cyano-2-((1–4C)alkyl)ethenyl, or $R^7$ is of the formula $R^{10}CO$— (wherein $R^{10}$ is hydrogen or (1–4C)alkyl [optionally substituted by hydroxy or (1–4C)alkylS(Q)$_q$ wherein q is 0, 1 or 2], or $R^{10}$ is of the formula $R^{11}C(O)O(1-6C)$alkyl wherein $R^{11}$ is (1–6C)alkyl), or $R^{11}$ is of the formula $R^fC(=O)C(=O)$— wherein $R^f$ is (1–6C)alkoxy; and pharmaceutically-acceptable salts thereof.

Of the above chiefly preferred compounds of the invention of the formula (IC), particular chiefly preferred compounds are those wherein $R^1$ is acetamido; $R^2$ is hydrogen or fluoro; $R^4$ and $R^5$ are hydrogen; and $R^7$ is pyrimidin-2-yl, 2-cyanoethenyl, 2-cyano-2-((1–4C)alkyl)ethenyl, or $R^7$ is of the formula $R^{10}SO_2$— (wherein $R^{10}$ is hydrogen or (1–4C)alkyl [optionally substituted by hydroxy or (1–4C)alkylS(O)$_q$ wherein q is 0, 1 or 2], or $R^{10}$ is of the formula $R^{11}C(O)O(1-6C)$alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Of the above particular especially preferred compounds of the invention of the formula (IC), the most preferred are those wherein $R^1$ is acetamido; $R^2$ is hydrogen or fluoro; $R^4$ and $R^5$ are hydrogen; and $R^7$ is pyrimidin-2-yl, or $R^7$ is of the formula $R^{10}CO$— (wherein $R^{10}$ is hydrogen or (1–4C)alkyl [optionally substituted by hydroxy or (1–4C)alkylS(O)$_q$ wherein q is 0, 1 or 2], or $R^{10}$ is of the formula $R^{11}C(O)O(1-6C)$alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Of the above particular chiefly preferred compounds of the invention of the formula (IC), the most preferred are those wherein $R^1$ is acetamido; $R^2$ is hydrogen or fluoro; $R^4$ and $R^5$ are hydrogen; and $R^7$ is pyrimidin-2-yl, or $R^7$ is of the formula $R^{10}SO_2$— (wherein $R^{10}$ is hydrogen or (1–4C)alkyl [optionally substituted by hydroxy or (1–4C)alkylS(O)$_q$ wherein q is 0, 1 or 2], or $R^{10}$ is of the formula $R^{11}C(O)O(1-6C)$alkyl wherein $R^{11}$ is (1–6C)alkyl), or $R^7$ is of the formula $R^fC(=O)C(=O)$— wherein $R^f$ is (1–6C)alkoxy; and pharmaceutically-acceptable salts thereof.

Particular compounds of the present invention are:

N-((5S)-3-(4-(1-tertbutoxycarbonyl-1,2,5,6-tetrahydropyrid-4-yl)phenyl)-2-oxooxazolidin-5-ylmethyl)acetamide;

N-((5S)-3-(4-(1,2,5,6-tetrahydropyrid-4-yl)phenyl)-2-oxooxazolidin-5-ylmethyl)acetamide;

N-((5S)-3-(4-(1-methoxycarbonyl-1,2,5,6-tetrahydropyrid-4-yl)phenyl)-2-oxooxazolidin-5-ylmethyl)acetamide;

N-((5S)-3-(4-(1-methylsulfonyl-1,2,5,6-tetrahydropyrd-4-yl)phenyl)-2-oxooxazoidin-5-ylmethyl)acetamide;

N-((5S)-3-(4-(1-hydroxyacetyl-1,2,5,6-tetrahydropyrid-4-yl)phenyl)-2-oxooxazolidin-5-ylmethyl)acetamide;

N-((5S)-3-(4-(1-dimethylaminoacetyl-1,2,5,6-tetrahydropyrid-4-yl)phenyl)-2-oxooxazolidin-5-ylmethyl)acetamide;

N-((5S)-3-(4-(2,3-dihydropyran-4-yl)-phenyl)-2-oxooxazolidin-5-ylmethyl)acetamide;

N-((5S)-3-(4-(2,3-dihydrothiapyran-4-yl)phenyl)-2-oxooxazolidin-5-ylmethyl)acetamide;

N-((5S)-3-(4-(2,3-dihydrooxothiapyran-4-yl)phenyl)-2-oxooxazolidin-5-ylmethyl)acetamide;

N-((5S)-3-(4-(2,3-dihydrooxothiapyrany-4-yl)phenyl)-2-oxooxazolidin-5-ylmethyl)acetamide;

N-((5S)-3-(3-fluoro-4-(1-benzyl-1,2,5,6-tetrahydropyrid-4-yl)phenyl)-2-oxooxazolidin-5-ylmethyl)acetamide;

N-((5S)-3-(3-fluoro-4-(1,2,5,6-tetrahydropyrid-4-yl)phenyl)-2-oxo-oxazolidin-5-ylmethyl)acetamide;

N-((5S)-3-(3-fluoro-4-(1-tertbutoxycarbonyl-1,2,5,6-tetrahydropyrid-4-yl)phenyl)-2-oxo-5-oxazolidinylmethyl)acetamide;

N-((5S)-3-(3-fluoro-4-(1-methoxycarbonyl-1,2,5,6-tetrahydropyrid-4-yl)phenyl)-2-oxooxazolidin-5-ylmethyl)acetamide;

N-((5S)-3-(3-fluoro-4-(1-methylsulfonyl-1,2,5,6-tetrahydropyrid-4-yl)phenyl)-2-oxooxazolidin-5-ylmethyl)acetamide;

N-((5S)-3-(3-fluoro-4-(1-hydroxyacetyl-1,2,5,6-tetrahydropyrid-4-yl)phenyl)-2-oxooxazolidin-5-ylmethyl)acetamide;
N-((5S)-3-(3-fluoro-4-(1-dimethylaminoacetyl-1,2,5,6-tetrahydropyrid-4-yl)phenyl)-2-oxooxazolidin-5-ylmethyl)acetamide;
N-((5S)-3-(3-fluoro-4-(2,3-dihydropyranyl)-phenyl)-2-oxooxazolidin-5-ylmethyl)acetamide;
N-((5S)-3-(3-fluoro-4-(2,3-dihydrothiapyran-4-yl)phenyl)-2-oxooxazolidin-5-ylmethyl)acetamide;
N-((5S)-3-(3-fluoro-4-(2,3-dihydrooxothiapyran-4-yl)phenyl)-2-oxooxazolidin-5-ylmethyl)acetamide;
N-((5S)-3-(4-(2,3-dihydrodioxothiapyrany-4-yl)phenyl)-2-oxooxazolidin-5-ylmethyl)acetamide;
N-((5S)-3-(4-(1-(pyrimidin-2-yl)-1,2,5,6-tetrahydropyrid-4-yl)phenyl)-2-oxooxazolidin-5-ylmethyl)acetamide;
5N-((5S)-3-(4-(1-cyano-1,2,5,6-tetrahydropyrid-4-yl)phenyl)-2-oxooxazolidin-5-ylmethyl)acetamide;
N-((5S)-3-(3-fluoro-4-(1-(acetoxyacetyl-1,2,5,6-tetrahydropyrid-4-yl)phenyl)-2-oxooxazolidin-5-ylmethyl)acetamide;
5R-hydroxymethyl-3-(3-fluoro-4-(1-benzyl-1,2,5,6-tetrahydropyrid-4-yl)phenyl)oxazolidin-2-one;
N-((5S)-3-(3-fluoro-4-(1-(pyrimidin-2-yl)-1,2,5,6-tetrahydropyrid-4-yl)phenyl)-2-oxooxazolidin-5-ylmethyl)acetamide;
N-((5S)-3-(3-fluoro-4-(1-cyano-1,2,5,6-tetrahydropyrid-4-yl)phenyl)-2-oxooxazolidin-5-ylmethyl)acetamide;
N-((5S)-3-(3-fluoro-4-(1-methoxyacetyl-1,2,5,6-tetrahydropyrid-4-yl)phenyl)-2-oxooxazolidin-5-ylmethyl)acetamide;
N-((5S)-3-(3-fluoro-4-(1-methoxalyl-1,2,5,6-tetrahydropyrid-4-yl)phenyl)-2-oxooxazolidin-5-ylmethyl)acetamide;
N-((5S)-3-(3-(3-fluoro-4-(1-(N-methylcarbamoyl)-1,2,5,6-tetrahydropyrid-4-yl)phenyl)-2-oxooxazolidin-5-ylmethyl)acetamide;
and pharmaceutically-acceptable salts thereof.

Other particular compounds of the present invention are

N-((5S)-3-(4-(1-(2-cyano-2-methylethenyl)-1,2,5,6-tetrahydropyrid-4-yl)phenyl)-2-oxo-oxazolidin-5-ylmethyl)acetamide;
N-((5S)-3-(4-(1-(hydroxymethylsulfonyl)-1,2,5,6-tetrahydropyrid-4-yl)phenyl)-2-oxo-oxazolidin-5-ylmethyl)acetamide;
N-((5S)-3-(4-(1-(methylsulfonylaminomethylcarbonyl)-1,2,5,6-tetrahydropyrid-4-yl)phenyl)-2oxo-oxazolidin-5-ylmethyl)acetamide;
and pharmaceutically-acceptable salts thereof.

Particularly preferred compounds of the present invention are:
N-((5S)-3-(4-(1-methylsulfonyl-1,2,5,6-tetrahydropyrid-4-yl)phenyl)-2-oxo-oxazolidin-5-ylmethyl)acetamide;
N-((5S)-3-(4-(1-acetyloxymethylcarbonyl-1,2,5,6-tetrahydropyrid-4-yl)phenyl)-2-oxooxazolidin-5-ylmethyl)acetamide;
N-((5S)-3-(4-(1-hydroxyacetyl-1,2,5,6-tetrahydropyrid-4-yl)phenyl)-2-oxooxazolidin-5-ylmethyl)acetamide;
N-((5S)-3-(3-fluoro-4)-acetyloxymethylcarbonyl-1,2,5,6-tetrahydropyrid-4-yl)phenyl)-2-oxooxazolidin-5-ylmethyl)acetamide;
N-((5S)-3-(3-fluoro-4-(1-hydroxyacetyl-1,2,5,6-tetrahydropyrid-4-yl)phenyl)-2-oxooxazolidin-5-ylmethyl)acetamide;
N-((5S)-3-(4-(2,3-dihydro-6H-pyran-4-yl)phenyl)-2-oxooxazolidin-5-ylmethyl)acetamide;
N-((5S)-3-(3-fluoro-4-(2,3-dihydro-6H-pyran-4-yl)phenyl)-2-oxooxazolidin-5-ylmethyl)acetamide;
N-((5S)-3-(3-fluoro-4-(1-{pyrimid-2-yl}-1,2,5,6-tetrahydropyrid-4-yl)phenyl)-2-oxooxazolidin-5-ylmethyl)acetamide;
N-((5S)-3-(3-fluoro-4-(1-methylsulfonyl-1,2,5,6-tetrahydropyrid-4-yl)phenyl)-2-oxooxazolidin-5-ylmethyl)acetamide;
N-((5S)-3-(4-(1-{pyrimid-2-yl}-1,2,5,6-tetrahydropyrid-4-yl)phenyl)-2-oxooxazolidin-5-ylmethyl)acetamide;
N-((5S)-3-(3-fluoro-4-(1-acetoacetyl-1,2,5,6-tetrahydropyrid-4-yl)phenyl)-2-oxooxazolidin-5-ylmethyl)acetamide;
N-((5S)-3-(4-(-(naphth-2-ylsulfonyl)-1,2,5,6-tetrahydropyrid-4yl)phenyl)-2-oxooxazolidin-5-ylmethyl)acetamide;
N-((5S)-3-(4-(1-(naphth-2-oxyacetyl)-1,2,5,6-tetrahydropyrid-4-yl)phenyl)-2-oxooxazolidin-5-ylmethyl)acetamide;
N-((5S)-3-(4-(1-methylthioacetyl)-1,2,5,6-tetrahydropyrid-4-yl)phenyl)-2-oxooxazo -ylmethyl)acetamide;
and pharmaceutically-acceptable salts thereof.

Especially preferred compounds of the invention are:

N-((5S)-3-(4-(1-methylsulfonyl-1,2,5,6-tetrahydropyrid-4-yl)phenyl)-2-oxo-oxazolidin-5-ylmethyl)acetamide;
N-((5S)-3-(4-(1-acetyloxymethylcarbonyl-1,2,5,6-tetrahydropyrid-4-yl)phenyl)-2-oxooxazolidin-5-ylmethyl)acetamide;
N-((5S)-3-(4-(1-hydroxyacetyl-1,2,5,6-tetrahydropyrid-4-yl)phenyl)-2-oxooxazolidin-5-ylmethyl)acetamide;
N-((5S)-3-(3-fluoro-4-(1-acetyloxymethylcarbonyl-1,2,5,6-tetrahydropyrid-4-yl)phenyl)-2-oxooxazolidin-5-ylmethyl)acetamide;
N-((5S)-3-(3-fluoro-4-(1-hydroxyacetyl-1,2,5,6-tetrahydropyrid-4-yl)phenyl)-2-oxooxazolidin-5-ylmethyl)acetamide;
N-((5S)-3-(4-(2,3-dihydro-6H-pyran-4-yl)phenyl)-2-oxooxazolidin-5-ylmethyl)acetamide;
N-((5S)-3-(3-fluoro-4-2,3-dihydro-6H-pyran-4-yl)phenyl)-2-oxooxazolidin-5-ylmethyl)acetamide;
and pharmaceutically-acceptable salts thereof.

Other especially preferred compounds of the invention are:

N-((5S)-3-(3-fluoro-4-(1-{pyrimid-2-yl}-1,2,5,6-tetrahydropyridyl)phenyl)-2-oxooxazolidin-5-ylmethyl)acetamide;
N-((5S)-3-(3-fluoro-4-(1-methylsulfonyl-1,2,5,6-tetrahydropyrid-4-yl)phenyl)-2-oxooxazolidin-5-ylmethyl)acetamide;
N-((5S)-3-(4-(1-{pyrimid-2-yl}-1,2,5,6-tetrahydropyrid-4-yl)phenyl)-2-oxooxazolidin-5-ylmethyl)acetamide;
N-((5S)-3-(3-fluoro-4-(1-acetoacetyl-1,2,5,6-tetrahydropyrid-4-yl)phenyl)-2-oxooxazolidin-5-ylmethyl)acetamide;
N-((5S)-3-(4(1-naphth-2-ylsulfonyl)-1,2,5,6-tetrahydropyrid-4-yl)phenyl)-2-oxooxazolidin-5-ylmethyl)acetamide;
N-((5S)-3-(4-(1-(naphth-2-oxyacetyl)-1,2,5,6-tetrahydropyrid-4-yl)phenyl)-2-oxooxazolidin-5-ylmethyl)acetamide;

N-((5S)-3-(4-(1-(methylthioacetyl)-1,2,5,6-tetrahydropyrid-4-yl)phenyl)-2-oxooxazolidin-5-ylmethyl)acetamide;
and pharmaceutically-acceptable salts thereof.

In a further aspect the present invention provides a process for preparing a compound of formula (I) or a pharmaceutically-acceptable salt thereof. The compounds of formula (I) may be prepared by deprotecting a compound of formula (II):

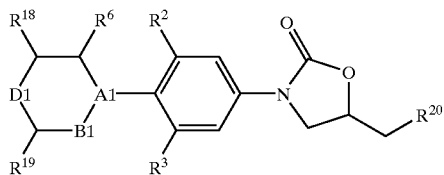

(II)

wherein $R^2$, $R^3$ and $R^6$ are as hereinabove defined, $R^{18}$ is $R^4$ or protected $R^4$, $R^{19}$ is $R^5$ or protected $R^5$, $R^{20}$ is $R^1$ or protected $R^1$, >A1—B1— is >A—B— or protected >A—B— and D1 is D in which functional groups are optionally protected; and thereafter, if necessary, forming a pharmaceutically-acceptable salt.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. allyl and vinylethyl).

Methods particularly appropriate for the removal of carboxyl protecting groups, include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, metal- or enzymically-catalysed hydrolysis, for groups such as o-nitrobenzyloxycarbonyl, photolytically and for groups such as silyl groups, fluoride.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4alkoxybenzyl (e.g. 4-methoxybenzyl); 2,4di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by cataltytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II) and pharmaceutically-acceptable salts thereof can be prepared:

(a) by modifying a substituent in or introducing a substituent into another compound of formula (I) or (II);

(b) when $R^1$ or $R^{20}$ is of the formula —NHS(O)$_n$(1–4C) alkyl, wherein n is 1 or 2, by oxidising a compound of the formula (I) or (II) wherein n is 0 or, when n is 2 by oxidising a compound of the formula (I) or (II) wherein n is 1;

(c) when $R^1$ or $R^{20}$ is of the formula —NHC(=O)$R^b$ or NHS(O)$_n$(1–4C)alkyl, introducing the group —C(=O)$R^b$ or —S(O)$_n$(1–4C)alkyl into a compound of the formula (III);

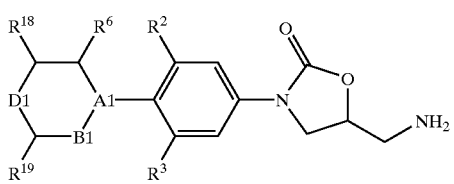

(III)

(d) when $R^1$ or $R^{20}$ is hydroxy, by reacting a compound of the formula (V) with a compound of formula (VI):

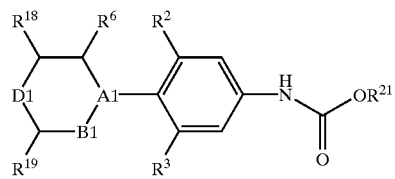

(V)

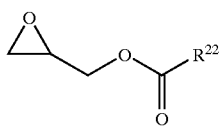

(VI)

(e) when >A1—B1— is >C=CR$^{a1}$—, by reacting a compound of the formula (VII) with a compound of the formula (VIII):

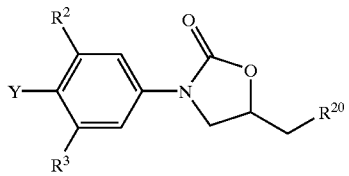

(VII)

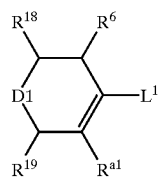

(VIII)

(f) when >A1—B1— is >CHCH(R$^{a1}$)—, by catalytic hydrogenation of a compound of the formula (I) or (II) wherein >A1—B1— is >C=CR$^{a1}$—;

(g) when >A1—B1— is >C=CR$^{a1}$—, by elimination of the elements of water, or HOCOR$^{23}$, or HOSO$_2$ R$^{24}$ from a compound of the formula (IX) (ie. when R$^{25}$ is —H, —COR$^{23}$ or —SO$_2$R$^{24}$).

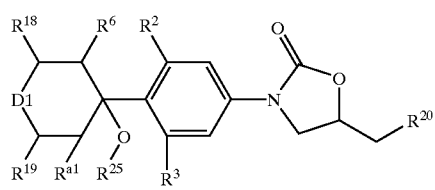

(IX)

(h) when D is NR$^7$ and R$^7$ is R$^{10}$OC— or R$^{10}$S(O)$_n$—, wherein n is 2, by reaction of a compound of formula (X) with a compound of the formula (XI) or (XII), wherein n is 2:

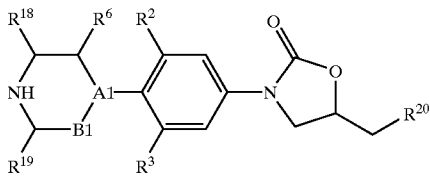

(X)

R$^{10}$COL$^2$ (XI)

R$^{10}$SO$_n$L$^2$ (XII)

(i) when $R^1$ or $R^{20}$ is azido, by reacting a compound of the formula (XIII) with a source of azide:

(XIII)

(j) when $R^1$ or $R^{20}$ is amino, by reducing a compound of the formula (I) or (II) wherein $R^1$ or $R^{20}$ azido;

(k) when $R^1$ or $R^{20}$, is chloro, fluoro, (1–4C)alkanesulfonyloxy, or (1–4C)alkylaminocarbonyloxy, or $R^{20}$ is of the formula —N(CO$_2$R$^{27}$)CO(1–4C)alkyl; from a compound of the formula (I) and (II) wherein $R^1$ or $R^{20}$ is hydroxy; or (l) when $R^1$ or $R^{20}$ is chloro, (1–4C)alkylthio or (1–4C)alkoxy, from a compound of the formula (XIII);

wherein R$^2$, R$^3$, R$^6$ and R$^{20}$ are as hereinabove defined; R$^{a1}$ is R$^a$ or protected R$^a$; R$^{21}$ is (1–6C)alkyl or benzyl; R$^{22}$ is of the formula (1–4C)alkyl or —S(O)$_n$(1–4C)alkyl; R$^{23}$ is (1–4C)alkyl; R$^{24}$ is an optionally substituted phenyl group: R$^{25}$ is hydrogen, —COR$^{23}$ or —SO, R$^{24}$; R$^{26}$ is mesyloxy or tosyloxy; R$^{27}$ is (1–4C) alkyl or benzyl; n is 0, 1 or 2 unless otherwise stated above: L$^1$ is an iodo or triflate leaving group; L$^2$ is a leaving group, such as, for example, hydroxy or chloro; and Y is a trialkyltin residue or a boronate acid or ester residue;

and thereafter if necessary:
i) removing any protecting groups;
ii) forming a pharmaceutically-acceptable salt.

Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example. Tet.Lett., 585, 1972), a carbonyl group converted to a thiocarbonyl group (e.g. using Lawsson's reagent) or a bromo group converted to an alkylthio group.

Compounds of the formula (I) or (II) wherein $R^1$ or $R^{20}$ is —NHS(O)$_n$(1–4C)alkyl can be prepared by oxidising a compound of the formula (I) or (II) with standard reagents known in the art for the oxidation of a thio group to a sulfinyl or sulfonyl group. For example, a thio group may be oxidised to a sulfinyl group with a peracid such as m-chloroperoxybenzoic acid and oxidising agents such as potassium permanganate can be used to convert a thio group to a sulfonyl group. Compounds of the formula (I) or (II) wherein $R^1$ or $R^{20}$ is —NHS(1–4C)alkyl can be prepared by reacting compounds of the formula (III) with a reagent such as (1–4C)alkylSCl.

When $R^b$ is (1–4C)alkyl, the group —C(=O)(1–4C)alkyl may be introduced into a compound of the formula (III) by standard acetylation procedures. For example, the amino group may be acetylated to give an acetamido group using the Schotten-Baumann procedure i.e. reacting the compound of the formula (I) or (II) wherein $R^1$ or $R^{20}$ is amino with acetic anhydride in aqueous sodium hydroxide and THF in a temperature range of 0° C. to ambient temperature. Preferably the acylation is carried out in situ following the catalytic hydrogenation of a compound of the formula (I) or (II) wherein $R^1$ or $R^{20}$ is azido, by performing the hydrogenation in the presence of acetic anhydride.

When $R^b$ is hydrogen, the —CHO group may be introduced into the compound of the formula (III) by reacting the latter compound with formic acetic anhydride, in an inert organic solvent such as THF, in a temperature range of 0° C. to ambient temperature, or by reacting it with ethyl formate in an inert organic solvent in the temperature range of 50–100° C.

When $R^b$ is (1–4C)alkoxy, the —COO(1–4C)alkyl group may be introduced into the compound of the formula (III) by reacting the latter compound with (1–4C)alkyl chloroformate, in the presence of an organic base such as triethylamine, in an organic solvent such as dichloromethane and in a temperature range of 0° C. to ambient temperature.

When $R^b$ is amino, the —CONH$_2$ group may be introduced into the compound of the formula (III) by reacting the latter compound either with potassium cyanate in aqueous acid (e.g. hydrochloric acid) in a temperature range of ambient temperature to 40° C. or with phenyl carbamate in glyme at reflux.

When $R^b$ is chloromethyl, dichloromethyl, cyanomethyl or methoxymethyl, the —C(=O)$R^b$ group may be introduced into the compound of the formula (III) by reacting the latter compound with the appropriate acid chloride under standard conditions. The acid chloride may be prepared from the appropriate acid. When $R^b$ is acetylmethyl, the —C(=O)$R^b$ group may be introduced into the amino compound by reacting the latter compound with diketene, in an inert organic solvent such as THF, in a temperature range of 0° C. to ambient temperature.

Alternatively, the compound of the formula (III) may be reacted with the appropriate acid anhydride, in dichloromethane or THF, in the presence of an organic base such as triethylamine and in a temperature range of 0° C. to ambient temperature, or the amino compound may be reacted with the appropriate acid in the presence of 1-(3-dimethylaminopropyl)-3-ethylcarbodiimide hydrochloride and an organic base such as triethylamine, in an organic solvent such as dichloromethane, in a temperature range of 0° C. to ambient temperature.

When $R^b$ is methylamino, the —CONHMe group may be introduced into the compound of the formula (III) by reacting the latter compound with methyl isocyanate in an organic solvent such as THF or acetonitrile, in a temperature range of 0° C. to ambient temperature.

When $R^b$ is dimethylamino, the —CONMe$_2$ group may be introduced into the compound by of the formula (III) by reacting the latter compound with dimethylcarbamoyl chloride and triethylamine in an organic solvent such as THF or acetonitrile, in a temperature range of 0° C. to ambient temperature.

Standard reaction conditions for the conversion of a compound of the formula (III) to a compound of the formula (I) or (II) wherein $R^1$ or $R^{20}$ is sulfonamido are known in the art. For example, a compound of the formula (III) could be converted to a compound of the formula (I) or (II) wherein $R^1$ or $R^{20}$ is (1–4C)alkylSO$_2$NH— by reacting the former compound with a sulfonyl chloride, for example, mesyl chloride, in a mild base such as pyridine or triethylamine.

Alternatively compounds of the formula (I) or (II) wherein $R^1$ or $R^{20}$ is (1–4C)alkylSO$_2$NH— or (1–4C)alkylSONH— may be prepared by reacting a compound of the formula (III) with a compound of the formula (IV):

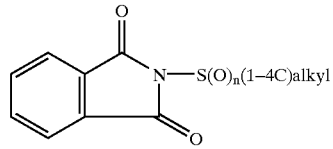

(IV)

The compound of the formula (IV) may be prepared by oxidising a compound of the formula (IVA):

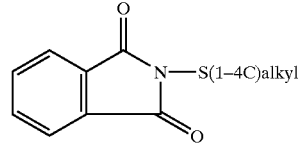

(IVA)

with standard oxidising agents known for the conversion of a thio group to a sulfinyl or sulfonyl group.

Compounds of the formula (IVA) can be prepared by reacting phthalimide with an alkylthiochloride((1–4C) alkylSCl).

A compound of the formula (III) may be prepared as described in process (j).

Compounds of the formulae (V) and (VI) are conveniently reacted together in the presence of a strong base such as butyl lithium, lithium hexamethyldisilazide sodium hydride, or lithium diisopropylamide. The reaction is conveniently carried out in an inert solvent such as tetrahydrofuran (THF), dimethylformamide (DMF), N,N$^1$-dimethylpropyleneurea (DMPU) or N-methylpyrrolidone in a temperature range of −78° C. to −50° C. for the deprotonation and cyclisation. Suitable values for $R^{21}$ include ethyl, butyl and benzyl and suitable values for $R^{22}$ include ethyl and n-propyl, preferably n-propyl.

A compound of the formula (V) is conveniently prepared by reacting a chloroformate of the formula (ClCOOR$^{21}$) with a compound of the formula (VA):

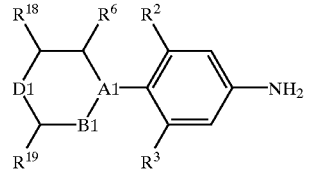

(VA)

wherein R²–R⁵ and >A1—B1— are as hereinabove defined. The reaction is conveniently carried out in the presence of an inorganic or organic base such as sodium bicarbonate or an amine base such as dimethylaniline, the former in a solvent such as acetone/water and the latter in an organic solvent such as THF, toluene, DMF or acetonitrile.

A compound of the formula (VA) wherein >A1—B1— is >C=CH—, may be prepared by reacting a compound of the formula (VIII) with a compound of the formula (VB).

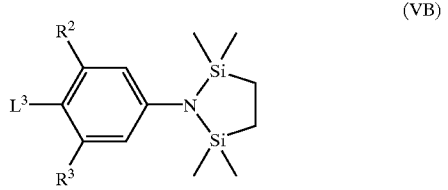

(VB)

The reaction between compounds of the formulae (VIII) and (VB) wherein L³ is bromo or iodo may be is carried out by treating (VB) with an organolithium species such as 1-butyl methyl in an inert solvent such as THF at a low temperature, such as −78° C., followed by the addition of an anhydrous zinc halide such as zinc chloride, in a temperature range of 0° C. to ambient temperature, to generate the organozinc chloride (VB), wherein L¹ is ZnCl. Treatment of the organozinc chloride in situ with a compound of the formula (VIII) followed by a suitable palladium [0] catalyst such as Pd(PPh₃)₄, in the temperature range of 0° C. to ambient temperature, results in the cross-coupled product (VA) after brief treatment with dilute acid to hydrolyse the 'stabase' protected amine.

A compound of the formula (VB) may be prepared by treatment of p-iodo or p-bromoaniline with the 'stabase' reagent (1,2-bis(chlorodimethylsilyl)ethane) in the presence of an organic base such as triethylamine.

The reaction between compounds of the formulae (VII) and (VIII), wherein Y is trialkyltin and L¹ is triflate is conveniently carried out in the presence of a palladium (0) catalyst such as Pd(PPh₃)₄ or Pd(dba)₃ in a temperature range of 0–115° C. Preferably the trialkyltin group is trimethyltin. A suitable value for L¹ is iodo or trifluoromethylsulfonyloxy.

When Y is a boronate acid or ester, the reaction may be carried out under conditions known for the Suzuki reaction i.e. in the presence of a palladium (0) catalyst such as Pd(PPh₃)₄ or Pd(dba)₃, in a water-miscible organic solvent such as dimethylformamide or 1,2-dimethoxyethane and in the presence of a mild base such as sodium acetate or sodium bicarbonate which is added in water. The reaction is then heated to 80° C. Alternatively, silver oxide may be used in place of the base, in which case the reaction may be carried out at a lower temperature. When Y is a boronate ester, preferably L¹ is iodo. Suitable boronate esters include lower alkyl and cyclic boronate esters.

A compound of the formula (VII) wherein Y is trimethylstannyl may be prepared by methods known in the art (for example by using methods similar to those described in Patent Application No. WO 9413649 from a compound of the formula (VII) wherein Y is iodo or bromo). Alternatively compounds of the formula (VII) wherein Y is a cyclic boronate ester as in (VIIA):

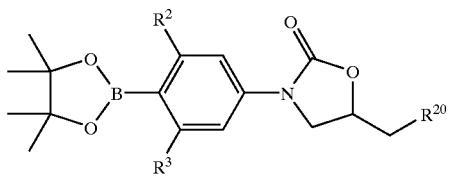

(VIIA)

may be prepared from a compound of the formula (VII) wherein Y is iodo or bromo, by sequential treatment with a suitable Pd catalyst such as PdCl₂(dppf), potassium acetate and the pinacol ester of diboron in a polar solvent such as DMSO (for example see J.Org.Chem., 1995, 60 7508–7510).

A compound of the formula (VII), wherein Y is iodo may be prepared by reacting a compound of the formula (VIIB) with iodine monochloride in the presence of trifluoroacetic acid or with iodine and silver triflate:

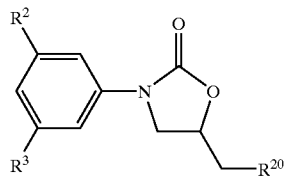

(VIIB)

When Y is bromo, a compound of the formula (VII) may be prepared by brominating a compound of the formula (VIIB) using standard bromination methods. For example, by reacting a compound of the formula (VIIB) with N-bromosuccinimide or bromine.

A compound of the formula (VIIB) may be prepared by forming the oxazolidinone ring from the amino group of a compound of the formula (VIC) using a similar method to that described for the preparation of a compound of the formula (I) or (II) from a compound of the formula (VA):

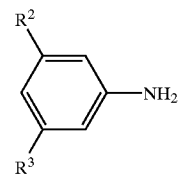

(VIIC)

The resulting compound of the formula (VIIB) in which R²⁰ is hydroxy may be converted to other compounds of the formula (VIIB) using similar methods to those described for the formation of a compound of the formula (I) or (II) from a compound of the formula (I) or (II) wherein R¹ or R²⁰ is hydroxy, via a compound of the formula (III).

A compound of the formula (VIII) wherein D1 is R¹⁰OCON—, S or O and L¹ is triflate may be prepared by treating a compound of the formula (VIIIA) with lithium diisopropylamide in an inert solvent such as THF, at a low temperature, for example −78° C., followed by N-phenyl triflamide (for example, see methods described in Synthesis, 993.95 (1991)).

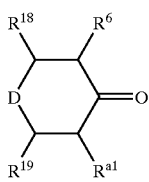
(VIIIA)

Alternatively, a compound of the formula (VIII) wherein $L^1$ is iodo may be prepared by treating a hydrazone of a compound of formula (VIIIA) with iodine in the presence of triethylamine (for example see methods detailed in Tet. Letts., 24, 1605–1608 (1983)).

Compounds of the formula (VII) wherein D1 is $R^{14}CH(R^{13})(CH_2)_m$—N<, aryl-N< or heteroaryl(mono or bicyclic)-N can be prepared by elaboration of the piperidone ring from the appropiate aryl- or heteroarylamine, by reaction with ethyl acrylate to give the corresponding diethylarylimino-bb-dipropionate, which can then be cyclised under Diekmann conditions to the give corresponding piperidone b-ketoester, followed by decarboxylation with heating in acid (see methods described in J.Chem.Soc., 51 10–5118 (1962)).

Alternatively, a compound of the formula (VIII) wherein D1 is heteroaryl-N< may be prepared by reacting an appropiately substituted heterocycle containing a leaving group such as chloro, bromo or iodo with the appropriate 4-piperidone at an elevated temperature, in an inert solvent and optionally with an acid trapping agent.

Suitable catalysts for the catalytic hydrogenation of a compound of the formula (I) or (II) wherein >A1—B1— is >C=C($R^{a1}$)— include Raney nickel, platinum metal or its oxide, rhodium, zinc oxide, palladium-on-charcoal and Wilkinson's catalyst ($RhCl(Ph_3P)_3$. Catalyic hydrogenation is conveniently carried out in the temperature range 0° C. to 150° C., but preferably at ambient temperature and pressure, unless Wilkinson's catalytic is used in which case a temperature of approximately 50° C. and pressure of approximately 50 atmospheres are preferable.

A compound of the formula (IX) may be prepared by reacting an intermediate of the formula (VB) with magnesium to form a Grignard reagent, or alternatively with n-butyl lithium to form a lithiated species (as above), and then reacting the Grignard reagent or lithiated species with a compound of formula (VIIA). The product (VA), wherein >A1—B1— is of the formula >C(OH)CH($R^a$)— may then be elaborated as previously detailed for the compound of the formula (V), but with optional protection of the hydroxyl group.

The dehydration of a compound of the formula (IX) to give a compound of formula (I) or (II) wherein >A1—B1— is of the formula >C=CR$^{a1}$— may be carried out using agents such as polyphosphoric acid, trifluoroacetic acid, trifluoroacetic anhydride, p-toluenesulfonic acid, sulfuric acid, thionyl chloride etc., in an inert solvent such as toluene, and at elevated temperatures. Suitable protection of the group $R^{20}$ may be necessary as appropriate.

A compound of the formula (I) or (II) wherein >A1—B1— is of the formula >CHCH($R^{a1}$)— may be prepared from a compound of the formula (I) or (II) wherein >A1—B1— is >C=CR$^{a1}$—, by catalytic hydrogenation, using a suitable catalyst such as palladium-on-carbon in an appropiate inert or acidic solvent such as acetic acid. Where an optically active form of compounds of the formula (VI) is used in previous steps, reduction of the >A 1—B1— double bond will produce diastereoisomers which may be separated. Where a particular diastereoisomer is of choice, a chiral asymmetry-inducing catalyst for the reduction can be used.

The reaction between a compound of the formula (X) and (XI) or (XII) is conveniently carried out under similar conditions to those described for the acetylation or sulfonylation of a compound of the formula (III).

A compound of the formula (I) or (II) wherein $R^1$ or $R^{20}$ is azido may be prepared, for example, by reacting a compound of the formula (XIII) with sodium azide in an inert solvent such as DMF in a temperature range of ambient to 100° C., normally in the region of 75° C.–85° C. A compound of the formula (XIII) may be prepared by converting the hydroxy group in a compound of the formula (I) or (II) wherein $R^1$ or $R^{20}$ is hydroxy into a tosyloxy or mesyloxy group by standard methods known in the art. For example, by reacting the compound of the formula (I) or (II) with tosyl chloride or mesyl chloride in the presence of a mild base such as triethylamine, or pyridine.

Suitable reducing agents for reducing azido to amino in a compound of the formula (I) or (II) include triethylamine/hydrogen sulfide, triphenylphosphine or phosphite ester, or hydrogen in the presence of a catalyst. More specifically the reduction of the azido group may be carried out by heating it in an aprotic solvent, such as 1,2-dimethoxyethane, in the presence of $P(OMe)_3$ and subsequently heating in 6N aqueous hydrochloric acid, or reacting it with hydrogen in the presence of palladium on carbon in a solvent such as DMF or ethyl acetate. For further details on the reduction of azides to amines see U.S. Pat. No. 4,705,799. The azido compound may be reduced and converted to a compound of the formula (I) or (II), wherein $R^1$ or $R^{10}$ is acetamido, in situ using acetic anhydride in DMF.

A compound of the formula (I) or (II) wherein $R^1$ or $R^{20}$ is fluoro may be prepared by reacting a compound of the formula (I) or (II) wherein $R^1$ or $R^{20}$ is hydroxy (hydroxy compound) with a fluorinating agent such as diethylaminosulfurtrifluoride in an organic solvent such as dichloromethane in the temperature range of 0° C. to ambient temperature.

When $R^1$ or $R^{20}$ is chloro, the compound of the formula (I) or (II) may be formed by reacting the hydroxy compound with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature.

The (1–4C)alkanesulfonyloxy compound may be prepared by reacting the hydroxy compound with (1–4C)alkanesulfonyl chloride in the presence of a mild base such as triethylamine or pyridine.

The (1–4C)alkylaminocarbonyloxy compound may be prepared by reacting the hydroxy compound with (1–4C)alkyl cyanate in an organic solvent such as THF or acetonitrile, in the presence of triethylamine, in a temperature range of 0° C. to 50° C.

A compound of the formula (11) wherein $R^{20}$ is of the formula —N(CO$_2R^{27}$)CO(1–4C)alkyl is conveniently prepared by reacting a compound of the formula (I) and (II) wherein $R^1$ or $R^{20}$ is hydroxy with an amide of the formula HN(CO$_2R^{27}$)CO(1–4C)alkyl under Mitsunobu conditions. For example, in the presence of tri-n-butylphosphine and 1,1'-(azodicarbonyl)dipiperidine in an organic solvent such as THF, and in the temperature range 0° C.–60° C., but preferably at ambient temperature. Details of analogous Mitsunobu reactions are contained in Tsunoda et al, Tet. Letts., 3, 1639, (1993). Amides of the formula $HN(CO_2R^{27})CO(1-4C)$alkyl may be prepared by standard procedures of organic chemistry which are within the ordinary skill of an organic chemist.

A compound of the formula (I) or (II) wherein $R^1$ or $R^{20}$ is chloro may also be prepared from a compound of the formula (XIII), by reacting the latter compound with lithium chloride and crown ether, in a suitable organic solvent such as THF, in a temperature range of ambient temperature to reflux. A compound of the formula (I) or (II) wherein $R^1$ or $R^{20}$ is (1–4C)alkylthio or (1–4C)alkoxy may be prepared by reacting the compound of the formula (XIII) with sodium thio(1–4C)alkoxide or sodium (1–4C)alkoxide respectively, in an alcohol or THF, in a temperature range of 0° C. to reflux.

It is also possible to convert one $R^7$ group into another $R^7$ group as a final step in the preparation of a compound of the formula (I) or (II) (see the specific examples).

When an optically active form of a compound of the formula (I) is required, it may be obtained by carrying out one of the above procedures using an optically active starting material, or by resolution of a racemic form of the compound or intermediate using a standard procedure.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides a compound of the formula (I), or a pharmaceutically-acceptable salt thereof, for use as a medicament; and the use of a compound of the formula (I) of the present invention, or a pharmaceutically-acceptable salt thereof, in the manufacture of a novel medicament for use in the production of an antibacterial effect in a warm blooded animal, such as man.

In order to use a compound of the formula (I) or a pharmaceutically-acceptable salt thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically-acceptable salt thereof and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness against methicillin-resistant staphylococci. Compounds of this invention may also contain or be co-administered with bactericidal/permeability-increasing protein product (BPI) or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 $mgkg^{-1}$ to 20 $mgkg^{-1}$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S. aureus and coagulase negative staphylococci. The antibacterial spectrum and potency of a particular compound may be determined in a standard test system.

The antibacterial properties of the compounds of the invention may also be demonstrated in-vivo in conventional tests. No overt toxicity or other untoward effects are observed when compounds of the formula I are so tested.

The following results were obtained on a standard in-vitro test system. The activity is described in terms of the minimum inhibitory concentration (MIC) determined by the agar-dilution technique with an inoculum size of $10^4$ CFU/spot.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

| Organism | MIC (μg/ml) Example 1 |
|---|---|
| *Staphylococcus aureus*: | |
| Oxford | 1.0 |
| Novb. Res | 0.5 |
| MRQS | 0.5 |
| MRQR | 0.5 |
| Coagulase Negative Staphylococcus | |
| MS | 0.25 |
| MR | 1.0 |
| *Streptococcus pyogenes* | |
| C203 | 1.0 |
| *Enterococcus faecalis* | 1.0 |
| *Bacillus subtilis* | 0.25 |

Novb. Res = Novobiocin resistant
MRQS = methicillin resistant quinolone sensitive
MRQR = methicillin resistant quinolone resistant
MR = methicillin resistant
MS = methicillin sensitive The invention is now illustrated but not limited by the following Examples in which unless otherwise stated:

i) evaporations were carried out by rotary evaporation in vacuo and work-up procedures were carried out after removal of residual solids by filtration;
(ii) operations were carried out at ambient temperature, that is in the range 18–26° C. and in air unless otherwise stated, or unless the skilled person would otherwise work under an inert atmosphere;
(iii) column chromatography (by the flash procedure) was performed on Merck Kieselgel silica (Art. 9385) unless otherwise stated;
(iv) yields are given for illustration only and are not necessarily the maximum attainable;
(v) the end-products of the formula I generally have satisfactory microanalyses and their structures were confirmed by NMR and mass spectral techniques [proton magnetic resonance spectra were determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets: t, triplet. m, multiplet; fast-atom bombardment (FAB) mass spectral data were obtained using a Platform spectrometer (supplied by Micromass) run in electrospray and, where appropriate, either positive ion data or negative ion data were collected];
(vi) intermediates were not generally fully characterised and purity was in general assessed by thin layer chromatographic, infra-red (IR), mass spectral (MS) or NMR analysis: and
(vii) in which:

| MPLC | is medium pressure chromatography |
|---|---|
| TLC | is thin layer chromatography |
| DMSO | is dimethylsulfoxide |
| CDCl$_3$ | is deuterated chloroform |
| MS | is mass spectroscopy |
| ESP | is electrospray |
| CI | is chemical ionization |
| DMF | is N,N-dimethylformamide |
| THF | is tetrahydrofuran |
| LDA | is lithium diisopropylamide |
| TFA | is trifluoroacetic acid |
| NMP | is N-methylpyrrolidone |
| dba | is dibenzylideneacetone |

Reference Example 1

(5S)-Acetamidomethyl-3-(4-trimethyltinphenyl) oxazolidin-2-one

Hexamethyldistannane (1.77g) followed by Pd(PPh$_3$)Cl$_2$ (155 mg) was added to a partial solution of 5S-acetamidomethyl-3-(4-iodophenyl)oxazolidin-2-one (1.84 g) in dioxan (25 ml). The vessel was purged well with argon and the reaction mixture was stirred at 95–100° C. for 6 hours, after which the reaction was judged as complete by TLC. The solution was decanted from a film of black gum which had separated, and evaporated. The title product was isolated as an oil by MPLC (Merck 9385 silica using as eluant a mixture of methanol and dichloromethane increasing in polarity from 5% to 10% methanol) which crystallised in 59% yield (1.19 g) on trituration with ether. See also WO Patent 94-13649 (23.06.94) for preparation of Reference Example 1.

NMR (300 MHz, DMSO-D6): δ0.25(s,9H), 1.84(s,3H), 3.42(t,2H), 3.74(d of d,1H), 4.10(t,1H),7.50(m,4H), 4.70(m, 1H), 8.22(t,1H).

MS: ESP+(M+H)=397.

Reference Example 2

N-((5S)-3-(3-Fluoro-4-(1-tert-butoxycarbonyl-1,2,5, 6-tetrahydropyrid-4-yl)phenyl)-2-oxooxazolidin-ylmethyl)acetamide Lithium chloride (1.53 g) was added to a stirred solution of of t-butyl-1,2,3,6-tetrahydro-4-(trifluoromethylsulfonyloxy)pyridine-1-carboxylate (4.97 g) in NMP (50 ml), followed by Pd$_2$(dba)$_3$ (550 mg) and the vessel was purged well with argon. After stirring for 5 minutes at ambient temperature, a solution of N-((5S)-3-(3-fluoro-4-trimethyltinphenyl)-2-oxooxazolidin-5-ylmethyl) acetamide (4.99 g, WO Patent 94-13649, 23.06.94) in NMP (20 ml) was added. The reaction mixture was stirred at ambient temperature for 5 hours, then at 50° C. for 18 hours. TLC (ethyl acetate) indicated that the reaction was complete. A 2.0M aqueous potassium fluoride solution (12 ml) was added and the reaction mixture stirred at ambient temperature for 1½ hours. Water was added and the product was extracted with ethyl acetate. The organic phase was washed with water, brine, dried over anhydrous sodium sulfate and evaporated to a gum. The title compound was isolated as a gel in 68% yield (4.39 g) by MPLC (Merck 9385 silica, using as eluant a mixture of methanol (3.5%) and dichloromethane), and used in subsequent steps without further purification.

NMR (300 MHz, DMSO-D6): δ2,40(m, 1H), 3.40(m, 3H), 3.50(m, 1H), 3.70(m, 1H), 3.98(m, 2H), 4.10(m, 1H), 4.70(m, 1H), 5.95(m, 1H), 7.35(m, 3H), 8.20(t, 1H).

Reference Example 3

5,6-Dihydro-4-trifluoromethylsulfonyloxy-2H-pyran

LDA/THF (31.5 ml of 1.92M solution) was slowly added to a stirred solution of tetrahydro-4H-pyran4-one (5.5 g) in THF (30 ml) at −70° C., under argon. The mixture was stirred for 30 minutes at −70° C. and then a solution of N-phenyl triflimide (21.6 g) in THF (30 mls) was added. The mixture was allowed to warm to ambient temperature and stirred for 18 hours. The reaction mixture was evaporated and subjected to chromatography by MPLC on Alumina (ICN, N32-63, using as eluant a mixture of ethyl acetate (5%) and iso-hexane). The product was distilled by Kugelruhr (100° C./10 mm). Remaining traces of the triflimide reagent were removed by a second MPLC (Silica, using as eluant a mixture of ethyl acetate (5%) and iso-hexane) followed by a second Kugelruhr distillation, giving the title compound as a colourless oil in 40% yield (5.1 g), which was stored at −20° C.

NMR (300 MHz, CDCl$_3$): δ2.24(m,2H), 3.90(m,2H), 4.25(m,2H), 5.82(m, 1H).

Reference Example 4

1-(4-Bromo-3-fluorophenyl)-2,2,5,5-tetramethyl-1,2,5-azadisilalidine

Triethylamine (56.8 g) was added to a stirred solution of 4-bromo-3-fluoroaniline(42.75 g, JCS, 2815 (1958)) in dichloromethane (400 ml) followed by the slow addition, with ice-bath cooling, of a solution of 1,2-bis (chlorodimethylsilyl)ethane (50.79 g) in dichloromethane (100 ml). After stirring for 2 days, an NMR of a worked up sample showed that the reaction was complete. The reaction mixture was washed with ice cold 2N aqueous Na$_2$HPO$_4$ and water, dried over anhydrous magnesium sulfate and evaporated to give a brown oil. The title compound was isolated in 93% yield (69.4 g) by vacuum distillation, (bp=105–110° C./0.2 bar).

NMR (300 MHz CDCl$_3$): δ0.22 (s, 12H), 0.85 (s, 8H), 6.52 (d of d, 1H), 6.65 (d of d, 1H), 7.30 (t, 1H).

Reference Example 5

4-(1-Benzyl-4-hydroxy-4-piperidyl)-3-fluoroaniline n-Butyllithium/hexane (129 ml of 1.40M) was slowly added to a stirred solution of Reference Example 4 (59.76 g) in dry THF (300 ml) at −70° C. under argon. The solution was stirred for 5 minutes, then a solution of N-benzyl-4-piperidone (37.8 g) in THF (150 ml) was slowly added. The reaction mixture was allowed to warm to ambient temperature and stirred for 3 hours. The reaction mixture was then quenched by the addition of ice, followed by water, then acidified to <pH1 by the addition of 5N aqueous HCl. After stirring for 5 minutes the mixture was extracted with ether and the organic phase discarded. The aqueous phase was basified with a slight excess of aqueous sodium hydroxide and the product was extracted with ether. The organic phase was washed with brine, dried over anhydrous sodium sulfate and evaporated to give the title compound as an oil in which crystallized on trituration with cyclohexane (yield=39.49 g, 73%)

NMR (300 MHz DMSO-D6): δ1.55(d, 2H), 2.10(d of t, 2H), 2.42(m, 2H), 2.55(obscured by DMSO), 3.50(s, 2H), 4.65(s, 1H), 5.18(s, 2H), 6.25(d of d, 1H), 6.33(d of d, 1H), 7.30(m, 6H).

MS: ESP+(M+H)=301.

Reference Example 6

3-Fluoro-4-(1-benzyl-1,2,5,6-tetrahydropyrid-4-yl) aniline

A solution of Reference Example 5 (36.0 g) in 5N aqueous HCl (200 ml) was heated under reflux for 9 hours. Concentrated HCl (50 ml) was added and reflux was continued for a further 4 hours. The reaction mixture was basified, with cooling, with 40% aqueous sodium hydroxide solution and extracted with ether. Addition of aqueous ammonium hydroxide solution avoided problems with insoluble partial salts. The organic phase was washed with brine, dried over anhydrous sodium sulfate and evaporated well giving the title compound as a viscous gum in 96% yield (32.33 g).

NMR (300 MHz DMSO-D6): δ2.35(s, 2H), 2.55(t, 2H), 2.98(d, 2H), 3.53(s, 2H), 5.35(s, 2H), 5.75(s, 1H), 6.29(m, 2H), 6.95(t, 1H), 7.30(m, 5H).

MS: ESP+(M+H)=283.

Reference Example 7

N-Benzyloxycarbonyl-3-fluoro-4-(1-benzyl-1,2,5,6-tetrahydropyrid-4-yl)aniline Dibenzyl dicarbonate (43 g) was slowly added to a stirred solution of Reference Example 6 (28.2 g) in dichloromethane (200 ml) at 0–5° C. The reaction mixture was allowed to warm to ambient temperature and stirred for 18 hours. The solution was evaporated to an oil which was triturated with ether. Sticky, insoluble material was discarded and the filtrate was purified by chromatography (MPLC on silica, using as eluant a mixture of ethyl acetate (25%) and iso-hexane). The product was taken into ethyl acetate and precipitated as the HCl salt by addition of a mixture of HCl and ethyl acetate. The resulting product was filtered off, washed with ethyl acetate and dried under vacuum to give the title product.

Yield=10.2 g (23%)

NMR (300 MHz DMSO-D6): δ2.61(m, 1H), 2.85(m, 1H), 3.20(m, 1H), 3.53(m, 1H), 3.75(s, 2H), 4.40(t, 2H), 5.15(s, 2H), 5.95(s, 1H), 7.35(m, 11H), 7.60(m, 2H).

MS: ESP+(M+H)=417.

Reference Example 8

N-tert-Butoxycarbonyl-N-((5R)-3-(3-fluoro-4-benzyl-1,2,5,6-tetrahydropyrid-4-yl)phenyl)-2-oxooxazolidin-5-ylmethyl)acetamide BOC-acetamide (2.85 g, Chem.Pharm.Bull.Jap.,36, 3125 (1988) was added to a stirred partial solution of Example 13 (4.55 g) in dry THF (80 ml) and the mixture cooled to 0–4° C. under argon. Tributylphosphine (3.62 g) was added, followed by portion-wise addition of 1,1'-(azodicarbonyl)-dipiperidine (4.51 g). The reaction mixture was stirred for 30 minutes at 0–4° C. during which time a precipitate formed. The reaction mixture was allowed to warm to ambient temperature and stirred for 18 hours. The reaction mixture was filtered and evaporated to a gum. The title compound was rapidly isolated by MPLC (silica using as eluant a mixture of ethyl acetate (70%) and iso-hexane) as a gum and subjected to the minimum of handling (brief evaporation at <40° C.) before deprotection in Example 12.

Yield=6.9 g (inc. some solvent).

Reference Example 9

4-(1-tert-butyloxycarbonyl-1,2,5,6-tetrahydropyrid-4yl)-3,5-difluoroaniline nBuLi (1.6M in hexanes, 33.3 ml) was added to a solution of N,N-[1,2-bis(dimethylsilyl)ethane]-3,5-difluoroaniline (12.0 g, J.Org. Chem., 60, 5255–5261 (1995)) in 150 ml THF at −70° C., maintaining temperature below −70° C. during the addition. The mixture was then stirred at that temperature for 4 hours. A solution of $ZnCl_2$ (0.5M in THF, 106.7 ml) was then added at <60° C., the mixture allowed to warm to ambient temperature and then degassed by bubbling argon through the solution for 15 minutes. Tetrakis (triphenylphosphine)Pd⁰ (1.54 g) was then added together with t-butyl-1,2,5,6-tetrahydro-4-(trifluoromethylsulfonyloxy)-pyridine carboxylate (15.4 g, Synthesis, 993 (1991)), the mixture degassed again and stirred overnight at ambient temperature. After refluxing for two hours the mixture was cooled to 10° C. and added to 100 mm ice water. After adjusting the pH to 2–3 with 5N HCl and stirring at 10° C. for 5 minutes the mixture was brought to pH 8 with $NaHCO_3$, extracted into ethyl acetate (2×150 ml) and evaporated to give a dark oil which was chromatographed on alumina (ICN-N-32-63) with isohexane/ethyl acetate 4:1. Trituration of the resulting oil gave a solid (6.62 g, 48%).

NMR (300 MHz, DMSO-D6)d: 1.46(s, 9H), 2.27(broad s, 2H), 3.52(d/d, 2H), 3.97(broad s, 2H), 5.70(s, 3H), 6.20(d, 2H).

Reference Example 10

N-Benzyloxycarbonyl-4-(1-tert-butyloxycarbonyl-1,2,5,6-tetrahydropyrid-4-yl)-3,5-difluoroaniline $NaHCO_3$ (5.5 g) was added to a mixture of Reference Example 9 (10.0 g), acetone (150 ml) and water (75 ml) and the mixture cooled in an ice-bath. A solution of benzylchloroformate (5.3 ml) in 10 ml of acetone was added slowly, the mixture was stirred whilst the temperature was warmed to ambient and then stirred for a further hour. Water (100 ml) was added and the mixture extracted with ethyl acetate (100 ml+2×50 ml). The combined extracts were dried and evaporated to give a solid which was recrystallised from 90 ml of acetonitrile to give a solid (11.2 g). Recrystallisation of the residues gave further solid (0.73 g). Total yield (83%).

NMR (300 MHz, DMSO-D6)d: 1.42(s, 9H), 2.25(broad s, 2H), 3.50(t, 2H), 3.95(Broad s, 2H), 5.15(s, 2H), 5.78(s, 1H), 7.15(d, 2H), 7.38(m,5H), 10.16(broad s, 1H).

Reference Example 11

(5R)-Hydroxymethyl-3-(3,5-difluoro-4-(tert-butyloxycarbonyl-1,2,5,6-tetrahydropyrid-4-yl)phenyl)oxazolidin-2-one nBuLi (1.45M in hexanes, 15.7 ml) was added dropwise at <−70° C. to a solution of Reference Example 10 (9.65 g) in anhydrous THF (200 ml) at −70° C. After 20 minutes a solution of (R)-glycidyl butyrate (3.44 g) in 25 ml THF was added at the same temperature. After the addition the cooling bath was removed and the reaction allowed to stir to ambient temperature overnight. After addition of methanol (15 ml) and stirring for 10 minutes, 100 ml ethyl acetate was added, the mixture cooled to 10° C. and 0.5M HCl (20 ml) added slowly. After separation of the aqueous phase it was re-extracted with ethyl acetate (2×100 ml) and the combined organic phases were washed with saturated $NaHCO_3$ solution, with brine and evaporated to give an oil (12.0 g). Chomatography on silica gel with ethyl acetate gave a solid (7.66 g, 86%).

NMR (300 MHz, DMSO-D6)d: 1.40(s, 9H), 227(broad s, 2H), 3.51(m, 3H), 3.64/3.68(m/m, 1H), 3.80(m, 1H), 3.97(broad s, 2H), 4.05(t, 1H), 4.70(m, 1H), 5.18(t, 1H), 5.82(broad s, 1H), 7.32(m, 2H).

Reference Example 12

3,5-difluoro-4-(2,3-dihydropyran-4-yl)aniline nBuLi (1.4M in hexanes, 63.5 ml) was added dropwise to a solution of N,N-[1,2-bis(dimethylsilyl)ethane]-3,5-difluoroaniline (20.0 g, J.Org.Chem., 60, 5255–5261 (1995)) in 200 ml THF at −70° C. The mixture was stirred at that temperature for 4 hours. Chlorotitanium trisopropoxide (1.0M in hexanes, 89 ml) was then added dropwise at the same temperature, and the mixture allowed to warm to ambient temperature for 30 minutes. The mixture was recooled to −70° C. and tetrahydro-4H-pyran-4-one (9.0 g in a few ml of THF) added dropwise and the reaction mixture allowed to stir at ambient temperature for 48 hours. After cooling in an ice bath, conc.HCl was added to pH 1–2, the organic phase separated and the aqueous phase rextracted with ether. The aqueous phase was adjusted to pH 9 with 2.5N NaOH, a small amount of solid filtered off and the filtrate extracted with ethyl acetate (4×100 ml). Work-up (ie. washing and evaporation of solvent) gave an oil which was dissolved in 75 ml dioxan and 75 ml 5N Hcl. The mixture was refluxed for 15 minutes and the dioxan removed in vacuo. The residue was retaken up in dilute HCl, extracted with ether. The aqueous layer was basified to pH 8 with $NaHCO_3$ and extracted with ethyl acetate (3×75 ml). Evaporation in vacuo gave a solid (8.5 g, 45%).

NMR (300 MHz, DMSO-D6)d: 2.20(broad s, 2H), 3.74(t, 2H), 4.12(q, 2H), 5.65(s, 2H), 5.70(s, 1H), 6.10(s, 1H), 6.18(s, H).

MS: ESP+(M+H)=212.

Reference Example 13

N-Benzyloxycarbonyl-4-(2,3-dihydro-6H-pyran-4-yl)-3,5-difluoroaniline

Benzylchloroformate (6.6 ml, 7.88 g) was added to a mixture of Reference Example 12 (8.4 g), acetone (150 ml) and water (75 ml) containing $NaHCO_3$ (7 g) in an ice-bath. The mixture was stirred for 3 hours whilst warming to ambient temperature. At the end of this period 100 ml water was added, the mixture extracted with ethyl acetate (3×100 ml) and evaporated in vacuo to give a crude solid which was triturated with ether to give a solid (75%).

NMR (300 MHz, DMSO-D6)d: 2.25(broad s, 2H), 3.76(t, 2H), 4.18(m, 2H), 5.15(s, 2H), 5.85(s, 1H), 7.14(s, 1H), 7.18(s, 1H), 7.38(m, 5H), 10.16(broad s, 1H).

Reference Example 14

(5R)-Hydroxymethyl-3-(3,5-difluoro-4-(2,3-dihydro-6H-pyran-4-yl)phenyl)oxazolidin-2-one nBuLi (1.4M in hexanes, 23.2 ml) was added dropwise to a solution of Reference Example 13 (10.2 g) in TBF (200 ml) at −70° C. and the mixture stirred for 20 minutes. A solution of (R)-glycidyl butyrate (4.68 g) in THF (20 ml) was added dropwise and the reaction allowed to stir over 48 hours, warming to ambient temperature over a few hours. Methanol (20 ml) was added, the mixture stirred for 10 minutes, then ethyl acetate (100 ml) followed by 100 ml 0.5N HCl added. The organic phase was separated, the aqueous re-extracted and the combined organic phases washed with saturated NaHCO, solution, followed by evaporation in vacuo to give a crude solid which was purified on silica-gel using ethyl acetate as eluant to give a solid (7.4 g, 80%).

NMR (300 MHz, DMSO-D6)d: 2.29(broad s, 2H), 3.53 (m, 1H), 3.67(m, 1H), 3.79(m, 3H), 4.06(t, 1H), 4.19(m, 2H), 4.71(m, 1H), 5.19(t, 1H), 5.89(m, 1H), 7.30(s, 1H), 7.36(s, 1H).

MS: ESP+(M+H)=312.

Reference Example 15

(2RS)-2-Methyl-4-trifluoromethylsulfonyloxy-3,6- and -5,6-dihydropyran (RS)-2-Methyl-tetrahydro-4H-pyran-4-one (1.04 g, Chem.Ber., 88, 1053, (1955)) in dry THF (30 ml) at −78° C. was treated with LDA (2.0 M in heptane/THF/PhEt) (4.56 ml) under argon. After 45 minutes N-phenyl-bis (trifluoromethanesulfonimide) (3.58 g) was added in one go and stirring was continued for 1 hour at −78° C. The ice bath was then removed and stirring continued for a further 19 hours. The solution was evaporated and the residue purified by firstly silica-gel MPLC [using a mixture of 4% ethyl acetate and hexanes as eluant], and then by bulb-to-bulb distillation. Vinyl trifluoromethanesulfonate (1.36 g, 60%) as a 1.4:1 mixture of the title methyl-regioisomers was collected as the fraction at 120° C./10 mmHg.

NMR (250 MHz, CDCl$_3$)d: 1.29 and 1.31 (m/m, 3H each), 2.17–2.43 and 2.54–2.70 (m/m, 2H each), 3.66–3.82 (m, 2H), 4.10 (ddd, 1H), 4.19–4.40 (m,3H,), 5.68–5.74 (m, 1H) and 5.79–5.84 (m, 1H).

Reference Example 16

2,6-Dimethyl-4-hydroxy-2,3,5,6-tetrahydro-4H-pyran 2,6-Dimethyl-4H-pyran-4one (5.0 g) in ethanol (40 ml) was hydrogenated under 10% Pd—C (0.5 g) at 10 bar of hydrogen for 2 days. The solution was then evaporated to an oil which was purified by silica-gel MPLC [using a 1:1 mixture of ethyl acetate and hexane as eluant] to give the title product (3.71 g, 74%).

NMR (300 MHz CDCl$_3$)d: 1.16–1.25 (m,6H), 1.40–1.55 (m, 2H), 1.60–1.69 (m, 1H), 1.89–1.99 (m, 1H), 3.40–3.50 (m, 1H), 3.70–3.99 and 4.21 (m/m, together 2H).

Reference Example 17

2,6-Dimethyl-2,3,5,6-tetrahydro-4H-pyran-4-one

Reference Example 16 (3.71 g) was dissolved in dry dichloromethane (50 ml) and pyridine chlorochromate (PCC) (9.2 g) was added portionwise with stirring. The mixture was stirred for 18 hours, filtered through Celite and evaporated. The residue was purified by bulb-to-bulb distillation (90° C., 16 mbar) to afford the title ketone (1.09 g, 30%).

NMR (300 MHz, CDCl$_3$)d: 1.32 (d, 6H), 2.17–2.40 (m, 4H) and 3.68–3.80 (m, 2H).

Reference Example 18

2,6-Dimethyl-4-trifluoromethylsulfonyloxy-5,6-dihydropyran

Reference Example 17 (1.09 g) in dry THF (10 ml) at −78° C. was treated with LDA (2.0 M in heptane/THF/PhEt) (5.55 ml) under argon. After 30 minutes N-phenyl-bis (trifluoromethanesulfonimide) (3.21 g) was added in one go and stirring was continued for 1 hour at −78° C. The ice bath was then removed and stirring continued for a further 19 hours. The solution was evaporated and the residue purified by silica-gel MPLC [using a mixture of 4% ethyl acetate and hexanes as eluant] to give the vinyl triflate (1.75 g, 79%).

NMR (300 MHz, CDCl$_3$)d: 1.50 and 1.51 (d/d, each 3H), 2.19–2.40 (m, 2H), 3.70–3.83 (m, 1H), 4.30–4.40 (m, 1H) and 5.70 (s, 1H).

Reference Example 19

There is no compound with Reference Example No. 19.

Reference Example 20

2-Benzyloxymethyl-2,3,5,6-tetrahydro-4H-pyran-4-one

A mixture of (RS)-2-benzyloxymethyl-2,3-dihydro-4H-pyran-4-one (0.82 g, J. Org. Chem., 44, 811 (1979)) in ethanol (15 ml) containing 10% Pd—C (0.089 g) and triethylamine (10 drops) was hydrogenated until NMR spectroscopy indicated almost complete reaction. The solution was evaporated and the residue purified by silica-gel MPLC [25% EtOAc/hexanes] and then bulb-to-bulb distillation [220° C./2 mmHg] to give the title ketone (0.47 g, 56%).

NMR (300 MHz, CDCl$_3$)d: 2.30–2,40 (m, 2H), 2.21–2.70 (m, 2H), 3.55 (d, 2H), 3.70 (dt, 1H), 3.80–3.89 (m, 1H), 4.35 (dd, 1H), 4.60 (s,2H) and 7.30–7.39 (m, 5H).

MS: ESP+(M+H)=221.

Reference Example 21

(2RS )-2-Benzyloxymethyl-4-trifluoromethylsulfonyloxy-3,6- and -5,6-dihydropyran Under analogous conditions to those described in Reference Example 18, Reference Example 20 (6.1 g) was transformed into the crude vinyltriflate. Silica-gel MPLC [using a mixture of 10% ethyl acetate and hexanes as eluant], then alumina MPLC [using a mixture of 5% ethyl acetate and hexanes as eluant] gave a mixture of the title products (5.9 g, 61%).

NMR (300 MHz, CDCl$_3$)d: 2.20–2.31 (m, 2H), 2.42–2.70 (m, 2H), 3.45–3.62 (m 4H), 3.70–3.90 (m, 2H), 4.10–4.19 (m, 1H), 4.22–4.48 (m, 3H), 4.52–4.63 (m, 4H), 5.79 (s, 1H), 5.80–5.82 (m, 1H) and 7.25–7.40 (m, 10H).

Reference Example 22

N-((5S)-3-(4-(2-methanesulfonyloxymethyl-3,6- and -5.6-dihydropyran-4-yl)phenyl)-2-oxooxazolidin-5-ylmethy)acetamide Mesyl chloride (0.080 g, 0.054 ml) was added slowly to a stirred mixture of Example 52 (0.183 g), triethylamine (0.066 g, 0.090 ml) and dichloromethane (8 ml) at 0° C.. After 1 hour, more mesyl chloride (0.070 ml) and triethylamine (0.070 ml) were added and stirring continued for a further 2 hours. The solution was then washed with 10% HCl. saturated aqueous NaHCO$_3$ solution and with water, then dried and evaporated to an oil which was purified by Isolute silica-gel chromatography [using a mixture of 6% MeOH and CH$_2$Cl$_2$ as eluant] to give a mixture of the title mesylates (0.190 g, 85%).

NMR (300 MHz, CDCl₃)d: 2.05 (s, 3H), 2.31–2.55 (m, 1H), 2.91–3.05 (m, 1H m), 3.06, 3.08 and 3.12 (s/s/s, together 3H), 3.60–4.28 (m, 6H), 4.30–4.64 (m, 3H), 4.75–4.90 (m, 1H), 5.96, 6.12 and 6.30 (each broad s, together 2H) and 7.32–7.60 (m, 4 H).

MS: ESP+(M+H)=425.

Reference Example 23

N-((5S)-3-(4-(2-azidomethyl-3,6- and 5,6-dihydropyran-4-yl)phenyl)-2-oxooxazolidin-5-ylmethylacetamide The mixture of mesylates Reference Example 22 (0.177 g) and sodium azide (0.041 g) in dimethyl sulfoxide (2 ml) were stirred at 80° C. for 5 hours. NMR indicated very little consumption of starting material and more sodium azide (0.050 g) was added. The mixture was heated at 80° C. for 18 hours. The resulting mixture was dissolved in ethyl acetate and washed twice with water. The organic layer was dried and evaporated to afford the title mixture of azides (0.138 g, 89%).

NMR (300 MHz, CDCl₃)d: 2.01 and 2.05 (s/s, together 3H), 2.28–2.53 (m, 2H), 3.38–3.49 (mm, 2H), 3.60–3.70 (m, 2H), 3.78–3.90 (m, 2H), 4.09 (t, 2H), 4.40–4.50 (m, 1H), 4.72–4.95 (m, 1H), 5.98 and 6.12 (s/s, together 1H), 6.50 (broad t, 1H,) and 7.30–7.55 (m, 4H).

MS: ESP+(M+H)=372.

Reference Example 24

(2RS)-2-Benzyloxymethyl-4-trifluoromethylsulfonyloxy-3,6-dihydropyran (RS)-2-Benzyloxymethyl-2,3-dihydro-4H-pyran-4-one (5.69 g, J. Org. Chem., 44, 811 (1979)) in dry THF (200 ml) was treated with L-selectride (27 ml, 1.0M in THF) at −78° C. and stirred for 1.25 hour. N-Phenyl-bis (trifluoromethanesulfonimide) (10.35 g) was added and stirring continued for 3 days with warming to ambient temperature. The solution was evaporated to an oil which was purified by firstly silica-gel MPLC [10% EtOAc/hexanes as eluant], then alumina MPLC [10% EtOAc/hexanes as eluant] to afford the title vinyl triflates (6.00 g, 66%).

NMR (300 MHz CDCl₃)d: 2.23 (dt, 1H), 2.41–2.58 (m, 1H), 3.50–3.62 (m, 2H), 3.80–3.90 (m, 1H), 4.22–4.43 (m, 2H), 4.60 (s, 2H), 5.80 (d, 1H), 7.25–7.41 (m, 5H).

EXAMPLE 1

N-((5S)-3-(4-(1-tert-butoxycarbonyl-1,2,5,6-tetrahydropyrid-4-yl)phenyl)-2-oxooxazolidin-5yl-methyl)acetamide To a stirred solution of t-butyl-1,2,3,6-tetrahydro-4-(trifluoromethylsulfonyloxy)-pyridine-1-carboxylate (497 mg, Synthesis, 993 (1991)) in NMP (8 ml), was added Pd₂(dba)₃ (60 mg), triphenylarsine (80 mg) and lithium chloride (166 mg), and the vessel was purged well with argon. After stirring for 5 mins. at ambient temperature, a solution of the starting material (516 mg, Reference Example 1) in NMP (2 ml) was added and the reaction mixture stirred at ambient temperature for 18 hours. TLC (ethyl acetate) indicated incomplete reaction so more t-butyl-1,2,3,6-tetrahydro-4-(trifluoromethylsulfonyloxy) pyridine-1-carboxylate (497 mg) was added and the reaction mixture was heated at 40° C. for a further 24 hours, after which the reaction was complete. A 1.0M solution of aqueous potassium fluoride (1.0 ml) was added and the reaction mixture was stirred at ambient temperature for 30 mins. Water was added and the product was extracted with ethyl acetate, with filtration of the 2 phase mixture. The organic phase was washed with water, saturated aqueous sodium chloride solution, dried over anhydrous sodium sulfate and evaporated to a semi-solid gum. The product was isolated by MPLC (Merck 9385 silica, using as eluant a mixture of acetonitrile and ethyl acetate increasing in polarity from 0% to 50% acetonitrile over 15 minutes), and was crystallised by dissolving in a small volume of ethyl acetate and triturating with ether (yield=125 mg, 23%).

NMR (200 MHz, DMSO-D6): δ1.42(s,9H), 2.43(m, obscured by DMSO), 3.42(t,2H), 3.52(t,2H), 3.75(d of d,1H), 3.98(d,2H), 4.16(t,1H), 4.71 (m,1H), 6.12(s,1H), 7.49(AB,4H), 8.20(t,1H).

MS: ESP+(M+H)=416.

EXAMPLE 2

N(5S)-3-(4-(1,2,5,6-tetrahydropyrid-4-yl)phenyl)-2-oxooxazolidin-5-ylmethyl)acetamide A general procedure for deprotection was used as follows. The starting material (Example1) was dissolved in a small volume of trifluoroacetic acid and the yellow solution was heated briefly to reflux. Ether (10×volume of TFA used) was added, precipitating a sticky gum. The solvent was decanted off and the gum crystallised on trituration with ether. The TFA salt of the product was filtered off, washed with ether and dried under vacuum.

For example, 10.5 mg of starting material in 0.1 ml of TFA was treated in this way to give the title compound in 97% yield (10.5 mg).

NMR (300 MHz, DMSO-D6): δ1.81(s,3H), 2.65(s,2H), 3.35(partially obscured by H₂O), 3.42(t,2H), 3.75(m,3H), 4.13(t,1H), 4.73(m,1H), 6.18(s,1H), 7.54(AB,4H), 8.25(t, 1H), 8.85(s,2H).

MS: ESP+(M+H)=316.

EXAMPLE 3

N((5S)-3-(4-(1-methoxycarbonyl-1,2,5,6-tetrahydronyrid-4-yl))phenyl)-2-oxooxazolidin-5-ylmethyl)acetamide To a stirred solution of the starting material (Example 2) (129 mg) in a mixture of acetone (2 ml) and water (1 ml) was added sodium hydrogen carbonate (101 mg), and the mixture was cooled to 0–5° C. Methyl chloroformate (34 mg, 28 μl) was added and stirring continued at 0–5° C. for 30 minutes. Then the reaction mixture was allowed to warm to ambient temperature over 30 minutes, after which TLC (10% methanol in dichloromethane) showed the reaction was complete. The reaction mixture was diluted with water and extracted with ethyl acetate. The organic phase was washed with saturated aqueous sodium chloride solution, dried over anhydrous sodium sulfate and evaporated to give a crystalline solid which was recrystallised from ethyl acetate (yield=87 mg, 78%).

NMR (200 MHz, DMSO-D6): δ1.84(s,3H), 3.42(t,2H), 3.60(t,3H), 3.64(s,3H), 3.75(d of d,1H), 4.05(d,2H), 4.12(t, 1H), 4.70(m,1H), 6.14(s,1H), 7.47(AB,4H), 8.24(m,1H).

MS: ESP+(M+H)=374.3.

Analysis: Calculated for C₁₉H₂₃N₃O₅: C, 61.1; H, 6.2; N, 11.1%. Found: C, 60.9; H, 5.9; N, 11.0%.

EXAMPLE 4

N-((5S)-3-(4-(1-Methylsulfonyl-1,2,5,6-tetrahydroprid-4-yl)phenyl)-2-oxo-oxazolidin-5-ylmethy)acetamide Triethylamine (253 mg), followed by a solution of methanesulfonyl chloride (69 mg) in dichloromethane (1 ml) was added, with ice-bath cooling, to a stirred suspension of N(5S)-3-(4-(1,2,5,6-tetrahydropyrid-4-yl)phenyl)-2-oxooxazolidin-5-ylmethyl)acetamide (215 mg, Example 2) in dichloromethane (10 ml). TLC showed complete reaction after 2 hours. The reaction mixture was washed with 2N. HCl, water, saturated sodium hydrogen carbonate and brine. The organic phase was dried over anhydrous sodium sulfate and evaporated to give the title compound as a crystalline solid which was recrystallised from acetonitrile (yield=117 mg, 60%).

NMR (300 MHz DMSO-D6): δ1.80(s, 3H), 2.55(broad, 2H), 2.90(s, 3H), 3.35(m, 4H), 3.73(d of d, 1H), 3.85(d, 2H), 4.10(t, 1H), 4.70(m, 1H), 6.15(s, 1H), 7.48(AB, 4H), 8.21(t, 1H).

MS: ESP+(M+H)=394.

Analysis: Calculated for $C_{18}H_{23}N_3O_5S$: C, 54.9; H, 5.9; N, 10.7%. Found: C, 54.5; H, 5.6; N, 10.7%.

EXAMPLE 5

N-((5S)-3-(4-(1-Acetyloxymethylcarbonyl-1,2,5,6-tetrahydropyrid-4-yl)phenyl)-2-oxooxazolidin-5-ylmethyl)acetamide Sodium hydrogen carbonate (1.89 g) was added to a stirred solution of Example 2 (1.92 g) in a mixture of acetone (25 ml) and water (12.5 ml), and the mixture cooled to 0–3° C. Acetoxyacetyl chloride (1.23 g, 0.97 ml) was added dropwise over 5–10 mins. and the reaction mixture was stirred at 0–5° C. for 30 minutes then allowed to warm to ambient temperature over 1 hour. TLC (10% methanol in dichloromethane) showed complete reaction. The reaction mixture was diluted with water and extracted well with ethyl acetate. The organic phase was washed with brine and dried over anhydrous sodium sulfate. The title compound crystallized during evaporation of the solvent and was triturated with ether (yield=1.70 g, 91%).

NMR (300 MHz, DMSO-D6): δ1.81(s, 3H), 2.08(s, 3H), 2.5(obscured by DMSO), 3.40(t, 2H), 3.55(t, 1H), 3.65(t, 1H), 3.75(d of d, 1H), 4.10(m, 3H), 4.70(m, 1H), 4.85(d, 2H), 6.15(s, 1H), 7.48(m, 4H), 8.20(t, 1H).

MS: ESP+(M+H)=416.

EXAMPLE 6

N-((5S)-3-(4-(1-Hydroxyacetyl-1,2,5,6-tetrahydropyrid-4-yl)phenyl)-2-oxooxazolidin-5-ylmethyl)acetamide Example 5 (1.70 g) was stirred at ambient temperature with saturated methanolic ammonia (20 ml) for 18 hours. The initial suspension gave a solution after several hours from which the product crystallized. TLC showed complete reaction. The title compound was filtered off and washed with a little methanol (yield=1.28 g, 84%).

NMR (300 MHz, DMSO-D6): δ1.81(s, 3H), 2.5(obscured by DMSO), 3.39(t, 2H), 3.50(m, 1H), 3.72(m, 2H), 4.10(m, 5H), 4.55(d, 1H), 4.70(m, 1H), 6.15(d, 1H), 7.45(m, 4H), 8.21(t, 1H).

MS: ESP+(M+H)=374.

Analysis: Calculated for $C_{19}H_{23}N_3O_5$: C, 61.1; H, 6.2; N, 11.3%. Found: C, 60.8; H, 6.3; N, 11.1%.

EXAMPLE 7

N-((5S)-3-(3-Fluoro-4-(1,2,5,6-tetrahydropyrid-4-yl)phenyl)-2-oxooxazolidin-5-ylmethyl)acetamide Reference Example 2 (4.1 g) was dissolved in TFA (10 ml) and the yellow solution was heated briefly to reflux. The bulk of the TFA was evaporated and the residue was triturated with ether, precipitating initially a sticky gum which solidified to a yellow powder. The title compound was obtained by filtration as a TFA salt, washed with ether and dried under vacuum (yield=2.64 g, 62%).

NMR (300 MHz, DMSO-D6): δ1.84(s, 3H), 2.65(s, 2H), 3.40(m, partially obscured by $H_2O$, 4H), 3.75(m, 3H), 4.10(t, 1H), 4.75(m, 1H), 6.05(m, 1H), 7.42(m, 3H), 8.25(t, 1H), 8.85(s, 2H).

EXAMPLE 8

N-((5S)-3-(3-Fluoro-4-(1-acetyloxymethylcarbonyl-1,2,5,6-tetrahydronyrid-4-yl)phenyl)-2-oxooxazolidin-5-ylmethyl)acetamide The title compound was prepared using a similar method to that describing the preparation of Example 5, except using Example 7 as the starting material (2.41 g). Yield=2.2 g, 94%.

NMR (300 MHz, DMSO-D6): δ1.82(s, 3H), 2.10(s, 3H), 2.42(s, 2H), 3.40(m, 2H), 3.55(m, 1H), 3.62(m, 1H), 3.72(m, 1H), 4.10(m, 3H), 4.72(m, 1H), 4.82(d, 2H), 6.0(m, 1H), 7.38(m, 3H), 8.21(t, 1H).

MS: ESP+(M+H)=434.

EXAMPLE 9

N-((5S)-3-(3-Fluoro-4-(1-hydroxyacetyl-1,2,5,6-tetrahydronyrid-4-yl)phenyl)-2-oxooxazolidin-5-ylmethyl)acetamide The tide compound was prepared using a similar method to that describing the preparation of Example 6, except using Example 8 as the starting material (1.92 g). Yield=1.25 g, 72%.

NMR (300 MHz, DMSO-D6): δ1.80(s, 3H), 2.45 (obscured by DMSO), 3.52(t, 1H), 3.65(t, 1H), 3.75(d of d, 1H), 4.10(m, 5H), 4.55(d, 1H), 4.70(m, 1H), 6.00(d, 1H), 7.24(d of d, 1H), 7.40(t, 1H), 7.47(d, 1H), 8.2(t, 1H).

MS: ESP+(M+H)=392.

EXAMPLE 10

N-((5S)-3-(4-(2,3-Dihydro-6H-pyran-4-yl)phenyl)-2-oxooxazolidin-5-ylmethyl)acetamide Triphenylarsine (61 mg), $Pd_2(dba)_3$ (45.8 mg) and lithium chloride (128 mg) were added to a stirred solution of Reference Example 3 (278 mg) in NMP (5 ml) and the vessel was purged well with argon. After stirring for 5 minutes at ambient temperature, Reference Example 1 (397 mg) was added and the reaction mixture was stirred at 40° C. for 24 hours. TLC (ethyl acetate) indicated complete reaction. A 2.0M aqueous potassium fluoride solution (1 ml) was added and the reaction mixture was stirred at ambient temperature for 30 minutes. Water was added and the product was extracted with ethyl acetate, with filtration of the two phase mixture. The organic phase was washed with water, brine, dried over anhydrous sodium sulfate and evaporated to a gum. The title compound was isolated by MPLC (Merck 9385 silica, using as eluant a mixture of acetonitrile (40%) and ethyl acetate), and was triturated with ether giving a crystalline powder (yield=104 mg, 33%).

NMR (300 MHz, DMSO-D6): δ1.83(t, 3H), 2.42(s, 2H), 3.40(m, 2H), 3.73(m, 1H), 3.80(t,2H), 4.10(t, 1H), 4.20(d, 2H), 4.70(m, 1H), 6.22(s, 1H), 7.47(AB, 4H), 8.23(t, 1H).

MS: ESP+(M+H)=317.

EXAMPLE 11

N-((5S)-3-(3-Fluoro-4-(2,3-dihydro-6H-pyran-4-yl)phenyl)-2-oxooxazolidin-5-ylmethyl)acetamide The title compound was prepared using a similar method to that describing the preparation of Example 10, except that N-((5S)-3-(3-fluoro-4-trimethyltinphenyl)-2-oxooxazolidin-5-ylmethyl)acetamide (415 mg, WO Patent 94-13649, 23.06.94) was used as the starting material and a reaction time of 2 days was required. Yield=130 mg, 39%.

NMR (300 MHz, DMSO-D6): δ1.82(t,3H), 2.40(s,2H), 3.40(m,2H), 3.71(d of d, 1H), 3.80(t, 2H), 4.10(t, 1H), 4.20(d, 2H), 4.73(m, 1H), 6.08(s, 1H), 7.28(d of d, 1H), 7.38(t, 1H), 7.47(d of d, 1H), 8.21(t, 1H).

MS: ESP+(M+H)=335.

EXAMPLE 12

N-((5S)-3-(3-Fluoro-4-(1-benzyl-1,2,5,6-tetrahydropyrid-4-yl)phenyl)-2-oxooxazolidin-5-ylmethyl)acetamide Reference Example 8 (6.9 g) was dissolved in TFA (10 ml) and heated briefly to reflux. The TFA was evaporated and the residue was basified with aqueous ammonium hydroxide solution and the product extracted with ethyl acetate. The organic phase was dried over anhydrous magnesium sulfate and evaporated to an oil which crystallized on trituration with ether to give the title compound (yield=3.78 g, 75% over 2 stages).

NMR(300 MHz DMSO-D6): δ1.81(s, 3H), 2.41(s, 2H), 2.60(m, 2H), 3.05(s, 2H), 3.40(m, 2H), 3.58(s, 2H), 3.72(m, 1H), 4.10(m, 1H), 4.70(m, 1H), 5.95(s, 1H), 7.31(m, 10H), 8.20(t, 1H).

MS: ESP+(M+H)=424.

EXAMPLE 13

(5R)-Hydroxymethyl-3-(3-fluoro-4-(N-benzyl-1,2,5,6-tetrahydropyrid-4-yl)phenyl)oxazolidin-2-one n-Butyllithium/hexane (28.1 ml of 1.40M) was slowly added to a stirred partial solution of Reference Example 7 (8.7 g) in dry THF (100 ml) at −70° C. under argon. The solution was stirred for 15 minutes, then a solution of R-glycidyl butyrate (3.04 g) in THF (15 ml) was added and the reaction mixture was allowed to warm to ambient temperature and stirred for 18 hours. The reaction mixture was quenched with water and extracted with ethyl acetate. The organic phase was washed with water, brine, dried over anhydrous sodium sulfate and evaporated to give the title compound as a gum which was isolated by MPLC (silica, using as eluant a mixture of methanol (5%) and dichloromethane) and recrystallised from acetonitrile. Yield=4.78 g, 58%.

NMR (300 MHz, DMSO-D6): δ2.43(s, 2H), 2.60(m, 2H), 3.05(s, 2H), 3.53(m, 1H), 3.58(s, 2H), 3.65(m, 1H), 3.80(d of d, 1H), 4.07(t, 1H), 4.70(m, 1H), 5.19(t, 1H), 5.95(s, 1H), 7.30(m, 7H), 7.47(d of d, 1H).

MS: ESP+(M+H)=383.

Analysis: Calculated for $C_{22}H_{23}N_2O_3F$: C, 69.0; H, 6.0; N, 7.3%.

Found: C, 69.2; H, 6.1; N, 7.4%.

EXAMPLE 14

N-((5S)-3-(3-Fluoro-4-(1-methoxyacetyl-1,2,5,6-tetrahydropyrid-4-yl)phenyl)-2-oxooxazolidin-5-ylmethyl)acetamide A solution of the hydrochloride salt of Example 7 (300 mg) and $NaHCO_3$ (340 mg) in acetone (8 ml)/water (4 m) was cooled to 0–4° C. and methoxyacetyl chloride (176 mg) was added dropwise. After stirring for 15 minutes additional $NaHCO_3$ and methoxyacetyl chloride (as above) were added giving complete reaction within 10 minutes. The reaction mixture was diluted with water and extracted with ethyl acetate. The organic phase was washed with saturated NaCl solution, dried over anhydrous $Na_2SO_4$ and evaporated to a gum. The title compound was isolated by MPLC (4% MeOH/$CH_2Cl_2$, Merck 9385 silica), and was triturated with ether (yield=236 mg, 72%).

NMR (300 MHz, DMSO-D6) δ: 1.80(s, 3H), 2.4(broad, 2H), 3.27(s, 3H+water), 3.38(t, 2H), 3.52(broad, 1H), 3.62 (broad, 1H), 3.71(q, 1H), 4.18(m, 5H), 4.70(m, 1H), 5.97(s, 1H), 7.25(d of d, 1H), 7.35(t, 1H), 7.45(d of d, 1H), 8.19(t, 1H).

MS: ESP+(M+H)=406.

The hydrochloride salt of Example 7 was prepared by the reaction in dry dichloromethane at 0–4° C. of Example 12 (16.6 g) with 1-chloroethyl chloroformate (6.73 g, added dropwise), in the presence of triethylamine (0.59 g). After reaction for 0.5 hours the solvent was removed under vacuum and the residue refluxed with methanol (100 ml) for 0.5 hours. The methanol was removed under vacuum and the residue recrystallised from ethanol (250 ml) to yield the hydrochloride salt of Example 7 (11.92 g, 82%, NMR as previously assigned for Example 7).

EXAMPLE 15

N-((5S)-3-(3-Fluoro-4-(1-methyloxalyl-1,2,5,6-tetrahydropyrid-4-yl)phenyl)-2-oxooxazolidin-5-ylmethyl)acetamide The hydrochloride salt of Example 7 (300 mg) was suspended in ethyl acetate, washed with aqueous ammonia, dried over anhydrous $Na_2SO_4$ and evaporated to give the free base of Example 7. Triethylamine (152 mg) was added to a mixture of the resulting free base of Example 7 in dichloromethane (10 ml), followed by the addition of methyloxalyl chloride (123 mg). Reaction was complete after 10 minutes. The reaction mixture was washed with 2N HCl, water, aqueous ammonia and saturated NaCl. The organic phase was dried over anhydrous $Na_2SO_4$ and evaporated to a gum. The title compound was isolated by MPLC (4% MeOH/$CH_2Cl_2$, Merck 9385 silica), and was triturated with ether (yield=181 mg, 53%).

NMR (300 MHz, DMSO-D6) δ: 1.79(s, 1H), 2.50 (obscured by solvent), 3.38(t, 2H), 3.55(t, 1H), 3.70(m, 2H), 3.82(d, 3H), 4.05(s, 1H), 4.12(m, 2H), 4.70(m, 1H), 5.98(d, 1H), 7.95(d of d, 1H), 7.35(t, 1H), 7.45(d of d, 1H), 8.19(t, 1H).

MS: ESP+(M+H)=420.

EXAMPLE 16

N-((5S)-3-(3-Fluoro-4-(-ethylaminocarbonyl-1,2,5,6-tetrahydropyrid-4-yl)phenyl)-2-oxooxazolidin-5-ylmethyl)acetamide Triethylamine (101 mg), followed by ethyl isocyanate (71 mg) were added to a stirred suspension of the hydrochloride salt of Example 7 (300 mg) in THF (10 ml). After stirring for 2 hours, additional triethylamine and ethyl isocyanate (as above) were added, giving complete reaction after 3 days at ambient temperature. The reaction mixture was washed with 2N HCl, water, saturated $NaHCO_3$ solution and saturated NaCl solution. Crystallised product was filtered off. The organic phase was dried over anhydrous $Na_2SO_4$ and evaporated to give a crystalline solid. The combined product was purified by MPLC (using a mixture of methanol and dichloromethane of increasing polarity as eluant, Merck 9385 silica), and was triturated with ether to give the title compound (222 mg, 68%).

NMR (300 MHz, DMSO-D6) δ: 1.00(t, 3H), 1.80(s, 3H), 2.37(broad, 2H), 3.05(6 line, 2H), 3.38(t, 2H), 3.47(t, 2H), 3.71(q, 1H), 3.92(broad, 2H), 4.10(t, 1H), 4.70(t, 1H), 5.98(s, 1H), 6.72(m, 1H), 7.25(d of d, 1H), 7.35(t, 1H), 7.45(d of d, 1H), 8.20(t, 1H).

MS: ESP+(M+H)=405.

EXAMPLE 17

N-((5S)-3-(3-Fluoro-4-(1-acetoacetyl-1,2,5,6-tetrahydropyrid-4-yl)phenyl)-2-oxooxizolidin-5-ylmethyl)acetamide Triethylamine (202 mg), followed by diketene (227 mg) were added to a stirred suspension of the hydrochloride salt of Example 7 (665 mg) in dichloromethane (15 ml). The starting material dissolved and a precipitate of product began to separate after 15 minutes. The reaction was complete after 30 minutes. The precipitate was filtered off, washed with dichloromethane and recrystallised from acetonitrile to give the title compound (520 mg, 69%).

NMR (300 MHz, DMSO-D6) δ: 1.81(s, 3H), 2.15(d, 3H), 2.40(broad, 2H), 3.39(t, 2H), 3.50(t, 1H), 3.70(m, 4H), 4.10(m, 3H), 4.72(m, 1H), 5.98(d, 1H), 7.25(d of d, 1H), 7.38(t of d, 1H), 7.45(d, 1H), 8.20(t, 1H).

MS: ESP+(M+H)=418.

EXAMPLE 18

N-((5S)-3-(3-Fluoro-4-(1-(2-{2-methoxyethoxy}ethoxy)methylcarbonyl-1,2,5,6-tetrahydropyrid-4-yl)phenyl-2-oxooxazolidin-5-ylmethyl)acetamide N-Methylmorpholine (101 mg), 2-[2-(2-methoxyethoxy)ethoxy]acetic acid (154 mg) and N-hydroxybenzotriazole (122 mg, allowing for 5% water) were added to a mixture of the hydrochloride salt of Example 7 (277 mg) and DMF (5 ml). The mixture was stirred for 5 minutes at ambient temperature and then 1-ethyl-3-dimethylaminopropyl-carbodiimide (165 mg) was added and the mixture stirred for 18 hours. The solvent was evaporated under high vacuum and the residue partially purified by MPLC [using a mixture of methanol and dichloromethane increasing in polarity from 5% to 25% methanol as eluant, Merck 9385 silica]. Final purification by reverse-phase MPLC [using a mixture of acetonitrile and water, increasing in acetonitrile from 0% to 25% as eluant, HP20SS resin] and trituration with ether gave the title compound (11 mg, 30%).

NMR (300 MHz, DMSO-D6) δ: 1.80(s, 1H), 1.86(s, 1H), 2.43(partially obscured), 3.20(s, 2H), 3.40(m, 3H), 3.55(m, 10H), 3.72(m, 1H), 4.08(m, 3H), 4.20(s, 2H), 4.70(m, 1H), 6.00(s, 1H), 7.26(d, 1H), 7.35(t, 1H), 7.45(d, 1H), 8.20(t, 1H).

MS: ESP+(M+H)=494.

EXAMPLE 19

N-((5S)-3-(3-Fluoro-4-(1-formyl-1,2,5,6-tetrahydropyrid-4-yl)phenyl)-2-oxooxazolidin-5-ylmethyl)acetamide In an analogous manner to that described in Example 15, the hydrochloride salt of Example 7 (370 mg) was converted to the free base, which was then refluxed with ethyl formate (25 ml) for 24 hours. The reaction mixture was evaporated and the title compound was isolated by MPLC (5% MeOH/CH$_2$Cl$_2$ eluant, Merck 9385 silica). The title product crystallised on trituration with ether (297 mg, 82%).

NMR (300 MHz, DMSO-D6) δ: 1.80(s, 1H), 2.43(m, 2H), 3.40(t, 2H), 3.58(m, 2H), 3.72(q, 1H), 4.02(d, 1H), 4.07(s, 1H), 4.11(t, 1H), 4.72(m, 1H), 5.98(d, 1H), 7.25(d of d, 1H), 7.35(t, 1H), 7.45(d of d, 1H), 8.12(d, 1H), 8.20(t, 1H).

MS: ESP+(M+H)=362.

EXAMPLE 20

N-((5S)-3-(3-Fluoro-4-(1-acetylaminoacetyl-1,2,5,6-tetrahydropyrid-4-yl)phenyl)-2-oxooxazolidin-5-ylmethyl)acetamide N-Methylmorpholine (101 mg), N-acetylglycine (101 mg) and N-hydroxybenzotriazole (122 mg, allowing for 5% water) were added to a mixture of the hydrochloride salt of Example 7 (277 mg) and DMF (5 ml). The mixture was stirred for 5 minutes at ambient temperature then 1-ethyl-3-dimethylaminopropyl-carbodiimide (165 mg) was added and the mixture was stirred for 18 hours. The solvent was evaporated under high vacuum and the title compound was isolated by MPLC (using a mixture of methanol and dichloromethane increasing in polarity from 4–10% methanol as eluant, Merck 9385 silica). The title product crystallised on trituration with ether (270 mg, 83%).

NMR (300 MHz, DMSO-D6) δ: 1.80(s, 1H), 1.86(s, 1H), 2.45(partially obscured), 3.39(t, 2H), 3.60(m, 2H), 3.72(q, 1H), 3.95(d of d, 2H), 4.10(m, 3H), 4.72(m, 1H), 5.99 (broad, 1H), 7.25(d of d, 1H), 7.38(t of d, 1H), 7.45(d, 1H), 7.96(broad, 1H), 8.20(t, 1H).

MS: ESP+(M+H)=433.

EXAMPLE 21

N-((5S)-3-(3-Fluoro-4-(-acetylacetoxyacetyl-1,2,5,6-tetrahydropyrid-4-yl)phenyl)-2-oxooxazolidin-5-ylmethyl)acetamide 4-Dimethylaminopyridine (4 mg) followed by diketene (118 mg) were added to a stirred solution of the Example 9 (261 mg) in dry dichloromethane (10 ml). After stirring for 30 minutes at ambient temperature the reaction mixture was evaporated and the title compound was isolated by MPLC (5% MeOH/CH$_2$Cl$_2$ eluant, Merck 9385 silica). The title product crystallised on trituration with ether (255 mg, 80%).

NMR (300 MHz, DMSO-D6) δ: 1.80(s, 3H), 2.22(s, 3H), 2.50(obscured), 3.40(t, 2H), 3.55(t, 1H), 3.64(s, 3H), 3.73(q, 1H), 4.07(m, 3H), 4.68(m, 1H), 4.87(d, 2H), 6.13(broad, 1H), 7.46(m, 4H), 8.20(t, 1H).

MS: ESP+(M+H)=458.

EXAMPLE 22

N-((5S)-3-(3-Fluoro-4-(1-(2-methyl-2-phenylamino)ethenylcarbonyl-1,2,5,6-tetrahydropyrid-4-yl)phenyl)-2-oxooxazolidin-5-ylmethyl)acetamide A mixture of Example 17 (104 mg), aniline (47 mg), p-toluenesulfonic acid (p-TSA) (5 mg) and ethanol (ca. 10 ml) was stirred under reflux for 24 hours. Additional aniline (233 mg) and p-TSA (5 mg) were added, together with 3A molecular sieve powder (1 g) and reflux continued for a further 24 hours. The reaction mixture was filtered, evaporated. MPLC [using a mixture of acetonitrile and ethyl acetate, increasing in acetonitrile from 25% to 50% as eluant], and trituration with ether gave the title compound (43 mg, 35%).

NMR (300 MHz, DMSO-D6) δ: 1.82(s, 3H), 2.05(s, 3H), 2,45(obscured), 3.40(q, 2H), 3.70(m, 3H), 4.14(m, 3H), 4.72(m, 1H), 5.08(s, 1H), 6.04(s, 1H), 7.10(m, 3H), 7.37(m, 5H), 8.20(t, 1H), 11.67(s, 1H).

MS: ESP+(M+H)=493.

EXAMPLE 23

There is no compound with Example No. 23.

EXAMPLE 24

N-((5S)-3-(3-fluoro-4-(1-cyano-1,2,5,6-tetrahydropyrid-4-yl)phenyl)-2-oxooxazolidin-5-ylmethyl)acetamide 4-Dimethylaminopyridine (24 mg), triethylamine (606 mg) and a solution of cyanogen bromide (1.06 g) in dichloromethane (5 ml) were added to a stirred suspension of the hydrochloride salt of Example 7 (739 mg) in dry dichloromethane (15 ml). After stirring for 1 hour at ambient temperature, a solution had formed and the reaction was complete. The reaction mixture was washed with 2N HCl, aqueous $NaHCO_3$ and dried over anhydrous $Na_2SO_4$. The mixture was evaporated to give a gum which crystallised on trituration with ether (488 mg, 68%).

NMR (300 MHz, DMSO-D6) δ: 1.81(s, 3H), 2.50(d, obscured), 3.39(t, 4H), 3.71(q, 1H), 3.92(d, 2H), 4.11(t, 1H), 4.72(m, 1H), 5.95(s, 1H), 7.27(d of d, 1H), 7.35(t, 1H), 7.47(d of d, 1H), 8.20(t, 1H).

MS: ESP+(M+H)=359.

EXAMPLE 25

N-((5S)-3-(3-Fluoro-4-(1-{pyrimid-2-yl}-1,2,5,6-tetrahydropyrid-4-yl)phenyl)-2-oxooxazolidin-5-ylmethyl)acetamide A stirred mixture of the hydrochloride salt of Example 7 (1.29 g), $NaHCO_3$ (1.18 g) and 2-chloropyrimidine (601 mg) was heated under reflux for 5 hours. The solvent was evaporated and the residue was taken into ethyl acetate and washed with water and brine. The organic phase was dried over anhydrous $Na_2SO_4$ and evaporated. The title compound was isolated by MPLC (using a mixture of acetonitrile and ethyl acetate increasing in polarity from 50% to 65% acetonitrile as eluant, Merck 9385 silica), and was triturated with ether (939 mg, 65%).

NMR (300 MHz, DMSO-D6) δ: 1.82(s, 3H), 2.50 (obscured), 3.40(t, 2H), 3.70(q, 1H), 3.95(t, 2H), 4.10(t, 1H), 4.30(q, 2H), 4.70(m, 1H), 6.10(s, 1H), 6.62(t, 1H), 7.27(d of d, 1H), 7.39(t, 1H), 7.47(d of d, 1H), 8.20(t, 1H), 8.37(d, 2H).

MS: ESP+(M+H)=412.

EXAMPLE 26

N-((5S)-3-(3-Fluoro-4-(1-{tetrazole-5-yl}-1,2,5,6-tetrahydropyrid-4-yl)phenyl)-2-oxooxazolidin-5-ylmethyl)acetamide Azidotrimethylsilane (154 mg) and dibutyltin oxide (97 mg) were added to a stirred suspension of Example 24 (240 mg) in dry toluene (10 ml), and the mixture stirred at 70° C. for 18 hours. On cooling, methanol (5 ml) was added and after stirring for 10 minutes the solvent was evaporated. The title compound was isolated by MPLC (20% MeOH/$CH_2Cl_2$. Merck 9385 silica) and crystallised on evaporating the fractions to a small volume. The title product was filtered off washed with a little cold methanol (150 mg, 56%).

NMR (300 MHz, DMSO-D6) δ: 1.80(s, 3H), 2.55(s, 2H), 3.30(obscured, 1H), 3.39(t, 2H), 3.63(t, 2H), 3.73(q, 1H), 4.05(d, 2H), 4.12(t, 1H), 4.62(m, 1H), 6.08(s, 1H), 7.27(d of d, 1H), 7.39(t, 1H), 7.47(d of d, 1H), 8.19(t, 1H).

MS: ESP+(M+H)=402.

EXAMPLE 27

There is no compound with Example No. 27.

EXAMPLE 28

There is no compound with Example No. 28.

EXAMPLE 29

N-((5S)-3-(3-Fluoro-4-(1-methylsulfonyl-1,2,5,6-tetrahydropyrid-4-yl)phenyl)-2-oxooxazolidin-5-ylmethyl)acetamide Triethylamine (242 mg), followed by methanesulfonyl chloride (115 mg) were added to a stirred suspension of the hydrochloride salt of Example 7 (296 mg) in dichloromethane (10 ml). After stirring for 30 minutes, additional triethylamine and methanesulfonyl chloride (as above) were added giving a solution, and complete reaction after a further 30 minutes at ambient temperature. The reaction mixture was washed with 2N HCl, water, saturated $NaHCO_3$ and saturated NaCl. The organic phase was dried over anhydrous $Na_2SO_4$ and evaporated to give a crystalline solid. This was purified by MPLC (using 5% MeOH/$CH_2Cl_2$ as eluant, Merck 9385 silica) and triturated with ether to give the title compound (209 mg, 64%).

NMR (300 MHz, DMSO-D6) δ: 1.80(s, 3H), 2.55(s, 2H), 2.93(s, 3H), 3.35(m, 4H), 3.72(q, 1H), 3.85(d, 2H), 4.11(t, 1H), 4.72(m, 1H), 6.02(s, 1H), 7.27(d of d, 1H), 7.39(t, 1H), 7.47(d of d, 1H), 8.20(t, 1H).

MS: ESP+(M+H)=412.

EXAMPLE 30

N-((5S)-3-(4-(1-Decyloxyacetyl-1,2,5,6-tetrahydropyrid-4-yl)phenyl)-2-oxooxazolidin-5ylmethyl)acetamide Sodium hydride (29 mg, 60% in mineral oil) was added to a stirred solution of Example 6 (242 mg) in dry DMF (5 ml). There was an effervescence and a precipitate formed. After 5 minutes, decyl iodide (209 mg) was added and the reaction mixture was stirred for 24 hours at ambient temperature. Additional sodium hydride and decyl iodide (as above) were added giving almost complete reaction after a further 24 hours. The reaction mixture was diluted with water and extracted with ethyl acetate. The organic phase was washed with water and saturated NaCl, was dried over anhydrous $Na_2SO_4$ and evaporated to give a gum. The title compound was isolated by MPLC (using 3.5% MeOH/$CH_2Cl_2$ as eluant Merck 9385 silica), and was triturated with ether. Yield=132 mg, 40%.

MS: ESP+(M+H)=514.

The title compound was characterised by an HPLC retention time of 23.30 mins., using the HPLC conditions described in Example 35.

EXAMPLE 31

N-((5S)-3-(4-(1-Butyryloxyacetyl-1,2,5,6-tetrahydropyrid-4-yl)phenyl)-2-oxooxazolidin-5-ylmethyl)acetamide Triethylamine (101 mg) was added to a stirred solution of Example 6 (242 mg) in dichloromethane (10 ml), followed by the dropwise addition of butyryl chloride (76 mg) in dichloromethane (0.2 ml). After stirring for 30 minutes, additional triethylamine and butyryl chloride (as above) were added giving complete reaction after a further 30 minutes at ambient temperature. The reaction mixture was washed with 2N HCl, water, saturated NaHCO$_3$ and saturated NaCl. The organic phase was dried over anhydrous Na$_2$SO$_4$ and evaporated to a crystalline solid. This was purified by MPLC (using 4% MeOH/CH$_2$Cl$_2$ as eluant, Merck 9385 silica) and triturated with ether to give the title compound. Yield=237 mg, 82%.

NMR (300 MHz, DMSO-D6) δ: 0.90(t, 3H), 1.55(m, 2H), 1.81 (s, 3H), 2.32(t, 2H) 2.55(obscured), 3.40(t, 2H), 3.56(t, 1H), 3.64(t, 1H), 3.75(q, 1H), 4.10(m, 3H), 4.69(m, 1H), 4.83(d, 2H), 6.15(broad, 1H), 7.48(m, 4H), 8.20(t, 1H).

MS: ESP+(M+H)=443.

EXAMPLE 32

N-((5S)-3-(4-(1-Decanoyloxyacetyl-1,2,5,6-tetrahydropyrid-4-yl)phenyl)-2-oxooxazolidin-5-ylmethyl)acetamide Using an analogous procedure to that described in Example 31, Example 6 was acylated with decanoyl chloride (2×149 mg) to give the title compound. Yield=268 mg, 78%.

NMR (300 MHz, DMSO-D6) δ: 0.90(t, 3H), 1.23(s, 12(H), 1.55(m, 2H), 1.81(s, 3H), 2.32(t, 2H), 2.55 (obscured), 3.40(t, 2H), 3.56(t, 1H), 3.64(t, 1H), 3.75(q, 1H), 4.10(m, 3H), 4.69(m, 1H), 4.83(d, 2H), 6.15(broad, 1H), 7.48(m, 4H), 8.20(t, 1H).

MS: ESP+(M+H)=528.

EXAMPLE 33

N-((5S)-3-(4-(1-Ethylaminocarboxyacetyl-1,2,5,6-tetrahydropyrid-4-yl)phenyl-2-oxooxazolidin-5-ylmethyl)acetamide Triethylamine (101 mg), followed by ethyl isocyanate (142 mg) were added to a stirred solution of Example 6 (298 mg) in dichloromethane (10 ml). After stirring for 18 hours at ambient temperature, additional triethylamine and ethyl isocyanate (as above) were added giving complete reaction after a further 24 hours. A precipitate of product was filtered off and a second crop was obtained on reducing the volume. The combined material was recrystallised from ethanol to give the title compound. Yield=251 mg, 71%.

NMR (300 MHz, DMSO-D6) δ: 1.00(t, 3H), 1.80(s, 3H), 2.50(obscured), 3.00(m, 2H), 3.40(t, 2H), 3.55(t, 1H), 3.65 (t, 1H), 3.73(q, 1H), 4.07(m, 3H), 4.68(m 3H), 6.13(broad, 1H), 7.27(broad, 1H), 7.50(m, 4H), 8.21(t, 1H).

MS: ESP+(M+H)=445.

EXAMPLE 34

N-((5S)-3(4-(1-Benzyloxyacetyloxyacetyl-1,2,5,6-tetrahydropyrid-4-yl)phenyl)-2-oxooxazolidin-5-ylmethyl)acetamide Using an analogous procedure to that described in Example 31, Example 6 was acylated on a 2.0 mM scale with benzyloxyacetyl chloride (3×461 mg) to give the title compound. Yield=705mg, 68%.

NMR (300 MHz, DMSO-D6) δ: 1.82(s, 3H), 2.50 (obscured), 3.40(t, 2H), 3.58(t, 1H), 3.66(t, 1H), 3.73(q, 1H), 4.10(m, 3H), 4.24(s, 2H), 4.58(s, 2H), 4.70(m, 1H), 4.95(d, 2H), 6.15(broad, 1H), 7.35(m, 5H), 7.50(m, 4H), 8.20(t, 1H).

MS: ESP+(M+H)=522.

EXAMPLE 35

N-((5S)-3-(4-(1-{4-t-Butylcyclohexylcarbonyl}-1,2,5,6-tetrahydropyrid-4-yl)phenyl)-2-oxooxazolidin-5-ylmethyl)acetamide Using an analogous procedure to that described in Example 20, the TFA salt of Example 2 was reacted with 4-tert-butylcyclohexanecarboxylic acid in place of N-acetylglycine, to give the title compound. Yield=208 mg, 58%.

MS: ESP+(M+H)=482.

The tide compound was characterised by an HPLC retention time of 21.72 mins., using the following HPLC conditions: Column: Hypersil ODS 5 m; Flow rate: 1.5 ml/min.; UV: 254 nm; gradient parameters: Solvent A 1 mM TFA/water, Solvent B 1 mM TFA/acetonitrile; time 0 95% A/5% B; time 3 mins. 95% A/5% B; time 17 mins. 5% A/95% B; time 19 mins 95% A/5% B; time 20 mins 95% A/5% B.

EXAMPLE 36

N-((5S)-3-(4-(1-{2-Hydroxy-decanoyl}-1,2,5,6-tetrahydropyrid-4-yl)phenyl)-2-oxooxazolidin-5-ylmethyl)acetamide Using an analogous procedure to that described in Example 20, the TFA salt of Example 2 was reacted with 2-hydroxydecanoic acid in place of N-acetylglycine, to give the title compound. Yield=252 mg, 65%.

MS: ESP+(M+H)=514.

The title compound was characterised by an HPLC retention time of 22.80 mins., using the HPLC conditions described in Example 35.

EXAMPLE 37

N-((5S)-3-(4-(1-{Pyrimid-2-yl}-1,2,5,6-tetrahydropyrid-4-yl)phenyl)-2-oxooxazolidin-5-ylmethyl)acetamide Using an analogous procedure to that described in Example 25, the TFA salt of Example 2 was reacted on a 1.5 mM scale with 2-chloropyrimidine, to give the title compound. Yield=220 mg, 36%.

NMR (300 MHz, DMSO-D6) δ: 1.80(s, 3H), 2.50 (obscured), 3.40(t, 2H), 3.73(q, 1H), 3.98(t, 2H), 4.10(t, 1H), 4.30(d, 2H), 4.69(m, 1H), 6.25(s, 1H), 6.62(t, 1H), 7.48(m, 4H), 8.20(t, 1H), 8.37(d, 2H).

MS: ESP+(M+H)=394.

EXAMPLE 38

N-((5S)-3-(4-(1-p-Toluenesulfonyl-1,2,5,6-tetrahydropyrid-4-yl)phenyl)-2-oxooxazolidin-5-ylmethyl)acetamide Triethylamine (202 mg), followed by p-toluenesulfonyl chloride (171 mg) were added to a stirred suspension of the TFA salt of Example 2 (322 mg) in dichloromethane (10 ml). After stirring for 30 minutes at ambient temperature, the reaction mixture had become a solution and the reaction was complete. The solution was washed with 2N HCl, water, saturated NaHCO$_3$ and saturated NaCl. The organic phase was dried over anhydrous Na$_2$SO$_4$ and evaporated to give a crystalline solid which was triturated with ether to give the title compound. Yield=306 mg, 87%.

NMR (300 MHz, DMSO-D6) δ: 1.79(s, 3H), 2.35(s, 3H), 2.50(obscured), 3.17(m, 2), 3.38(m, 2H), 3.64(broad, 2H), 3.70(m, 1H), 4.08(m, 1H), 4.68(m, 1H), 6.05(broad, 1H), 7.40(m, 6H), 7.68(m, 2H), 8.20(t, 1H).

MS: ESP+(M+H)=470.

EXAMPLE 39

N-((5S)-3-(4-(1-Hydroxyacetyl-1,2,3,4,5,6-hexahydropyrid-4-yl)phenyl)-2-oxooxizolidin-5-ylmethyl)acetamide A mixture of Example 6 (242 mg) and ethanol (10 ml) was hydrogenated over 10% palladium on charcoal (25 mg) at atmospheric pressure for 3 hours. The catalyst was removed by Millipore filtration and the solvent was evaporated leaving an oil which crystallised on trituration with ether to give the title compound. Yield=230 mg, 95%.

NMR (300 MHz, DMSO-D6) δ: 1.50(m, 2H), 1.75(m, 2H), 1.80(s, 3H), 2.70(m, 2H), 3.04(t, 1H), 3.37(t, 2H), 3.73(m, 2H), 4.09(m, 3H), 4.25(m, 2H), 4.69(m, 1H), 7.23 (d, 2H), 7.42(d, 2H), 8.20(t, 1H).

MS: ESP+(M+H)=376.

EXAMPLE 40

N-((5S)-3-(3-Fluoro-(2,3,4,5-tetrahydropyran-4-yl)phenyl)-2-oxooxazolidin-5-ylmethyl)acetamide Using an analogous procedure to that described in Example 39, Example 11 was hydrogenated on a 0.6 mM scale to give the title compound in quantitative yield.

NMR (300 MHz, DMSO-D6) δ: 1.65(m, 4H), 1.80(s, 3H), 3.00(m, 1H), 3.36(t, 2H), 3.44(d of d, 2H), 3.70(d of d, 1H), 3.90(d of d, 2H), 4.07(t, 1H), 4.70(m, 1H), 7.23(d of d, 1H), 7.32(t, 1H), 7.41(d of d, 1H), 8.20(t, 1H).

MS: ESP+(M+H)=337.

EXAMPLE 41

N-((5S)-3-(3,5-Difluoro-(2,3,4,5-tetrahydropyran-4-yl)phenyl)-2-oxooxazolidin-5-ylmethyl)acetamide Using an analogous procedure to that described in Example 39, Example 47 was hydrogenated on a 4.23 mM scale to give the title compound (1.38 g, 93%).

NMR (300 MHz, DMSO-D6) δ: 1.55(d of d, 2H), 1.95(m, 2H), 3.13(m, 1H), 3.38(m, 4H), 3.69(q, 1H), 3.91(d of d, 2H), 4.08(t, 1H), 4.72(m, 1H), 7.25(d, 2H), 8.18(t, 1H).

MS: ESP+(M+H)=355.

EXAMPLE 42

N-((5S)-3-(3-Fluoro-4-(1-hydroxyacetyl-1,2,3,4,5,6-hexahydropyrid-4-yl)phenyl)-2-oxooxazolidin-5-ylmethyl)acetamide Using an analogous procedure to that described in Example 39, Example 9 was hydrogenated on the scale of Example 39 to give the title compound (236 mg, 92%).

NMR (300 MHz, DMSO-D6) δ: 1.60(m, 4H), 1.80(s, 3H), 2.69(t, 1H), 3.04(m, 2H), 3.39(t, 2H), 3.73(m, 2H), 4.08(m, 3H), 4.48(m, 2H), 4.70(m, 1H), 7.20(d of d, 1H), 7.30(t, 1H), 7.43(d of d, 1H), 8.19(t, 1H).

MS: ESP+(M+H)=394.

EXAMPLE 43

N-((5S)-3-(4-(1-Hydroxyacetyloxyacetyl-1,2,3,4,5,6-hexahydropyrid-4-yl)phenyl)-2-oxooxazolidin-5-ylmethyl)acetamide A mixture of Example 34 (261 mg) and ethanol (10 ml) was hydrogenated over 10% palladium on charcoal (125 mg) at atmospheric pressure for 3 days. The catalyst was removed by Millipore filtration and the solvent was evaporated leaving an oil which crystallised on trituration with ether to give the title compound. Yield=179 mg, 83%.

NMR (300 MHz, DMSO-D6) δ: 1.55(m, 4H), 1.82(s, 3H), 2.70(m, 2H), 3.10(m, 1H), 3.39(t, 2H), 3.70(q, 1H), 3.80(m, 1H), 4.09(m, 3H), 4.41(m, 1H), 4.69(m, 1H), 4.84(s, 2H), 5.40(t, 1H), 7.24(d, 2H), 7.44(d, 2H), 8.20(t, 1H).

MS: ESP+(M+H)=434.

EXAMPLE 44

N-((5S)-3-(3,5-Difluoro-4-(1,2,5,6-tetrahydronyrid-4-yl)phenyl)-2-oxooxazolidin-5-ylmethyl)acetamide.

N-BOC-acetamide (3.1 g, Chem. Pharm. Bull., 36, 3125 (1988)) was added to a solution of Reference Example 11 (5.3 g) in THF (100 ml), and the mixture cooled in an ice-bath. Tributyl phosphine (4.8 ml, 3.89 g) and 1,1'-(azodicarbonyl)-dipiperidine (4.9 g) were added and the mixture allowed to stir at ice-bath temperature for 30 minutes after which a precipitiate was evident. The reaction was then stirred overnight at ambient temperature. After filtration and evaporation in vacuo the residue was purified on silica gel using a 1:1 mixture of isohexane and ethyl acetate as eluant to give a solid (6.77 g). The solid was dissolved in TFA (10 ml) and refluxed for a few minutes. The TFA was removed in vacuo and the residue dissolved in a mixture of ethyl acetate and methanol. The solvent was evaporated and trituration with ether gave the title product (3.5 g, 58%) as the TFA salt (58%). The filtrate gave a further impure gum (1.25 g) which was suitable for further conversions.

NMR (300 MHz, DMSO-D6)d: 2.50(broad s, 2H), 3.40(t, 2H), 3.71(q, 1H), 3.77(broad s, 2H), 4.11(t, 1H), 4.74(m, 1H), 5.89(broad s, 1H),7.34(d, 1H), 8.20(t, 1H), 8.94(broad s, 2H).

EXAMPLE 45

N-((5S)-3-(3,5-Difluoro-4-(1-acetoxymethylcarbonyl-1,2,5,6-tetrahydropyrid-4-yl)phenyl)-2-oxooxazolidin-5-ylmethyl)acetamide Using an analogous reaction and work-up procedure to that described in Example 5, the TFA salt of Example 44 and acetoxy-acetylchloride were reacted on a 7.16 mM scale to give the title compound. Yield=2.62 g, 81%.

NMR (300 MHz, DMSO-D6) δ: 1.81(s, 3H), 2.08(s, 3H), 2.30(broad s, 1H), 2.40(broad s, 1H), 3.40(t, 2H), 3.55(t, 1H), 3.64(t, 1H), 3.72(q, 1H), 4.08(m, 3H), 4.74(m, 1H), 4.83(d, 2H), 5.85(m, 1H), 7.30(d, 2H), 8.20(t, 1H).

MS: ESP+(M+H)=452.

EXAMPLE 46

N-((5S)-3-(3,5-Difluoro-4-(1-hydroxyacetyl-1,2,5,6-tetrahydro -4-pyridyl)phenyl)-2-oxooxazolidin-5-ylmethyl)acetamide Using an analogous procedure to that described in Example 6, Example 45 (0.5 g) was converted to the title compound (solid 0.38 g, 84%).

NMR (300 MHz, DMSO-D6)d: 1.81(s, 3H), 2.33(broad d, 2H), 3.38(t, 2H), 3.51(t, 1H), 3.66(t, 1H), 3.70(q, 1H), 4.08(m, 3H), 4.12(t, 2H), 4.58(broad d, 1H), 4.74(m, 1H), 5.85(d, 1H), 7.30(d, 2H), 8.20(t, 1H).

MS: ESP+(M+H)=410.

EXAMPLE 47

N-((5S)-3-(3,5-Difluoro-4-(2,3-dihydro-6H-pyran-4-yl)phenyl)-2-oxooxazolidin-5-ylmethyl)acetamide N-BOC-acetamide (5.37 g, Chem. Pharm. Bull., 36, 3125 (1988)), followed by tributyl phosphine (8.3m}) and 1,1'-(azodicarbonyl)-dipiperidine (8.52 g) were added to a stirred mixture of Reference Example 14 (7.0 g) and anhydrous THF (200 ml) in an ice-bath. The mixture was stirred for a further 30 minutes at 0–5° C. and then stirred to ambient temperature over-night. The mixture was filtered, the solid washed with THF and the combined filtrates evaporated in vacuo and purified on silica gel (using a 4:6 mixture of isohexane and ethyl acetate as eluant). There was thus obtained an oil, which was dissolved in TFA (20 ml) by slow addition of TFA to the oil, refluxed briefly for few minutes and evaporated in vacuo. The residue was taken up in ethyl acetate (200 ml) washed with saturated $NaHCO_3$ the extracts counter-washed and the combined organic extracts evaporated in vacuo. The residue was purified on silica gel (using a mixture of 5% methanol and dichloromethane as eluant) to give the title compound as a solid (5.4 g, 68%).

NMR (300 MHz, DMSO-D6)d: 1.82(s, 3H), 2.26(broad s, 2H), 3.18(t, 2H), 3.70(q, 1H), 3.78(t, 2H), 4.10(t, 1H), 4.18(q, 2H), 4.65(m, 1H), 5.89(s, 1H), 7.26(s, 1H), 7.33(s, 1H), 8.19(t, 1H).

MS: ESP+(M+H)=353.

EXAMPLE 48

N-((5S)-3-(4-(2-Methyl-3,6- and -5,6-dihydropyran-4-yl)phenyl)-2-oxooxazolidin-5-ylmethyl)acetamide Reference Example 15 (0.49 g), palladium(0)bis(dibenzylideneacetone) (0.86 g), triphenylarsine (0.115 g) and lithium chloride (0.24 g) were dissolved in degassed N-methyl morpholine (33 ml). The stannane (Reference Example 1) (0.75 g) was added and the solution stirred at 40° C. for 18 hours. The mixture was then treated with aqueous potassium fluoride (5 ml, 2M), stirred for 0.5 hours and filtered through Celite. The solution was drowned with water (250 ml) and extracted with ethyl acetate(2×30 ml). The combined organics were washed with water (2×100 ml), dried and evaporated to the crude product (0.333 g, 54%) which was purified by firstly silica-gel MPLC [using a mixture of 2% MeOH and $CH_2Cl_2$ as eluant] and then preparative TLC [using a mixture of 13% MeOH and $CH_2Cl_2$ as eluant] to give the title mixture of 2-methyl regioisomers (0.054 g, 9%).

NMR (300 MHz, CDCl$_3$)d: 1.30–1.39 (m, 3H), 2.00–2.05 (s/s, 3H), 2.27–2.39 (broad m, 1.5H), 2.57–2.69 (m, 0.5H), 3.57–3.97 (4H, m), 4.00–4.20 (m, 4.30–4.40 (m, 1H), 4.72–4.81 (m, 1H), 6.00 (s,0.5H), 6.05–6.10 (m, 0.5H), 6.40 (broad s, 1H,), 7.39 (dd, 2H) and 7.45 (d, 2H).

MS: ESP+(M+H)=331.

EXAMPLE 49

N-((5S)-3-(4-(2,6-Dimethyl-2,3-dihydro-6H-pyran-4-yl)phenyl)-2-oxooxazolidin-5-ylmethyl)acetamide Reference Example 18 (0.656 g), palladium(0)bis(dibenzylideneacetone) (0.123 g), triphenylamine (0.164 g) and lithium chloride (0.338 g) were dissolved in degassed N,N-dimethylformamide (18 ml). The stannane (Reference Example 1) (1.07 g) was added after 5 minutes and stirring was continued for 19 hours at 40° C. Aqueous potassium fluoride (6.3 ml, 2M) was added and stirring continued for 15 minutes whereupon the mixture was filtered through Celite and evaporated to an oil. The oil was purified by silica-gel MPLC [using a mixture of ethyl acetate and isohexane increasing in polarity from 75% to 100% ethyl acetate as eluant] to afford a foam which was triturated with diethyl ether to give the title compound as a powder (0.679 g, 78%).

NMR (300 MHz, CDCl$_3$)d: 1.33 and 1.35 (d/d, each 3H), 2.01 (s, 3H), 2.28–2.35 (m, 2H), 3.55–3.82 (m, 4H), 4.05 (t, 1H), 4.36–4.25 (m, 1H), 4.72–4.82 (m, 1H), 6.00 (d, 1H), 6.01–6.10 (m, 1H), 7.40 (d, 2H) and 7.50 (d, 2H).

MS: ESP+(M+H)=345.

EXAMPLE 50

There is no compound with Example No. 50.

EXAMPLE 51

N-((5S)-3-(4-(2-Benzyloxymethyl-3,6- and -5,6-dihydropyran-4-yl)phenyl)-2-oxooxazolidin-5-ylmethyl)acetamide Reference Example 21 (0.28 g), palladium(0)bis (dibenzylideneacetone) (0.039 g), triphenylarsine (0.052 g) and lithium chloride (0.107 g) were dissolved in degassed N,N-dimethylformamide (8 ml). The stannane (Reference Example 1) (0.338 g) was added after 5 minutes and stirring was continued for 21 hours at 40° C. Aqueous potassium fluoride (2.0 ml, 2M) was added and stirring continued for 20 minutes whereupon the mixture was evaporated. The residue was partitioned between ethyl acetate (40 ml) and water (10 ml), and the organic layer dried and evaporated to an oil which was purified by silica-gel MPLC [using a mixture of 3% MeOH and $CH_2Cl_2$ as eluant]. The resultant foam was triturated with diethyl ether to give a mixture of the title compounds (0.204 g, 58%).

NMR (300 MHz, CDCl$_3$)d: 2.01 (s, H), 2.29–2.73 (m, 2H), 3.54–3.94 (m, 6H), 4.06 (t, 1H), 4.14–4.23 (m, 0.5H), 4.39–4.53 (m, 1.5H), 4.56–4.70 (m, 2H), 4.71–4.84 (m, 1H), 6.07 (d, 1H), 6.15 (t, 1H) and 7.29–7.51 (m, 9H,).

MS: ESP+(M+H)$^+$=437.

EXAMPLE 51A

N-((5S)-3-(4-(2-Benzyloxymethyl-3,6-dihydropyran-4-yl)phenyl)-2-oxooxazolidin-5-ylmethyl)acetamide Example 51A was prepared in an identical fashion to Example 51, but starting from Reference Example 24 instead of Reference Example 21.

NMR (300 MHz, CDCl$_3$)d: 2.01 (s, 3H), 2.28–2.50 (m, 2H), 3.54–3.94 (m, 6H), 4.09 (t, 1H), 4.32–4.50 (m, 2H), 4.61 (d, 1H), 4.67 (d, 1H), 4.72–4.83 (m, 1H), 6.10 (br s, 1H), 6.18 (t, 1H), 7.28–7.50 (m, 9H).

MS: ESP+(M+H)=437.

EXAMPLE 52

N-((5S)-3-(4-(2-Hydroxymethyl-3,6- and -5,6-dihydropyran-4-yl)phenyl)-2-oxooxazolidin-5-ylmethyl)acetamide The benzyl ether Example 51 (0.158 g) in dry dichloromethane (7 ml) at 0° C. was treated with boron trichloride-dimethyl sulfide (0.097 g, 0.27 ml) and stirred for 3 days. TLC indicated consumption of starting material. Methanol (5 ml) was added and stirring continued for 20 minutes. The solution was evaporated and the residue purified by silica-gel MPLC [using a mixture of 2% MeOH and $CH_2Cl_2$ as eluant] to give a mixture of the title compounds (0.043 g, 35%).

NMR (300 MHz, $CDCl_3$)d: 2.01 (s, 3H), 2.21–2.70 (m, 2 H), 3.55–3.85 (m, 6H), 4.09 (t, 1H), 4.10–4.20 (m, 0.5H), 4.35–4.45 (m, 1.5H), 4.70–4.82 (m, 1H), 5.98–6.15 (m, 2H) and 7.35–7.50 (m, 4H).

MS: ($ESP^+$)(M+H)=347.

EXAMPLE 52A

N-((5S)-3-(4-(2-Hydroxymethyl-3,6-dihydropyran-4-yl)phenyl)-2-oxooxazolidin-5-methyl)acetamide Example 52A was prepared in an identical fashion to Example 52, but starting from Example 51A rather than Example 51.

NMR (300 MHz, DMSO-D6)d: 1.82 (s, 3H), 2.11–2.40 (m, 2H), 3.37–3.79 (m, 7H), 3.99–4.35 (m, 2H), 4.10 (t, 1H), 4.62–4.80 (m, 1H), 6.18–6.25 (m, 1H), 7.40–7.55 (m, 4H), 8.20 (t, 1H).

MS. ESP+(M+H)=347.

EXAMPLE 53

N-((5S)-3-(4-(2-Acetamidomethyl-3,6- and -5,6-dihydropyran-4-yl)phenyl)-2-oxooxazolidin-5-ylmethyl)acetamide Trimethyl phosphite (1 ml) was added slowly under argon to a stirred solution of the azide Reference example 23 (0.138 g) in dimethoxyethane (2 ml) at 50° C. After 2.25 hours, the solution was evaporated, redissolved in dimethoxyethane (2 ml) and treated with 6N hydrochloric acid (0.065 ml). The mixture was refluxed for 0.25 hours, cooled and stirred at ambient temperature for 0.5 hours. The solution was evaporated to the crude amine hydrochloride. The amine hydrochloride (0.22 mmol) in dimethoxyethane (2 ml) and water (0.5 ml) was taken to pH 9 with 2.5M sodium hydroxide solution and then treated with acetic anhydride (0.075 g). After 2.5 hours, the solution was evaporated and purified by Isolute silica-gel chromatography [using a mixture of 5% MeOH and $CH_2Cl_2$ as eluant] to give the title mixture of compounds (0.063 g, 45%).

NMR (300 MHz, $CDCl_3$)d: 1.99, 2.02 and 2.03 (s/s/s, together 6H), 2.30–2.40 (m, 1H), 3.20–3.32 (m, 1H), 3.58–3.83 (m, 6H), 4.09 (t, 1H), 4.10–4.19 and 4.30–4.41 (m/m, together 2H), 4.74–4.82 (m, 1H), 5.98 and 6.09 (each broad s, together 2H), 6.43 (broad s, 1H ), 7.32–7.40 and 7.43–7.50 (m/m, together 4H).

MS: ESP+(M+H)=388.

EXAMPLE 54

N-((5S)-3-(4-(2-{Pyrimid-2-ylthio}methyl-3,6-dihydropyran-4-yl)phenyl)-2-oxooxazolidin-5-ylmethyl)acetamide The alcohol Example 52A (0.162 g), 2-mercaptopyrimidine (0.105 g) and N,N-dimethylformamide dineopentyl acetal (0.326 g, 0.393 ml) in dry acetonitrile (10 ml) were refluxed for 4.5 hours. The solution was cooled, evaporated and purified by silica-gel MPLC [using a mixture of 6% MeOH and $CH_2Cl_2$ as eluant] to give an oil which was triturated with diethyl ether to afford the title compound in crystalline form (0.134 g, 63%).

NMR (300 MHz, $CDCl_3$)d: 2.02 (s, 3H), 2.30–2.72 (m, 2H), 3.39–4.00 (m, 6H), 4.05 (t, 1H), 4.13–4.62 (m, 2H), 4.72–4.82 (m, 1H), 6.09–6.25 (m, 2H), 6.98 (t, 1H), 7.40 (d, 2H), 7.49 (d, 2H), 8.52 (d, 2H).

MS: ESP+(M+H)=441.

EXAMPLES 55 to 98

Carboxamides

Using a similar procedure to that described in Example 35, but starting with the appropriate carboxylic acid instead of 4-tert-butylhexanecarboxylic acid the following compounds of the formula XIV (Table A) were prepared by robotic synthesis (using a robot machine manufactured by Zymark). The procedure used is described below.

The TFA salt of Example 2 in DMF (0.75 mM, 4 ml) was added to the appropriate carboxylic acid (0.863 mM) under argon. To this was then added a solution of N-methylmorpholine in DMF (1 mM, 1 ml) and a solution of N-hydroxybenzotriazole in DMF (0.863 mM, 1 ml). The mixture was then stirred at ambient temperature for 5 minutes after which time a solution of 1-ethyl-3-dimethylaminopropyl-carbodiimide (EDC) in DMF (0.863 mmole, 3 ml) was added. The reaction was then stirred at ambient temperature overnight. The solvent was evaporated using centrifugal evaporation (SAVANT AES2000) using radiant cover for 3 hours. The residue was dissolved in $CH_2Cl_2$ (5 ml). The organics were sequentially washed with 1N HCl (4 ml), water (4 ml), saturated $NaHCO_3$ (4 ml) and brine (5 ml). The solvent was again removed by centrifugal evaporation (SAVANT AES2000) using low heat for 3 hours and the products transferred into 16×49 mm vials.

The less pure products were subjected to further purification by Bondelut Chromatography using conditions comparable to those of the TLC system used in earlier Examples ie. 5–10% MeOH/$CH_2Cl_2$. The relevant fractions were combined and the solvent removed by centrifugal evaporation (SAVANT AES2000) on low heat for 3 hours. The products were then transferred into 16×49 mm vials.

The compounds were analysed by mass spectroscopy and were characterised by HPLC retention time, using the HPLC conditions described in Example 35.

TABLE A

N-Acyl compounds:

(XIV)

| Example No. | R (Formula(XIV)) | MS Mol Ion (M + H) | Hplc retention time (min.) |
|---|---|---|---|
| 55 | [1R-(1A,2B,3A)]-(+)-3-methyl-2-(nitromethyl)-5-oxocyclopentaneacetyl- | 513 | 19.17 |
| 56 | 2-butoxyacetyl- | 430 | 19.57 |
| 57 | 5-fluoroindole-3-acetyl- | 491 | 19.78 |
| 58 | 3-acetyl-2,2-dimethylcyclobutyl-acetyl- | 482 | 19.17 |
| 59 | 2-cyclopenten-1-acetyl- | 424 | 20.15 |
| 60 | 2-napthoxyacetyl- | 500 | 21.63 |
| 61 | oxamoyl- | 463 | 19.95 |
| 62 | N-t-butoxycarbonylglycyl- | 473 | 19.08 |
| 63 | methylthioacetyl- | 404 | 17.77 |
| 64 | There is no compound with Example No. 64 | | |
| 65 | N-methyl-2-pyrroloyl- | 423 | 19.12 |
| 66 | trifluoroacetyl | 412 | 20.12 |
| 67 | 3-(2-furyl)-acryloyl- | 436 | 19.60 |
| 68 | 3-furoyl- | 410 | 18.10 |
| 69 | 3-(2-thienyl)-acryoyl- | 452 | 20.23 |
| 70 | thiophene-2-acetyl- | 440 | 19.28 |
| 71 | thiophen-3-oyl- | 426 | 18.78 |
| 72 | There is no compound with Example No. 72 | | |
| 73 | indole-3-acetyl- | 473 | 19.50 |
| 74 | There is no compound with Example No. 74 | | |
| 75 | There is no compound with Example No. 75 | | |
| 76 | (2-pyrimidylthio)-acetyl- | 468 | 17.68 |
| 77 | 3,4-dihydro-2H-pyranoyl- | 426 | 18.77 |
| 78 | 5-(O-methyl)-comenoyl- | 468 | 15.15 |
| 79 | 1,4-benzodioxan-6-acetyl- | 492 | 19.32 |
| 80 | 3-(phenylsulfonyl)-propionoyl- | 512 | 18.88 |
| 81 | 4-(aminosulfonyl)-benzoyl- | 499 | 16.93 |
| 82 | 4-(diethylaminosulfonyl)-benzoyl- | 583 | 22.38 |
| 83 | 4-(dimethylamino)-butyroyl- | 429 | 15.20 |
| 84 | N-acetyl-L-prolyl- | 455 | 16.23 |
| 85 | 2,3,4-trimethoxycinnamoyl- | 536 | 20.42 |
| 86 | There is no compound with Example No. 86 | | |
| 87 | (R)-5-oxo-2-tetrahydrofuroyl- | 428 | 16.43 |
| 88 | 7-oxo-octanoyl- | 456 | 18.38 |
| 89 | There is no compound with Example No. 89 | | |
| 90 | 2-benzofuranoyl- | 460 | 20.95 |
| 91 | indole-1-acetyl- | 473 | 20.97 |
| 92 | sulfolanyl-3-acetyl- | 476 | 16.67 |
| 93 | 4-oxo-1H-1-benzo-2-pyranoyl- | 488 | 19.18 |
| 94 | There is no compound with Example No. 94 | | |
| 95 | indole-3-oyl- | 459 | 18.98 |
| 96 | 2-(n-propylthio)-nicotinoyl- | 495 | 20.62 |
| 97 | 2-methoxy-pyridin-3-oyl- | 451 | 17.95 |
| 98 | 2,3-dihydro-5-oxothiazolo-[3,2-A]-pyrimidin-6-oyl- | 496 | 16.37 |

EXAMPLES 99 TO 139

Sulfonamides

Using a similar procedure to that described in Example 38, but starting with the appropriate sulfonyl chloride instead of p-toluenesulfonyl chloride the following compounds of the formula XV (Table B) were prepared by robotic synthesis (using a robot machine manufactured by Zymark). The procedure used is described below.

The TFA salt of Example 2 (279 mg, 0.65 mM) was suspended in $CH_2Cl_2$ (10 ml). To this was added triethylamine (243 μl) and then a solution of the appropriate sulfonyl chloride in $CH_2Cl_2$ (0.78 mM in 5 ml). The mixture went into solution after 10–15 minutes and the reaction was then stirred at ambient temperature for a further 4 hours. The compounds were subjected to purification by Bondelut Chromatography using conditions comparable to those of the TLC system used in earlier Examples ie. 5–10% MEOH/$CH_2Cl_2$. The relevant fractions were combined and the solvent removed by centrifugal evaporation (SAVANT AES2000) on low heat for 3 hours. The products were then transferred into 16×49 mm vials.

The compounds were analysed by mass spectroscopy and were characterised by HPLC retention time, using the HPLC conditions described in Example 35.

TABLE B

N-Sulfonyl compounds:

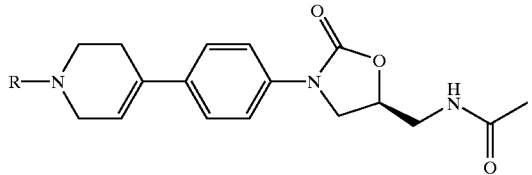

(XV)

| Example No. | R (Formula (XV)) | MS Mol Ion (M + H) | Hplc retention time (min.) |
|---|---|---|---|
| 99 | 8-quinoline-sulfonyl- | 507 | 19.93 |
| 100 | 2-naphthalene-sulfonyl- | 504 | 22.82 |
| 101 | 2-methoxycarbonylphenyl-sulfonyl | 514 | 20.65 |
| 102 | 4-fluorobenzene-sulfonyl- | 474 | 21.38 |
| 103 | 3-chloropropane-sulfonyl- | 456 | 20.17 |
| 114 | 4-chlorobenzene-sulfonyl- | 490 | 22.43 |
| 115 | 4-carboxybenzene-sulfonyl- | 498* | 19.75 |
| 116 | isopropylsulfonyl- | 422 | 19.28 |
| 117 | b-styrylsulfonyl- | 482 | 21.88 |
| 118 | ethanesulfonyl- | 408 | 18.35 |
| 119 | 1-butanesulfonyl- | 436 | 20.70 |
| 120 | 1-octanesulfonyl- | 492 | 25.07 |
| 121 | 2-chlorobenzene-sulfonyl- | 490 | 21.67 |
| 122 | 3-carboxybenzene-sulfonyl- | 498* | 19.23 |
| 123 | 3-trifluoromethylbenzene-sulfonyl- | 524 | 22.77 |
| 124 | 2,2,2-trifluoroethanesulfonyl- | 462 | 20.48 |
| 125 | 5-chlorothiophene-sulfonyl- | 496 | 22.72 |
| 126 | 2-(pyrid-2-yl)-thiophene-5-sulfonyl- | 539 | 21.68 |
| 127 | 2,4-difluorobenzene-sulfonyl- | 492 | 21.62 |
| 128 | 3-fluorobenzene-sulfonyl- | 474 | 21.50 |
| 129 | 4-acetamidobenzene-sulfonyl- | 513 | 18.90 |
| 130 | 1-methylimidazol-4-yl-sulfonyl- | 460 | 17.03 |
| 131 | 5-(isoxazol-3-yl)-thiophene-2-sulfonyl- | 529 | 21.50 |
| 132 | 5-bromothiophene-2-sulfonyl- | 540 | 22.83 |
| 134 | 4-cyanobenzene-sulfonyl- | 481 | 20.85 |
| 135 | 4-trifluoromethoxybenzene-sulfonyl- | 540 | 22.15 |
| 136 | 4-trifluoromethylbenzene-sulfonyl- | 524 | 22.93 |
| 137 | 3,4-dimethoxybenzene-sulfonyl- | 516 | 20.27 |
| 138 | 5-dimethylamino-1-naphthalene-sulfonyl- | 549 | 20.15 |
| 139 | benzenesulfonyl- | 456 | 21.00 |

*M − H
NB. There are no compounds with Example Nos. 104–113 and 133.

EXAMPLE 140

The Following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 179 |
| | Croscarmellose sodium | 12 |
| | Polyvinylpyrrolidone | 6 |
| | Magnesium stearate | 3 |
| (b) | Tablet II | mg/tablet |
| | Compound X | 50 |
| | Lactose Ph.Eur | 229 |
| | Croscarmellose sodium | 12 |
| | Polyvinylpyrrolidone | 6 |
| | Magnesium stearate | 3 |
| (c) | Tablet III | mg/tablet |
| | Compound X | 1 |
| | Lactose Ph.Eur | 92 |
| | Croscarmellose sodium | 4 |
| | Polyvinylpyrrolidone | 2 |
| | Magnesium stearate | 1 |
| (d) | Capsule | mg/capsule |
| | Compound X | 10 |
| | Lactose Ph.Eur | 389 |
| | Croscarmellose sodium | 100 |
| | Magnesium stearate | 1 |
| (e) | Injection I | (50 mg/ml) |
| | Compound X | 5.0% w/v |
| | Isotonic aqueous solution | to 100% |

Buffers, pharmaceutically-acceptable cosolvents such as polyethylene glycol, polypropylene glycol, glycerol or ethanol or complexing agents such as hydroxy-propyl, β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula (I):

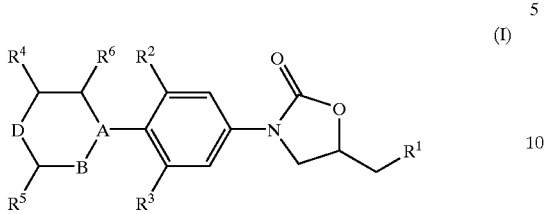

wherein:

$R^1$ is hydroxy, chloro, fluoro, (1–4C)alkanesulfonyloxy, amino, azido, (1–4C)alkoxy, (1–4C)alkylthio, (1–4C)alkylaminocarbonyloxy;

or of the formula —NHC(=O)$R^b$ wherein $R^b$ is hydrogen, (1–4C)alkoxy, amino, chloromethyl, dichloromethyl, cyanomethyl, methoxymethyl, acetylmethyl, methylamino, dimethylamino or (1–4C)alkyl;

or $R^1$ is of the formula —NHS(O)$_n$(1–4C)alkyl wherein n is 0, 1 or 2;

$R^2$ and $R^3$ are independently fluoro;

D is S, SO or SO$_2$;

$R^4$ and $R^5$ are independently hydroxy, bromo, (1–4C)alkanoylamino-(1–4C)alkyl, hydroxy-(1–4C)alkyl, carboxy, (1–4C)alkoxycarbonyl, AR-oxymethyl, AR-thiomethyl or independently as defined for $R^7$;

$R^6$ is hydroxy, (1–4C)alkoxy or (2–4C)alkanoyloxy;

>A—B— is of the formula >C=C($R^a$)—, >CHCHR$^a$—, or >C(OH)CHR$^a$— wherein $R^a$ is hydrogen or (1–4C)alkyl;

$R^7$ is cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl, AR or a tetrazole ring system (optionally mono-substituted in the 1- or 2-position of the tetrazole ring);

or $R^7$ is of the formula $R^{10}$CO—, $R^{10}$SO$_2$— or $R^{10}$CS— wherein $R^{10}$ is AR, cyclopentyl or cyclohexyl (wherein the last two-mentioned cycloalkyl rings are optionally mono- or disubstituted by substituents independently selected from (1–4C)alkyl (including geminal disubstitution), hydroxy, (1–4C)alkoxy, (1–4C)alkylthio, acetamido, (1–4C)alkanoyl, cyano and trifluoromethyl), (1–4C)alkoxycarbonyl, hydrogen, amino, trifluoromethyl, (1–4C)alkylamino, di((1–4C)alkyl)amino, 2,3-dihydro-5-oxothiazolo-[3,2-A]pyrimidin-6-yl, 2-(2-furyl)ethenyl, 2-(2-thienyl)ethenyl, 2-phenylethenyl (wherein the phenyl substituent is optionally substituted by up to three substituents independently selected from (1–4C)alkoxy, halo and cyano), 3,4-dihydropyran-2-yl, coumal-5-yl, 5-methoxy-4-oxopyran-2-yl, N-acetylpyrrolidin-2-yl, 5-oxo-tetrahydrofuran-2-yl, benzopyranone or (1–10C)alkyl [wherein (1–10C)alkyl is optionally substituted by hydroxy, cyano, halo, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, amino, (1–4C)alkylamino, di((1–4C)alkyl)amino, (1–6C)alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N—, fluoro(1–4C)alkylS(O)$_p$NH—, fluoro(1–4C)alkylS(O)$_p$((1–4C)alkyl)N—, phosphono, (1–4C)alkoxy(hydroxy)phosphoryl, di-(1–4C)alkoxyphosphoryl, (1–4C)alkylS(O)$_q$—, phenylS(O)$_q$— (wherein the phenyl group is optionally substituted by up to three substituents independently selected from (1–4C)alkoxy, halo and cyano), or CY, wherein p is 1 or 2 and q is 0, 1 or 2];

or $R^{10}$ is of the formula $R^{11}$C(O)O(1–6C)alkyl wherein $R^{11}$ is an optionally substituted 5- or 6-membered heteroaryl, optionally substituted phenyl, (1–4C)alkylamino, benzyloxy-(1–4C)alkyl or optionally substituted (1–10C)alkyl;

or $R^{10}$ is of the formula $R^{12}$O— wherein $R^{12}$ is optionally substituted (1–6C)alkyl;

or $R^7$ is of the formula $R^dOC(R^e)$=CH(C=O)—, $R^fC(=O)C(=O)$—, $R^gN=C(R^h)C(=O)$— or $R^iNHC(R^j)$=CHC(=O)— wherein $R^d$ is (1–6C)alkyl, $R^e$ is hydrogen or (1–6C)alkyl, or $R^d$ and $R^e$ together form a (3–4C)alkylene chain, $R^f$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy, $R^g$ is (1–6C)alkyl, hydroxy or (1–6C)alkoxy, $R^h$ is hydrogen or (1–6C)alkyl, $R^i$ is hydrogen, (1–6C)alkyl, optionally substituted phenyl or an optionally substituted 5- or 6-membered heteroaryl and $R^j$ is hydrogen or (1–6C)alkyl;

or $R^7$ is of the formula $R^{14}$CH($R^{13}$) (CH$_2$)$_m$— wherein m is 0 or 1, $R^{13}$ is fluoro, cyano, (1–4C)alkoxy, (1–4C)alkylsulfonyl, (1–4C)alkoxycarbonyl or hydroxy, (provided that when m is 0, $R^{13}$ is not fluoro or hydroxy) and $R^{14}$ is hydrogen or (1–4C)alkyl;

wherein AR is optionally substituted phenyl, optionally substituted phenyl(1–4C)alkyl, optionally substituted 5- or 6-membered heteroaryl, optionally substituted naphthyl or an optionally substituted 5/6 or 6/6 bicyclic heteroaryl ring system, in which the bicyclic heteroaryl ring systems may be linked via an atom in either of the rings comprising the bicyclic system, and wherein the mono- and bicyclic heteroaryl ring systems are linked via a ring carbon atom; wherein CY is a 4-, 5- or 6-membered cycloalkyl ring, a 5- or 6-membered cycloalkenyl ring, naphthoxy, thiophen-2-yl, indol-1-yl, indol-3-yl, pyrimidin-2-ylthio, 1,4-benzodioxan-6-yl, sulfolan-3-yl, pyridin-2-yl; wherein any of the afore-mentioned ring systems in CY may be optionally substituted by up to three substituents independently selected from halo, (1–4C)alkyl (including geminal disubstitution when CY is a cycloalkyl or cycloalkenyl ring), acyl, oxo and nitro-(1–4C)alkyl; pharmaceutically-acceptable salts thereof; and in-vivo-hydrolysable esters thereof.

2. A compound of claim 1, of the formula (IB):

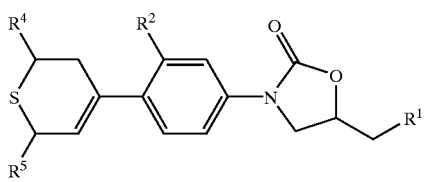

wherein $R^1$ is hydroxy or acetamido; $R^2$ is hydrogen or fluoro and $R^4$ and $R^5$ are independently hydroxy, bromo, carboxy, (1–4C)alkoxycarbonyl, hydroxymethyl, (1–4C) alkoxymethyl or carbamoyl; pharmaceutically-acceptable salts thereof; and in-vivo-hydrolysable esters thereof.

3. A compound of claim 1 or 2, wherein $R^1$ is acetamido; $R^2$ is hydrogen or fluoro and $R^4$ and $R^5$ are independently AR-oxymethyl or AR-thiomethyl (wherein AR is phenyl, phenyl(1–4C)alkyl, naphthyl, furan pyrrole, pyrazole, imidazole, triazole, pyrimidine, pyridazine, pyridine, isoxazole, oxazole, isothiazole, or thiophene); and pharmaceutically-acceptable salts thereof.

4. A pharmaceutical composition comprising a compound of claim 1, 2, or 3, a pharmaceutically acceptable salt thereof, or an in-vivo-hydrolysable ester thereof, and a pharmaceutically acceptable diluent or carrier.

5. A method for producing an antibacterial effect in a warm-blooded animal in need of such treatment, comprising administering to said animal an effective amount of a compound of claim 1, 2, or 3, a pharmaceutically acceptable salt thereof, or an in-vivo-hydrolysable ester thereof.

6. The method of claim 5, wherein the animal is a human.

* * * * *